(12) United States Patent
Burnstein et al.

(10) Patent No.: US 11,994,511 B2
(45) Date of Patent: May 28, 2024

(54) BIOMARKERS INDICATIVE OF PROSTATE CANCER AND TREATMENT THEREOF

(71) Applicant: UNIVERSITY OF MIAMI, Miami, FL (US)

(72) Inventors: Kerry L. Burnstein, Miami, FL (US); Fiorella Magani, Miami, FL (US)

(73) Assignee: UNIVERSITY OF MIAMI, Miami, FL (US)

( * ) Notice: Subject to any disclaimer, the term of this patent is extended or adjusted under 35 U.S.C. 154(b) by 1239 days.

(21) Appl. No.: 16/500,722

(22) PCT Filed: Apr. 4, 2018

(86) PCT No.: PCT/US2018/026097
§ 371 (c)(1),
(2) Date: Oct. 3, 2019

(87) PCT Pub. No.: WO2018/187478
PCT Pub. Date: Oct. 11, 2018

(65) Prior Publication Data
US 2023/0133972 A1 May 4, 2023

Related U.S. Application Data

(60) Provisional application No. 62/481,336, filed on Apr. 4, 2017.

(51) Int. Cl.
*A61K 38/00* (2006.01)
*C12Q 1/6886* (2018.01)
*G01N 33/50* (2006.01)

(52) U.S. Cl.
CPC ....... *G01N 33/5011* (2013.01); *C12Q 1/6886* (2013.01); *G01N 33/5044* (2013.01); *C12Q 2600/158* (2013.01)

(58) Field of Classification Search
CPC .................................................. G01N 33/5011
See application file for complete search history.

(56) References Cited

U.S. PATENT DOCUMENTS

| | | | |
|---|---|---|---|
| 2003/0186999 A1 | 10/2003 | Meijer et al. | |
| 2010/0272717 A1 | 10/2010 | Evans et al. | |
| 2010/0305057 A1 | 12/2010 | Rathos et al. | |
| 2013/0029928 A1* | 1/2013 | Elcombe | A61K 45/06 514/183 |

FOREIGN PATENT DOCUMENTS

WO 2007/044515 A1 4/2007

OTHER PUBLICATIONS

Mostaghel et al., Resistance to CYP17A1 inhibition with abiraterone in castration-resistant prostate cancer: induction of steroidogenesis and androgen receptor splice variants, Clinical Cancer Research, 17(18):5913-5925 (2011).
Prensner et al., Beyond PSA: the next generation of prostate cancer biomarkers, Science Translational Medicine, 4(127):127rv3 (2012).
Qu et al., Constitutively active AR-V7 plays an essential role in the development and progression of castration-resistant prostate cancer, Scientific Reports, 5:7654 (2015).
Rafi et al., Lycopene modulates growth and survival associated genes in prostate cancer, J. Nutr. Bio., 24(10):1724-1734 (2013).
Rhodes et al., Integrative analysis of the cancer transcriptome, Nature Genetics, 37:S31-S37 (2005).
Robinson et al., Integrative clinical genomics of advanced prostate cancer, Cell, 161(5):1215-1228 (2015).
Satake et al., The ubiquitin-like molecule interferon-stimulated gene 15 is overexpressed in human prostate cancer, Oncology Reports, 23(1):11-16 (2010).
Shafi et al., Differential regulation of metabolic pathways by androgen receptor (AR) and its constitutively active splice variant, AR-V7, in prostate cancer cells, Oncotarget, 6(31):31997-32012 (2015).
Siegel et al., Cancer statistics, 2016, CA: a cancer journal for clinicians, 66(1):7-30 (2016).
Sun et al., Castration resistance in human prostate cancer is conferred by a frequently occurring androgen receptor splice variant, J. Clin. Inv., 120(8):2715-2730 (2010).
Tacar et al., Doxorubicin: an update on anticancer molecular action, toxicity and novel drug delivery systems, J. Pharm. Pharmacol., 65(2):157-170 (2013).
Vaarala et al., Identification of androgen-regulated genes in human prostate, Molecular Medicine Reports, 6(3):466-472 (2012).
Varambally et al., Integrative genomic and proteomic analysis of prostate cancer reveals signatures of metastatic progression, Cancer Cell, 8(5):393-406 (2005).
Vella et al., Targeting CDKs with Roscovitine Increases Sensitivity to DNA Damaging Drugs of Human Osteosarcoma Cells, Plos One, 11:1-20 (2016).
Wang et al., In silico estimates of tissue components in surgical samples based on expression profiling data, Cancer Research, 70(16):6448-6455 (2010).
Watson et al., Constitutively active androgen receptor splice variants expressed in castration-resistant prostate cancer require full-length androgen receptor, Proc. Natl. Acad. Sci. USA, 107(39):16759-16765 (2010).
Wiley et al., Yeast Augmented Network Analysis (YANA): a new systems approach to identify therapeutic targets for human genetic diseases, F1000Res., 3:121 (2014).
Xu et al., Androgen Receptor Splice Variants Dimerize to Transactivate Target Genes, Cancer Research, 75(17):3663-3671 (2015).
Yang et al., Novel membrane-associated androgen receptor splice variant potentiates proliferative and survival responses in prostate cancer cells, J. Biol. Chem., 286(41):36152-36160 (2011).
Yu et al., Androgen receptor promotes the oncogenic function of overexpressed Jagged1 in prostate cancer by enhancing cyclin B1 expression via Akt phosphorylation, Mol. Cancer Research, 12(6):830-842 (2014).
Zhang et al., A general framework for weighted gene co-expression network analysis, Stat. App. Gen. Mol. Biol., 4(1):1-45 (2005).
Zhang et al., Androgen receptor variants occur frequently in castration resistant prostate cancer metastases, PloS One, 6(11):e27970 (2011).

(Continued)

*Primary Examiner* — Albert M Navarro
(74) *Attorney, Agent, or Firm* — MARSHALL, GERSTEIN & BORUN LLP

(57) ABSTRACT

Described herein are materials and methods for the treatment of prostate cancer.

14 Claims, 27 Drawing Sheets

Specification includes a Sequence Listing.

(56) References Cited

OTHER PUBLICATIONS

Zhu et al., MetaDCN: meta-analysis framework for differential co-expression network detection with an application in breast cancer, Bioinformatics, 33(8):1121-1129 (2017).
Antonarakis et al., AR-V7 and resistance to enzalutamide and abiraterone in prostate cancer, N. Engl. J. Med., 371(11):1028-1038 (2014).
Antonarakis et al., Clinical Significance of Androgen Receptor Splice Variant-7 mRNA Detection in Circulating Tumor Cells of Men With Metastatic Castration-Resistant Prostate Cancer Treated With First- and Second-Line Abiraterone and Enzalutamide, J. Clin. Oncol., 35(19):2149-2156 (2016).
Appleyard et al., Seliciclib (CYC202, R-roscovitine) enhances the antitumor effect of doxorubicin in vivo in a breast cancer xenograft model, int. J. Cancer., 124(2):465-472 (2009).
Arová et al., Synthetic inhibitors of CDKs induce different responses in androgen sensitive and androgen insensitive prostatic cancer cell lines, J. Clin. Pathol. Mol. Pathol., 55(4): 227-234 (2002).
Arredouani et al., Identification o f the transcription factor single-minded homologue 2 as a potential biomarker and immunotherapy target in prostate cancer, Clinical Cancer Research, 15(18):5794-5802 (2009).
Balk et al., AR, the cell cycle, and prostate cancer, Nuclear receptor signaling, 6:e001 (2008).
Bjartell et al., Tumour markers in prostate cancer II: diagnostic and prognostic cellular biomarkers, Acta Oncologica, 50(supl 1):76-84 (2011).
Cao et al., Androgen receptor splice variants activating the full-length receptor in mediating resistance to androgen-directed therapy, Oncotarget, 5(6):1646-1656 (2014).
Chan et al., Androgen receptor splice variants activate androgen receptor target genes and support aberrant prostate cancer cell growth independent of canonical androgen receptor nuclear localization signal, Journal of Biological Chemistry, 287(23):19736-19749 (2012).
Chan et al., Targeting chromatin binding regulation of constitutively active AR variants to overcome prostate cancer resistance to endocrine-based therapies, Nucleic Acids Research, 43(12):5880-5897 (2015).
Chandran et al., A systems-level analysis of the peripheral nerve intrinsic axonal growth program, Neuron, 89(5):956-970 (2016).
Chen et al., Androgen receptor phosphorylation and stabilization in prostate cancer by cyclin-dependent kinase 1, Proc. Natl. Acad. Sci. USA, 103(43):15969-15974 (2006).
Chia et al., A feedback loop between androgen receptor and ERK signaling in estrogen receptor-negative breast cancer, Neoplasia., 13(2):154-166 (2011).
Chou et al., Quantitative analysis of dose-effect relationships: the combined effects of multiple drugs or enzyme inhibitors, Adv. Enzy. Regul., 22: 27-55 (1984).
ClinicalTrials.gov, Study NCT01240629 on Date: Feb. 3, 2017, ClinicalTrials.gov., (2017).
Cooperberg et al., Trends in management for patients with localized prostate cancer, 1990-2013, JAMA, 314(1):80-82 (2015).
Cottard et al., Constitutively active androgen receptor variants upregulate expression of mesenchymal markers in prostate cancer cells, PloS One, 8(5):e63466 (2013).
Cuzick et al., Prognostic value of an RNA expression signature derived from cell cycle proliferation genes in patients with prostate cancer: a retrospective study, The Lancet Oncology, 12(3):245-255 (2011).
Dehm et al., Splicing o f a novel androgen receptor exon generates a constitutively active androgen receptor that mediates prostate cancer therapy resistance, Cancer Research, 68(13):5469-5477 (2008).
Dixon et al., Significant conservation of synthetic lethal genetic interaction networks between distantly related eukaryotes, Proc. Natl. Acad. Sci. USA, 105(43):16653-16658 (2008).
Edamatsu et al., Cdk inhibitors, roscovitine and olomoucine, synergize with farnesyltransferase inhibitor NFTI) to induce efficient apoptosis of human cancer cell lines, Oncogono, 19(27):3059-3068 (2000).
European Application No. 18781789.5, Supplementary European Search Report and Opinion, dated Nov. 18, 2020.
Federico et al., R-Roscovitine (Seliciclib) prevents DNA damage-induced cyclin AI upregulation and hinders non-homologous end-joining (NHEJ) DNA repair, Mol. Canc., 9(1):208 (2010).
Goodwin et al., DNA-PKcs-Mediated Transcriptional Regulation Drives Prostate Cancer Progression and Metastasis, Cancer Cell, 28(1):97-113 (2015).
Gumulec et al., Modulation of Induced Cytotoxicity of Doxorubicin by Using Apoferritin and Liposomal Cages, Int. J. Mol. Sci., 15:22960-22977 (2014).
Guo et al., A novel androgen receptor splice variant is up-regulated during prostate cancer progression and promotes androgen depletion-resistant growth, Cancer Research, 69(6):2305-2313 (2009).
Havlicek et al., Cytokinin-derived cyclin-dependent kinase inhibitors: synthesis and cdc2 inhibitory activity of olomoucine and related compounds, J. Med. Chem., 40(4):408-412 (1997).
He et al., Androgen receptor splice variants bind to constitutively open chromatin and promote abiraterone-resistant growth of prostate cancer, Nucleic Acids Res., 46(4):1895-1911 (2018).
Ho et al., Androgen Receptor Rearrangement and Splicing Variants in Resistance to Endocrine Therapies in Prostate Cancer, Endocrinology, 158(6):1533-1542 (2017).
Hornberg et al., Expression of androgen receptor splice variants in prostate cancer bone metastases is associated with castration-resistance and short survival, PloS One, 6(4):e19059 (2011).
Hu et al., Distinct transcriptional programs mediated by the ligand-dependent full-length androgen receptor and its splice variants in castration-resistant prostate cancer, Cancer Res., 72(14):3457-3462 (2012).
International Application No. PCT/US2018/026097, International Preliminary Report on Patentability, dated Oct. 17, 2019.
International Application No. PCT/US2018/026097, International Search Report and Written Opinion, dated Jul. 13, 2018.
Jia et al., Diagnosis of prostate cancer using differentially expressed genes in stroma, Cancer Research, 71(7):2476-2487 (2011).
Kadarmideen et al., Building gene co-expression networks using transcriptomics data for systems biology investigations: Comparison of methods using microarray data, Bioinformation, 8(18):855-861 (2012).
Karacosta et al., A regulatory feedback loop between Ca2+/calmodulin-dependent protein kinase kinase 2 (CaMKK2) and the androgen receptor in prostate cancer progression, J. Biol. Chem., 287(29):24832-24843 (2012).
Karantanos et al., Prostate cancer progression after androgen deprivation therapy: mechanisms of castrate resistance and novel therapeutic approaches, Oncogene., 32(49):5501-5511 (2013).
Knudsen et al., Partners in crime: deregulation of AR activity and androgen synthesis in prostate cancer, Trends in Endocrinology & Metabolism, 21(5):315-324 (2010).
Kong et al., Androgen receptor splice variants contribute to prostate cancer aggressiveness through induction of EMT and expression of stem cell marker genes, The Prostate, 75(2):161-174 (2015).
Kreeger et al., Cancer systems biology: a network modeling perspective, Carcinogenesis, 31(1):2-8 (2010).
Kregel et al., Acquired resistance to the second-generation androgen receptor antagonist enzalutamide in castration-resistant prostate cancer, Oncotarget, 7(18):26259-26274 (2016).
Lamb et al., The Connectivity Map: using gene-expression signatures to connect small molecules, genes, and disease, Science, 313(5795):1929-1935 (2006).
Langfelder et al., WGCNA: an R package for weighted correlation network analysis, BMC Bioinformatics, 9:559 (2008).
Li et al., Androgen receptor splice variants mediate enzalutamide resistance in castration-resistant prostate cancer cell lines, Cancer Research, 73(2):483-489 (2013).
Li et al., Catalytic inhibitors of DNA topoisomerase II suppress the androgen receptor signaling and prostate cancer progression, Oncotarget, 6(24):20474-20484 (2015).

(56) References Cited

OTHER PUBLICATIONS

Lokhandwala et al., Analytical Validation of Androgen Receptor Splice Variant 7 Detection in a Clinical Laboratory Improvement Amendments (CLIA) Laboratory Setting, J. Mol. Diag., 19(1):115-125 (2017).

Luo et al., Role of Androgen Receptor Variants in Prostate Cancer: Report from the 2017 Mission Androgen Receptor Variants Meeting, Eur. Urol., 73(5):715-723 (2017).

Marcias et al., Identification of novel truncated androgen receptor (AR) mutants including unreported pre-mRNA splicing variants in the 22Rv1 hormone-refractory prostate cancer (PCa) cell line, Human Mutation, 31(1):74-80 (2010).

Moreno et al., Molecular genetic analysis of fission yeast *Schizosaccharomyces pombe*, Met. Enzy., 194:795-823 (1991).

Mortensen et al., Expression profiling of prostate cancer tissue delineates genes associated with recurrence after prostatectomy, Scientific Reports, 5:16018 (2015).

\* cited by examiner

| Symbol | Description | WGCNA module | Interaction with AR-V7 (p value) | Regulation by AR-V7 (p value) |
|---|---|---|---|---|
| KIF20A | Kinesin | green | 0.05 | <0.001 |
| KIF23 | Kinesin | green | 0.01 | 0.05 |
| TOP2A | Topoisomerase II | green | 0.01 | <0.001 |
| CCNB1 | Cyclin B1 | green | 0.05 | <0.001 |
| CCNB2 | Cyclin B2 | green | 0.01 | 0.007 |
| BUB1 | Mitotic spindle checkpoint | green | 0.01 | <0.001 |
| BUB1b | Mitotic spindle checkpoint | green | 0.01 | <0.001 |

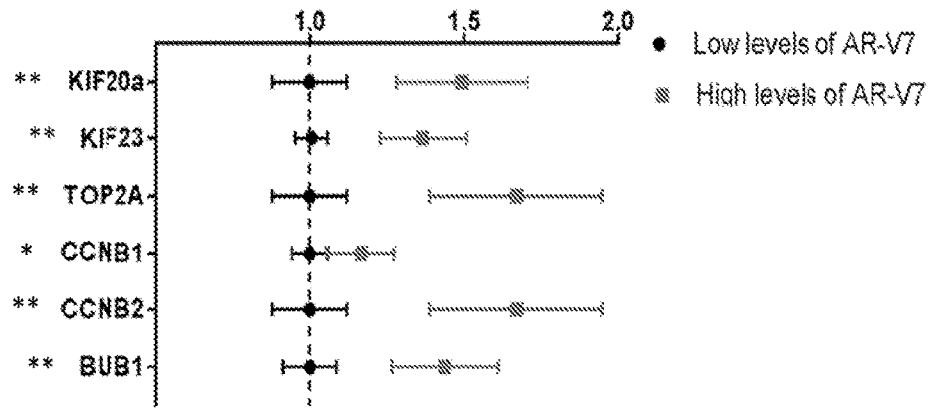
Figure 2A
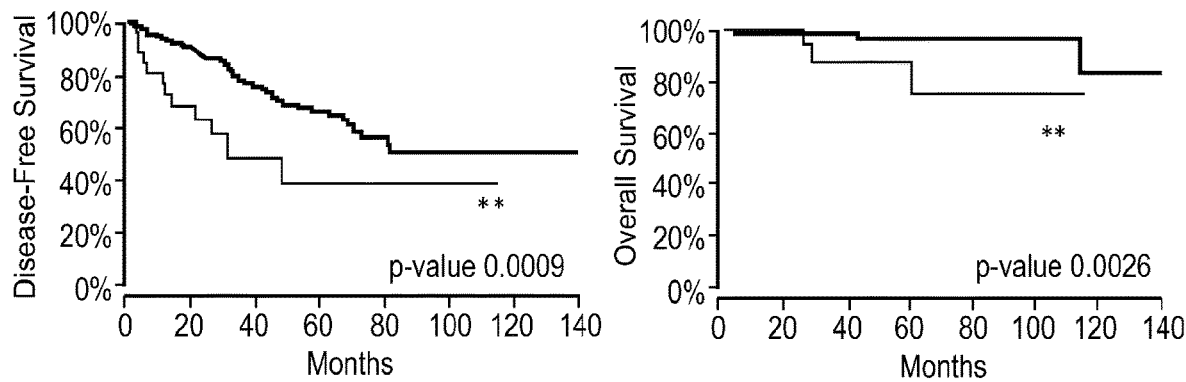
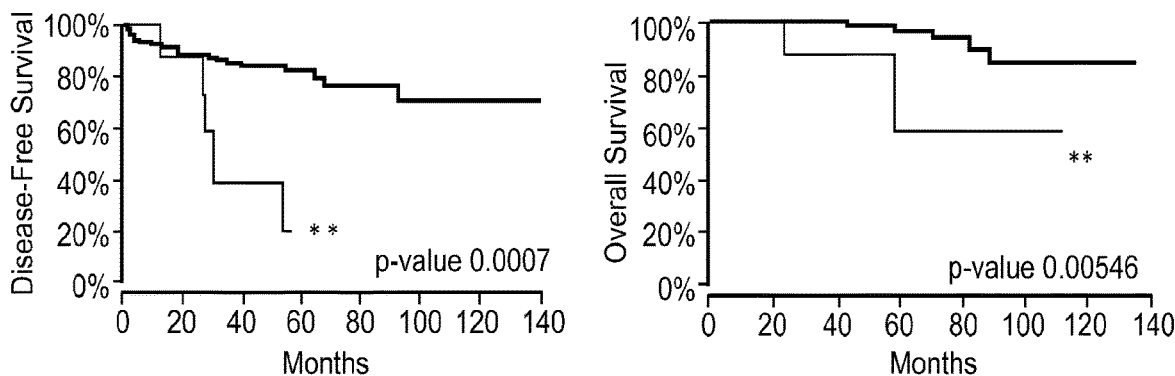
Figure 2B

| Symbol | Dose DOX (ng/mL) | Dose N-9 (ng/mL) | Combination Index (CI) |
|---|---|---|---|
| ⊙ | 100.0 | 100.0 | 0.56669 |
| □ | 100.0 | 250.0 | 0.75105 |
| △ | 250.0 | 100.0 | 0.69826 |
| ▽ | 50.0 | 500.0 | 0.76248 |
| ◇ | 100.0 | 200.0 | 0.45796 |
| × | 250.0 | 250.0 | 0.74909 |

| Dataset Identifier | Array | Tissue | Number of samples | Reference |
|---|---|---|---|---|
| EMEXP1243 | U133plus2 | Human | 81 | Traka et al., 2008 |
| GSE17951 | U133plus2 | Human | 154 | Jia et al., 2011 |
| GSE32982 | U133plus2 | Human | 9 | Vaarala et al., 2012 |
| GSE3325 | U133plus2 | Human | 19 | Varambally et al., 2005 |
| GSE45016 | U133plus2 | Human | 11 | Satake et al., 2010 |
| GSE46602 | U133plus2 | Human | 50 | Unpublished |
| GSE55945 | U133plus2 | Human | 21 | Arredouani et. al., 2009 |
| GSE7307 | U133plus2 | Human | 30 | Rands et. al., 2009 |
| | | TOTAL | 375 | |

Figure 5A

| Phenotype | Number of samples |
|---|---|
| Normal Prostate Tissue | 129 |
| Benign Prostatic Hyperplasia (BPH) | 25 |
| High-Grade Prostatic Intraepithelial neoplasia (HGPIN) | 76 |
| Cancerous | 120 |
| Castration Resistant Prostate Cancer (CRPC) | 8 |
| Metastasis | 17 |
| Patient Age at Biopsy | 118 |
| Gleason Grade | 67 |

Figure 5B

| Rank | Enrichment P | Bonferroni P | Process |
|---|---|---|---|
| 1 | 2.41E-41 | 3.83E-37 | mitotic cell cycle |
| 2 | 5.57E-39 | 8.85E-35 | cell cycle |
| 3 | 2.12E-37 | 3.36E-33 | cell cycle process |
| 4 | 2.94E-35 | 4.67E-31 | mitotic cell cycle process |
| 5 | 1.85E-33 | 2.95E-29 | cell division |
| 6 | 6.06E-32 | 9.63E-28 | mitotic nuclear devision |
| 7 | 8.23E-28 | 1.31E-23 | chromosome segregation |
| 8 | 2.95E-22 | 4.69E-18 | sister chromatid segregation |

Figure 5E

Network Stats number of nodes: 273
number of edges: 358
average node degree: 2.62
clustering coefficient: 0.876
expected number of edges: 209
PPI enrichment p-value: 0
*your network has significantly more interactions than expected (what does that mean?)*

Functional enrichments in your network

Biological Process (GO)

| pathway ID | pathway description | count in network | false discovery rate |
|---|---|---|---|
| GO:0070972 | protein localization to endoplasmic reticulum | 25 | 1.24e-17 |
| GO:0000184 | nuclear-transcribed mRNA catabolic process, nonsense-mediated decay | 23 | 7.77e-17 |
| GO:0000956 | nuclear-transcribed mRNA catabolic process | 26 | 1.73e-16 |
| GO:0006614 | SRP-dependent cotranslational protein targeting to membrane | 21 | 1.94e-15 |
| GO:0019083 | viral transcription | 21 | 3.29e-15 |
| | | | *(more...)* |

Molecular Function (GO)

| pathway ID | pathway description | count in network | false discovery rate |
|---|---|---|---|
| GO:0003735 | strutural constituent of ribosome | 15 | 1.48e-07 |
| GO:0003824 | catalytic activity | 112 | 1.48e-07 |
| GO:0005342 | organic acid transmembrane transporter activity | 14 | 1.48e-07 |
| GO:0008514 | organic anion transmembrane transporter activity | 16 | 1.48e-07 |
| GO:0008509 | anion transmembrane transporter activity | 18 | 8.06e-15 |
| | | | *(more...)* |

Cellular Component (GO)

| pathway ID | pathway description | count in network | false discovery rate |
|---|---|---|---|
| GO:0022626 | cytosolic ribosome | 22 | 5.51e-19 |
| GO:0044445 | cytosolic part | 24 | 3.47e-15 |
| GO:0044391 | ribosomal subunit | 21 | 1.86e-14 |
| GO:0044422 | organelle part | 160 | 2.3e-13 |
| GO:0022625 | cytosolic larg ribosomal subunit | 14 | 2.95e-13 |
| | | | *(more...)* |

Figure 8
to be continued

KEGG Pathways

| pathway ID | pathway description | count in network | false discovery rate |
|---|---|---|---|
| 03010 | Ribosome | 21 | 9.76e-15 |
| 04114 | Oocyte meiosis | 15 | 1.41e-09 |
| 04110 | Cell cycle | 15 | 7.54e-09 |
| 05203 | Viral carcinogenesis | 13 | 7.23e-05 |
| 05034 | Alcoholism | 11 | 0.000135 |
| | | | (more...) |

PFAM Protein Domains

| pathway ID | pathway description | count in network | false discovery rate |
|---|---|---|---|
| PF00125 | Core Histone H2A/H2B/H3/H4 | 12 | 3.11e-08 |
| PF00244 | 14-3-3 protein | 6 | 5.53e-08 |
| PF00149 | Calcineurin-like phosphoesterase | 4 | 0.0372 |
| PF07690 | Major Facilitator Superfamily | 4 | 0.0372 |
| PF00481 | Protein phosphatase 2C | 3 | 0.0442 |
| | | | (more...) |

INTERPRO Protein Domains and Features

| pathway ID | pathway description | count in network | false discovery rate |
|---|---|---|---|
| IPR002119 | Histone H2A | 12 | 1.9e-13 |
| IPR007125 | Histone H2A/H2B/H3 | 12 | 3.32e-08 |
| IPR000308 | 14-3-3 protein | 6 | 4.73e-08 |
| IPR023409 | 14-3-3 protein, conserved site | 6 | 4.73e-08 |
| IPR023410 | 14-3-3 domain | 6 | 4.73e-08 |
| | | | (more...) |

Figure 8
Continued

Figure 13
Androgen dependent PC cell line LNCaP
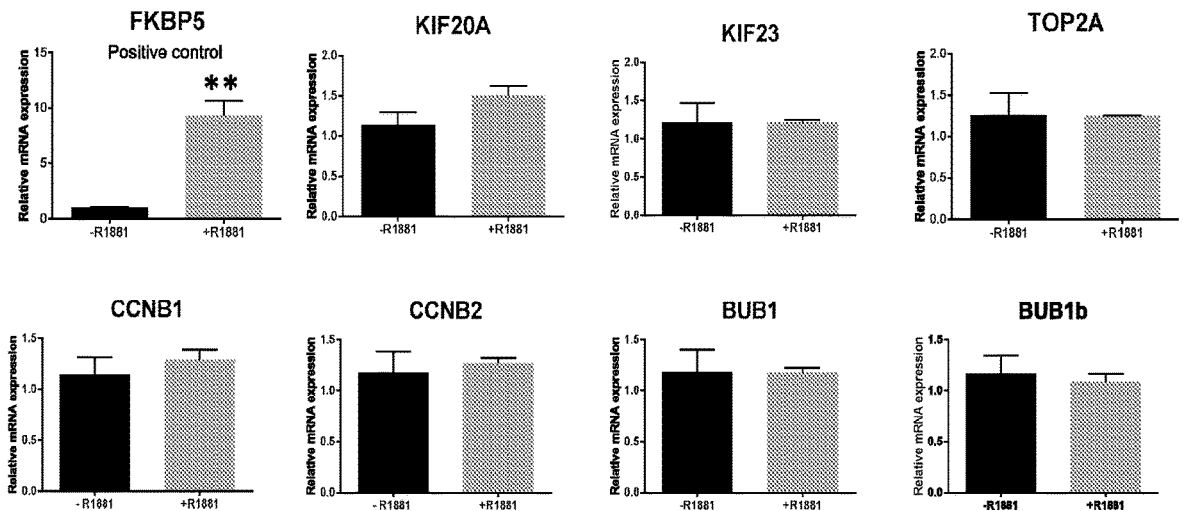
CRPC cell line 22Rv1
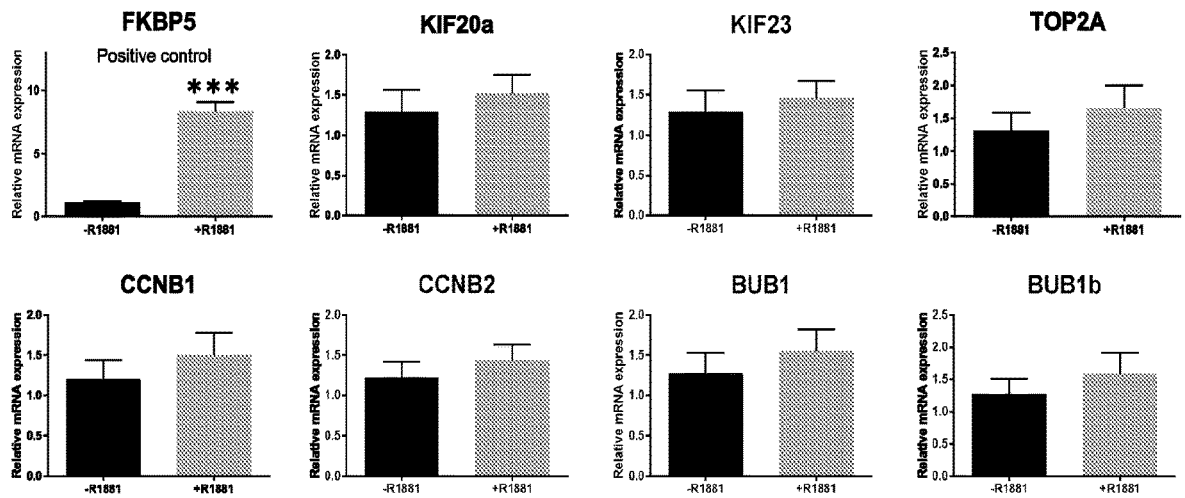

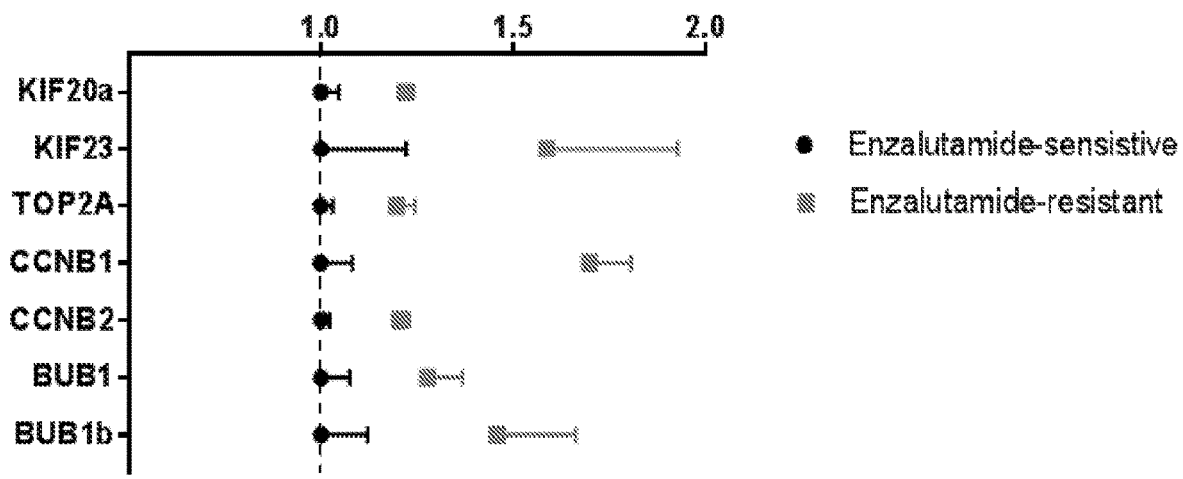
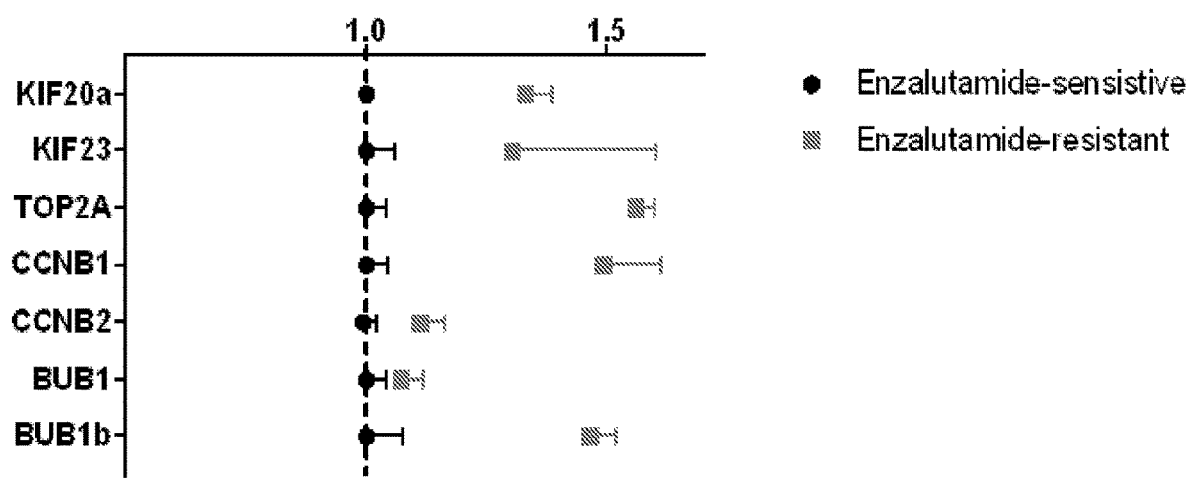
Figure 18

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 1
atggaagtgc agttagggct                                           20

<210> SEQ ID NO 2
<211> LENGTH: 21
<212> TYPE: DNA
<213> ORGANISM: Artificial Sequence
<220> FEATURE:
<223> OTHER INFORMATION: Synthetic Primer

<400> SEQUENCE: 2
tcagggtctg gtcattttga g                                         21

BIOMARKERS INDICATIVE OF PROSTATE CANCER AND TREATMENT THEREOF

STATEMENT ON U.S. GOVERNMENT INTEREST

This invention was made with government support under grant number CA132200 awarded by the National Institutes of Health. The government has certain rights in the invention.

FIELD OF THE INVENTION

The present application relates to diagnosis, characterization, and treatment of prostate cancer.

INCORPORATION BY REFERENCE OF MATERIALS SUBMITTED ELECTRONICALLY

This application contains, as a separate part of the disclosure, a Sequence Listing in computer readable form (Filename: 51882A Seqlisting.txt; Size: 648 bytes; Created: Apr. 4, 2018), which is incorporated by reference in its entirety.

BACKGROUND

Prostate cancer (PC) is a disease of increasing significance worldwide. With an estimated of over 26,000 deaths per year in the US, PC is the second-leading cause of cancer related death in men (Siegel et al., 2016). Androgen deprivation therapy (ADT) has been the gold standard treatment for non-organ confined PC, leading to tumor regression. However, PC inevitably recurs within 18 to 24 months (Cai et al., 2011). This rapidly progressing stage of the disease is known as castration resistant prostate cancer (CRPC) (Dehm & Tindall, 2006), for which treatment options are limited, and which inevitably results in death (Antonarakis et al., 2014). A major mechanism driving CRPC progression and therapeutic resistance is the presence of AR splice variants. AR variants that lack the carboxy-terminus and ligand binding domain (LBD), but retain the transactivating N-terminal domain (NTD) and DNA-binding domain (DBD) (Dehm et al., 2008). Constitutively active AR-V7 (also termed AR3 or AR1/2/3/CE3) is the most highly express AR splice variant in human specimens (Hornberg et al., 2011) and has been linked to poor prognosis, epithelial-mesenchymal transition (EMT) (Cottard et al., 2013; Kong et al., 2015), and resistance to current treatments (Qu et al., 2015; Karantanos et al., 2013; Mostaghel et al, 2011; Sun et al., 2010, Hornberg et al., 2011, Antonaraikis et al., 2014; Lokhandwala et al., 2016); making AR-V7 an attractive target for CRCP therapy. However, AR splice variants lack the AR LBD and have an intrinsic disorganized structure. Thus, designing high-affinity compounds that target other regions in the protein is a major challenge (Chan et al., 2015). There is an imperative need to identify novel proteins in PC that interact with AR-V7 and drive disease progression, which could serve as targets.

In the advanced stage of prostate cancer (PC), called castration-resistant prostate cancer (CRPC), C-terminal truncated, constitutively active androgen receptor (AR) splice variants (such as AR-V7) play key transcription-regulatory roles resulting in treatment resistance and disease progression. Designing high-affinity drugs to target the amino-terminus of AR and AR variants is a major challenge due to the intrinsic disorganized structure of this region. Thus there is an imperative need to identify novel AR-V7 hub genes that may serve as therapeutic targets in PC.

SUMMARY

In one aspect, the disclosure provides a method of decreasing proliferation of prostate cancer cells (e.g., castrate-resistant prostate cancer (CPRC) cells) comprising contacting the cells with doxorubicin (DOX) and a mitotic cyclin dependent kinase inhibitor in an amount effective to decrease proliferation of the cancer cells. In some embodiments, the CRPC cells are selected from the group consisting of 22Rv1 cells and C4-2B cells.

In another aspect, the disclosure provides a method of treating prostate cancer in a subject in need thereof comprising administering to the subject doxorubicin (DOX) and a mitotic cyclin dependent kinase inhibitor in amounts effective to treat prostate cancer in the subject. In some embodiments, the prostate cancer is castrate-resistant prostate cancer (CRPC). In some embodiments, the subject is resistant to treatment with enzalutamide.

In some embodiments, the mitotic cyclin dependent kinase inhibitor is selected from the group consisting of N9-isopropydolomoucine (N-9); olomoucine; purvalanol B (which is also known as Benzoic acid), 2-chloro-4-[[2-[[(1R)-1-(hydroxymethyl)-2-methylpropyl]amino]-9-(1-methyl-ethyl)-9H-purin-6-yl]amino]-(9C1); roscovitine; indirubin (which is also known as 2H-indol-2-one, 3-(1,3-dihydro-3-oxo-2H-indol-2-ylidene)-1,3-dihydro-(9C1)); kenpaullone (which is also known as indolo[3,2-d][1]benzazepin-6(5H)-one, 9-bromo-7,12-dihydro-(9C1)); purvalanol A (which is also known as 1-Butanol, 24[6-[(3-chlorophenyeamino]-9-(1-methylethyl)-9H-purin-2-yl]amino]-3-methyl-, (2R)-(9C1); and indirubin-3'-monooxime. In some embodiments, targets of a mitosis cyclin dependent kinase inhibitor include, but are not limited to, CDK, AHR, CDK1, CDK2, CDK5, CDK 4/6, GSK3beta and ERK. Compounds that target one or more of CDK, AHR, CDK1, CDK2, CDK5, CDK 4/6, GSK3beta and ERK are specifically contemplated. In some embodiments, the mitotic cyclin dependent kinase inhibitor is N-9.

In some or any embodiments, the amount of DOX administered to the subject is less than 2 mg/mL. In some or any embodiments, the amount of DOX administered to the subject ranges from about 50 ng/mL to about 500 ng/mL or about 500 ng/mL to about 1 mg/mL. In some or any embodiments, the amount of DOX administered to the subject is about 1 ng/mL, or about 2 ng/mL, or about 3 ng/mL, or about 4 ng/mL, or about 5 ng/mL, or about 6 ng/mL, or about 7 ng/mL, or about 8 ng/mL, or about 9 ng/mL, or about 10 ng/mL, or about 15 ng/mL, or about 20 ng/mL, or about 25 ng/mL, or about 30 ng/mL, or about 35 ng/mL, or about 40 ng/mL, or about 45 ng/mL, or about 50 ng/mL, or about 55 ng/mL, or about 60 ng/mL, or about 65 ng/mL, or about 70 ng/mL, or about 75 ng/mL, or about 80 ng/mL, or about 85 ng/mL, or about 90 ng/mL, or about 95 ng/mL, or about 100 ng/mL, or about 150 ng/mL, or about 200 ng/mL, or about 250 ng/mL, or about 300 ng/mL, or about 350 ng/mL, or about 400 ng/mL, or about 450 ng/mL, or about 500 ng/mL, or about 550 ng/mL, or about 600 ng/mL, or about 650 ng/mL, or about 700 ng/mL, or about 750 ng/mL, or about 800 ng/mL, or about 850 ng/mL, or about 900 ng/mL, or about 950 ng/mL, or about 1 mg/mL or about 1.5 mg/mL (or a range comprising any of the aforementioned values as endpoints).

In some or any embodiments, the amount of mitotic cyclin dependent kinase inhibitor (e.g., N-9) administered to the subject is less than 2 mg/mL. In some or any embodiments, the amount of mitotic cyclin dependent kinase inhibitor (e.g., N-9) administered to the subject ranges from about 50 ng/mL to about 500 ng/mL or about 500 ng/mL to about 1 mg/mL. In some or any embodiments, the amount of mitotic cyclin dependent kinase inhibitor (e.g., N-9) administered to the subject is about 1 ng/mL, or about 2 ng/mL, or about 3 ng/mL, or about 4 ng/mL, or about 5 ng/mL, or about 6 ng/mL, or about 7 ng/mL, or about 8 ng/mL, or about 9 ng/mL, or about 10 ng/mL, or about 15 ng/mL, or about 20 ng/mL, or about 25 ng/mL, or about 30 ng/mL, or about 35 ng/mL, or about 40 ng/mL, or about 45 ng/mL, or about 50 ng/mL, or about 55 ng/mL, or about 60 ng/mL, or about 65 ng/mL, or about 70 ng/mL, or about 75 ng/mL, or about 80 ng/mL, or about 85 ng/mL, or about 90 ng/mL, or about 95 ng/mL, or about 100 ng/mL, or about 150 ng/mL, or about 200 ng/mL, or about 250 ng/mL, or about 300 ng/mL, or about 350 ng/mL, or about 400 ng/mL, or about 450 ng/mL, or about 500 ng/mL, or about 550 ng/mL, or about 600 ng/mL, or about 650 ng/mL, or about 700 ng/mL, or about 750 ng/mL, or about 800 ng/mL, or about 850 ng/mL, or about 900 ng/mL, or about 950 ng/mL, or about 1 mg/mL or about 1.5 mg/mL (or a range comprising any of the aforementioned values as endpoints).

In some or any embodiments, the DOX and the mitotic cyclic kinase dependent inhibitor (e.g., N-9) are administered to the subject in separate compositions. In some or any embodiments, the DOX and the mitotic cyclic kinase dependent inhibitor (e.g., N-9) are administered in the same composition. In some or any embodiments, the DOX is administered within 24 hours of the mitotic cyclic kinase dependent inhibitor (e.g., N-9).

In some or any embodiments, the methods described herein further comprise administering a further therapeutic agent selected from the group consisting of an androgen receptor antagonist, an inhibitor of androgen synthesis, a gonadotropin-releasing hormone (GnRH) agonist and a GnRH antagonist to the subject.

In another aspect, the disclosure provides a method of treating prostate cancer in a subject in need thereof comprising (a) identifying elevated levels of kinesin family-member 20A (KIF20A), kinesin family-member 23 (KIF23), topoisomerase DNA II alpha (TOP2A), cyclin B1 (CCNB1) cyclin B2 (CCNB2), mitotic checkpoint serine/threonine kinase (B UB1) and mitotic checkpoint serine/threonine kinase B (BUB 1b) in a tumor sample from the subject relative to a reference standard; and (b) administering doxorubicin (DOX) and mitotic cyclic kinase dependent inhibitor (e.g., N-9) in amounts effective to treat prostate cancer in the subject.

BRIEF DESCRIPTION OF THE FIGURES

FIG. 1A: Module-trait relationships were established by WGCNA using eight independent microarray analyses comprising 375 human prostate samples. Gene modules (y axis) are denoted by an arbitrary color name. Bins show the Pearson correlation value between gene expression levels of each module within the noted phenotype/disease stage (x axis) and p values. A value of 1 (dark gray) quantifies the strongest positive correlation (genes are upregulated), −1 (light gray) the strongest negative correlation (genes are downregulated), and 0 (white) no correlation. FIG. 1B: Microarray analysis was performed following doxycycline-regulated specific AR-V7 depletion (using a tet-p1K0 backbone) in 22Rv1 PC cells compared to doxycycline-treated shGFP controls. The genes that were significantly regulated by shAR-V7 (in either direction, p value<0.05) were distributed among the gene modules defined by WGCNA in panel A. Upregulated genes (dark gray) are those in which expression decreased following AR-V7 depletion and conversely downregulated genes (light gray) are those that increased following AR-V7 depletion. The green module is identified as the top square marked wrth a triangle (with the bottom, longer bar in that module showing a down-regulation with AR-V7 KD. FIG. 1C: AR-V7 human functional interactome was generated using SGA screening in the yeast S. pombe, combined with STRING data to map protein-protein interactions, followed by the identification of the human orthologs. The colors denote the different types of genetic interactions: black are genes that when deleted in yeast and crossed with AR-V7-expressing yeast were synthetic lethal while dark gray denotes genes that caused a growth suppression. White designates yeast essential genes (that were not present in the yeast deletion library), but were added into the network based on the criteria that they are known to physically interact with at least two of the black or dark gray genes. Light gray are a combination of essential and nonessential genes identifying the same human protein. FIG. 1D: Table summarizing the seven PC hub genes identified by the system-level analyses. Green module is identified in FIG. 1A as the top of the three rectangles maked with a triangle. FIG. 1E: Network interactions of the seven genes with the 50 most frequently altered neighbor genes, were mapped using cbioportal.org. The type of gene to gene interactions are: controls state change of, controls expression of, in complex with.

FIGS. 2A and 2B: Elevated expression of the seven gene set is associated with higher levels of AR-V7, and serves as a prognostic biomarker for Disease Free-Survival (DFS) and Chances of Death in PC patients. FIG. 2A: Hornberg et al., 2011 gene expression profiling array data was analyzed to determine the expression levels of the seven genes in human PC bone metastases, grouped by their relative levels of AR-VS, mainly AR-V7. (High-levels of AR-V7 (top quartile) or lower levels of AR-V7 (quartiles 1-3). Data are plotted as the mean±s.e.m. Non-parametric Mann-Whitney test was performed (two-tailed). Note that BUB 1b expression was not measured in these microarrays. ** Significant at a p value<0.05; * significant at a p value<0.1. N (AR-V7 low)=20; N (AR-V7 high)=10. FIG. 2B: The Kaplan-Meier curves for Disease-Free Survival (DFS) and overall survival were built using the Prostate Adenocarcinoma TCGA dataset (465 samples) (upper graphs). The top curves denote cases with normal expression of the gene set, and bottom curves represents cases where the mRNA levels of the seven genes were upregulated (z-score threshold 1.96). For DFS: p-value=0.0009; for death: p-value=0.026. An independent dataset was analyzed (Prostate Adenocarcinoma MSKCC, Cancer Cell 2010, 123 samples) (lower graphs). The top curves denote cases with normal expression of the gene set, and bottom curves represent cases where the mRNA levels of at least five genes of the gene set were upregulated (z-score threshold 1.96). For DFS: p-value=0.0007; for death: p-value=0.00546.

FIG. 3A Cell proliferation was examined in the CRPC cell line 22Rv1 following individual depletion of mRNAs for the seven genes or shGFP controls, using shRNA against the coding region for each gene (shRNA #2). Cell number was measured using a non-perturbing nuclear restricted dye and quantified after 72 hours using Incucyte Zoom System. Data shown are mean±s.e.m. of 8 to 12 replicates normalized to their shGFP control. Kruskal-Wallis test (p value<0.0001, two-tailed) and Dunn's multiple comparisons test were performed. FIG. 3B: Representative images of 22Rv 1 stably depleted of BUB 1b, or control (shGFP) are shown. FIG. 3C: 22Rv1 stably depleted of each of the seven genes were transfected with a dual plasmid luciferase reporter system which quantifies AR activity and basal transcription. The assay was conducted in 2% CSS to measure AR ligand-independent transcriptional activity. Data represent two independent experiments performed in triplicate, showing the mean±s.e.m., and normalized to their shGFP controls. The expression of FKBP5 (FIG. 3D) and UBE2C (FIG. 3E) determined by RT-qPCR analysis and normalized to GAPDH mRNA levels was examined in 22Rv1 cells stably expressing shRNA for each of the seven genes. Cells were cultured in 2% CSS. Data represent two independent experiments performed in duplicate or triplicate, showing the mean±s.e.m., and normalized to their shGFP controls. Kruskal-Wallis test (p value<0.0001, two-tailed) and Dunn's multiple comparisons test were performed. * Significant at a p value<0.05, ** p value<0.001.

FIG. 4A: The CRPC cell line 22Rv I was cultured in 2% CSS media and was treated for 72 hours with vehicle (DMSO), doxorubicin (DOX), N9-isopropylolomoucine (N-9), or the combination of DOX and N-9 at different concentrations. Cell confluence was monitored using Incucyte Zoom System and the experiments were done with eight replicates each. The data were analyzed using Compusyn software, and a normalized isobologram was built. The table shows the Combination Index (CI) for the different drug combinations. CI=1 represents additivity, CI<1 synergism, and CI>1 antagonistic effects. FIG. 4B: The non-tumorigenic prostate epithelial cell line RWPE1, the AR-null PC cell line PC3, and the CRPC cell lines C4-2B and 22Rv1 were treated for 72 hours with vehicle (DMSO), DOX (100 ng/mL [184 nM]), N-9 (200 ng/mL [613 nM]), or the combination of DOX (100 ng/mL [184 nM]) and N-9 (200 ng/mL [613 nM]). C4-2B and 22Rv1 cells were kept in 10% CSS media. Cell confluence was monitored using the Incucyte Zoom System. Data represent two independent experiments, with four to six replicates each, showing the mean±s.e.m., and normalized to vehicle controls (Kruskal-Wallis test, P value<0.0001, two-tailed). *Significant at a p value<0.05,  p value<0.01, * p value<0.001. FIG. 4C: The non-tumorigenic prostate cell line RWPE-1 and the CRPC cell line 22Rv1 were treated for 72 hours with vehicle (DMSO) or the combination of DOX and N-9 at 100 ng/mL and N-9 200 ng/mL, respectively. Cell confluence was monitored using the Incucyte Zoom System.

FIG. 5A-5E: Meta-analysis of human gene expression profiling arrays identifies gene modules that correlate with prostate cancer progression. The tables summarize the eight independent microarrays used for the WGCNA analysis (FIG. 5A), comprising 375 human prostate samples, and the different prostate phenotypes (FIG. 5B). FIG. 5C: The schematics depict the underlying concept of WGCNA in which gene modules are defined by identifying those genes whose expression changes similarly across different patients. FIG. 5D: Heat map depicts gene expression levels of Green, Magenta and Yellow modules, which significantly correlate with disease progression, and their relationships to phenotype/disease stage from WGCNA analysis. FIG. 5E: Results from pathway enrichment analysis of the green module is shown.

FIG. 6A: 22Rv1 cells stably expressing tet-shAR-V7 were grown in 5% CSS±doxycycline for 72 hours. Equivalent amounts of total cellular protein were immunoblotted for N-terminal AR and actin. FIG. 6B: Microarray analysis was performed in 22Rv1 PC cells in doxycycline-treated shGFP controls. The genes that were significantly regulated by shGFP (in either direction, p value<0.05) were distributed among the gene modules defined by WGCNA in FIG. 1A. The green module is identified as the top square marked wrth a triangle (with the bottom, longer bar in that module showing a down-regulation with GFP KD). Upregulated genes are those in which expression decreased following GFP depletion. Conversely. downregulated genes are those that increased following GFP depletion.

FIG. 8: Network analysis of AR-V7 interactome was obtained using STRING of hits identified by SGA screening.

FIG. 13: None of the seven genes are regulated by ligand-activated full length AR. LNCaP and 22Rv1 cells were seeded and 24 hours later were rinsed twice with PBS and incubated in serum free media for one hour. The cells were then incubated in media containing vehicle or R1881 (0.1 nM) for 16 hours prior to RNA extraction and qPCR analysis. FKBP5 was used as a positive control. Data represent one or two independent experiments, performed in biological triplicates, showing the mean±s.e.m., and normalized to vehicle control. Significant at a p value,  p value<0.01, * p value<0.001.

FIG. 18: Higher expression levels of the seven gene set are associated with enzalutamide resistance. Microarray analysis from the GSE78201 dataset (Kregel et al., 2016) was analyzed, where the androgen-dependent cell lines VCaP and LNCaP were treated with enzalutamide for 48 hours or for over six months, until they acquired enzalutamide resistance. Data show mean±s.e.m (N=3-4 per group), and were normalized to the expression levels of each gene upon 48-hour enzalutamide treatment (enzalutamide-sensitive).

DETAILED DESCRIPTION

Figure 1A:
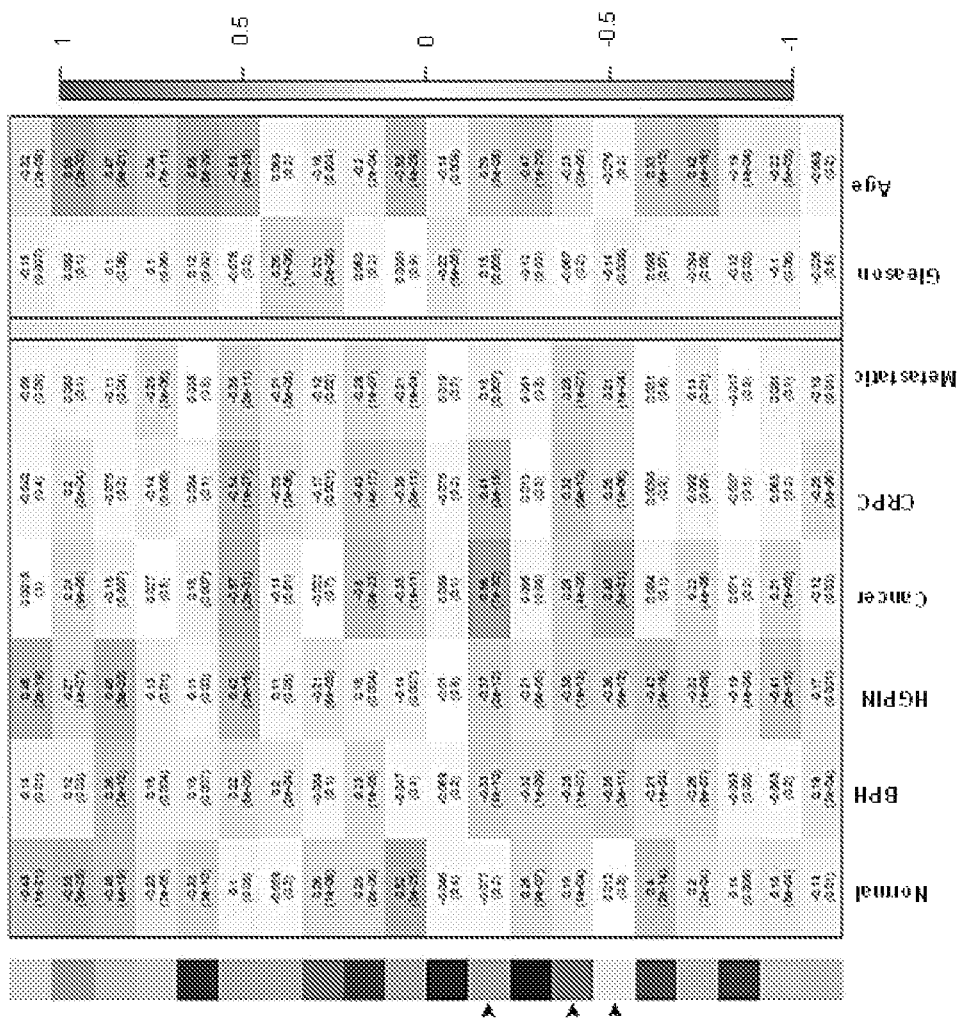
FIGS. 1A-1E: Multi-faceted system-level analyses identifies seven prostate cancer hub genes.

Unbiased high-throughput approaches provide a complete landscape view of the massive genetic and transcriptomics changes that occur in and potentially drive cancer, allowing also the identification of novel markers and targets. Computational system-level analysis combined with experimental approaches provide a powerful tool which allows us to understand the gene network structures and dynamics involving these targets.

The Examples provided herein describe extensive and highly robust gene expression meta-analysis on prostate cancer (PC) patient samples. Gene modules were defined that correlated with disease progression using a powerful systems biology approach termed Weighted Gene-Co-expression Network Analysis (WGCNA). Further, the AR-V7 interactome was mapped for the first time using a novel high-throughput synthetic genetic array screening in yeast, known as Yeast Augmented Network Analysis (YANA). YANA was performed by crossing a yeast strain expressing AR-V7 with a large collection of yeast strains lacking non-essential genes and identifying genes that caused a change in yeast growth (fitness). Human orthologs of the identified yeast genes were used to build an AR-V7 functional gene network. Finally, the results from the independent system-level analyses were combined with experimental data to identify hub genes that are upregulated in PC patients, regulated by AR-V7, and also functionally interact with AR-V7. The identified genes not only include select genes previously linked to PC, such as members of the cyclin and topoisomerase families (CCNB1 and TOP2A), but also genes that have not been previously linked to AR-V7 activity or PC progression (KIF20A, KIF23, CCNB2, BUB1, BUB1B). Individual depletion of these genes lead to decreased CRPC cell proliferation. Moreover, the gene expression signature identified in the Examples predicted a higher risk of PC recurrence after primary treatment in patients.

The present disclosure also demonstrates the surprisingly synergistic effect of doxorubicin (DOX) and a mitotic cyclin dependent kinase inhibitor (e.g., N9-isopropylolomoucine (N-9)) in decreasing the proliferation of prostate cancer cells (e.g., castrate-resistant prostate cancer (CRPC) cells). As shown in Example 3, when DOX and N9 were administered individually, these compounds had no significant effect on the proliferation of the prostate cancer cell lines tested. However, the combination of both compounds synergistically inhibited the proliferation of CRPC cell lines 22Rv1 and C4-2B. Thus, the disclosure provides a method for decreasing the proliferation of prostate cancer cells by administering a DOX/mitotic cyclin dependent kinase inhibitor therapy in an amount effective to decrease proliferation of the cells.

The terms "DOX/mitotic cyclin dependent kinase inhibitor therapy" and "combination of DOX and a mitotic cyclin dependent kinase inhibitor" refer to the administration of DOX and a mitotic cyclin dependent kinase inhibitor (e.g., N-9) for the treatment of prostate cancer, and encompasses compositions comprising both DOX and a mitotic cyclin dependent kinase inhibitor (e.g., N-9) as well as a composition comprising DOX and a composition comprising a mitotic cyclin dependent kinase inhibitor (e.g., N-9). Optionally, both compositions are administered to the subject at the same time (or within 24 hours of the first composition being administered). For example, in some embodiments, a first composition comprising DOX is administered to the subject and a second composition comprising a mitotic cyclin dependent kinase inhibitor (e.g., N-9) is administered to the subject simultaneously. In some embodiments, a first composition comprising DOX is administered to the subject and a second composition comprising a mitotic cyclin dependent kinase inhibitor (e.g., N-9) is administered about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours or about 24 hours after the first composition is administered. In some embodiments, a first composition comprising a mitotic cyclin dependent kinase inhibitor (e.g., N-9) is administered to the subject and a second composition comprising DOX is administered about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours or about 24 hours after the first composition is administered.

In some or any embodiments, the prostate cancer cells are castrate-resistant prostate cancer cells (e.g., 22Rv1 and/or C4-2B cells).

In various aspects, the method comprises decreasing the proliferation of prostate cancer cells in vivo. The disclosure also provides a method of treating prostate cancer in a subject in need thereof comprising administering to the subject doxorubicin (DOX) and a mitotic cyclin dependent kinase inhibitor (e.g., N-9) in an amount effective to treat prostate cancer in the subject. In some or any embodiments, the prostate cancer is castrate-resistant prostate cancer.

In some or any embodiments, the subject is resistant to treatment with enzalutamide.

In some or any embodiments, the disclosure provides a method to identify subjects having an aggressive form of prostate cancer, the method comprising the step of identifying elevated levels of kinesin family-member 20A (KIF20A), kinesin family-member 23 (KIF23), topoisomerase DNA II alpha (TOP2A), cyclin B1 (CCNB1) cyclin B2 (CCNB2), mitotic checkpoint serine/threonine kinase (BUB1) and mitotic checkpoint serine/threonine kinase B (BUB lb) in a tumor sample from the subject relative to a reference standard, wherein the elevated levels of kinesin family-member 20A (KIF20A), kinesin family-member 23 (KIF23), topoisomerase DNA II alpha (TOP2A), cyclin B1 (CCNB1) cyclin B2 (CCNB2), mitotic checkpoint serine/threonine kinase (BUB1) and mitotic checkpoint serine/threonine kinase B (BUB lb) in the sample identifies the subject as likely having an aggressive form of prostate cancer. In this regard, subjects identified as having elevated levels of KIF20A, KIF23, TOP2A, CCNB1, CCNB2, BUB and BUBlb relative to a reference standard would be candidates for surgery and/or radiation rather than active surveillance.

In some or any embodiments, the disclosure also provides a method to identify subjects likely to relapse, the method comprising the step of identifying elevated levels of kinesin family-member 20A (KIF20A), kinesin family-member 23 (KIF23), topoisomerase DNA II alpha (TOP2A), cyclin B1 (CCNB1) cyclin B2 (CCNB2), mitotic checkpoint serine/threonine kinase (BUB1) and mitotic checkpoint serine/threonine kinase B (BUB1b) in a tumor sample from the subject relative to a reference standard, wherein the elevated levels of kinesin family-member 20A (KIF20A), kinesin family-member 23 (KIF23), topoisomerase DNA II alpha (TOP2A), cyclin B1 (CCNB1) cyclin B2 (CCNB2), mitotic checkpoint serine/threonine kinase (BUB1) and mitotic checkpoint serine/threonine kinase B (BUB lb) in the sample identifies the subject as likely having an aggressive form of prostate cancer.

In another aspect, the disclosure provides a method of treatment comprising the step of identifying elevated levels of kinesin family-member 20A (KIF20A), kinesin family-member 23 (KIF23), topoisomerase DNA II alpha (TOP2A), cyclin B1 (CCNB1) cyclin B2 (CCNB2), mitotic checkpoint serine/threonine kinase (BUB1) and mitotic checkpoint serine/threonine kinase B (BUB lb) in a tumor sample from the subject relative to a reference standard prior to treatment (e.g., with DOX/N-9 therapy). Methods of determining gene expression levels in a sample are known in the art and are also described herein in Examples 1 and 2.

The measuring of KIF20A, KIF23, TOP2A, CCBN1, CCNB2, BUB1 and BUB lb in the methods described herein can occur after a cancer diagnosis has been made and prior to in initiation of treatment. In some embodiments, the measuring of KIF20A, KIF23, TOP2A, CCBN1, CCNB2, BUB1 and BUB lb occurs after a cancer has become resistant to a treatment (e.g., chemotherapy). These embodiments are not mutually exclusive. A subject undergoing cancer therapy can be monitored for KIF20A, KIF23, TOP2A, CCBN1, CCNB2, BUB1 and BUB1b expression to identify a time point at which the gene expression becomes elevated. In some embodiments, the subject is then administered DOX and a mitotic cyclin dependent kinase inhibitor (e.g., N-9) as described herein in various aspects of the method.

To assess the relative level of KIF20A, KIF23, TOP2A, CCBN1, CCNB2, BUB1 and BUB1b expression, the level of expression in a cancer tissue sample can be subjected to one or more comparisons (e.g., adjacent benign prostate tissue). In general, it can be compared to: (a) gene expression level(s) in normal tissue from the organ in which the cancer originated; (b) gene expression levels in a collection of comparable cancer tissue samples; (c) gene expression level in a collection of normal tissue samples; or (d) gene expression level in an arbitrary standard. In some embodiments, the screening methods described herein comprise comparing the expression of KIF20A, KIF23, TOP2A, CCBN1, CCNB2, BUB1 and BUB1b in a tumor sample from the subject to the level of gene expression in healthy tissue of the same type as the tumor, wherein elevated gene expression in the tumor to compared to the healthy tissue identifies the subject as a subject for whom DOX/mitotic cyclin dependent kinase inhibitor therapy will have efficacy.

The identifying step of the methods described herein optionally comprises comparing the measurement of KIF20A, KIF23, TOP2A, CCBN1, CCNB2, BUB1 and BUB1b expression to a reference measurement of KIF20A, KIF23, TOP2A, CCBN1, CCNB2, BUB1 and BUB 1b, and scoring the measurement from the sample as elevated based on statistical analysis or a ratio relative to the reference measurement. In some embodiments, the reference measurement comprises at least one of the following (a) a measurement of KIF20A, KIF23, TOP2A, CCBN1, CCNB2, BUB1 and BUB1b expression from healthy tissue of the subject of the same tissue type as the sample; (b) a database containing multiple KIF20A, KIF23, TOP2A, CCBN1, CCNB2, BUB1 and BUB1b expression measurements from healthy or cancerous tissues from other subjects; or (c) a reference value calculated from multiple KIF20A, KIF23, TOP2A, CCBN1, CCNB2, BUB1 and BUB1b expression measurements from healthy or cancerous tissues from other subjects, optionally further including statistical distribution information for the multiple measurements, such as standard deviation.

The methods described herein may optionally comprise the step of prescribing for or administering to the subject identified as having elevated KIF20A, KIF23, TOP2A, CCBN1, CCNB2, BUB1 and BUB1b expression in the biological sample a combination of DOX and a mitotic cyclin dependent kinase inhibitor (e.g., N-9). In some embodiments, the DOX/mitotic cyclin dependent kinase inhibitor therapy is prescribed for men whose cancer has recurred after newer generation androgen deprivation therapies (e.g., enzalutamide and abiterone). By "prescribing" is meant providing an order or authorization for the therapy, which may be dispensed to the subject for self-administration and/or administered by a medical professional that is difference from the prescribing professional.

The methods described herein may optionally comprise the step of identifying a subject as not being a candidate for treatment with enzalutamide, if the subject has elevated KIF20A, KIF23, TOP2A, CCBN1, CCNB2, BUB1 and BUB 1b expression in the biological sample from the subject As demonstrated in Example 3, prostate tumor cells having elevated expression levels of KIF20A, KIF23, TOP2A, CCBN1, CCNB2, BUB1 and BUB 1b are resistant to enzalutamide therapy.

Combination Therapy

Combination therapy (or "co-therapy") includes the DOX/N-9 therapy described herein and another agent as part of a treatment regimen intended to provide a beneficial effect from the combined action of these therapeutic agents.

Additional therapeutic agents or therapies contemplated for use with the DOX/mitotic cyclin dependent kinase inhibitor therapy described herein include, but are not limited to, androgen deprivation therapy, a chemotherapeutic agent, a radiotherapeutic agent, an immunotherapeutic agent, an inhibitor of cellular proliferation, a regulator of programmed cell death, surgery and other agents.

A. Androgen Deprivation Therapy

In some embodiments, androgen deprivation therapy is administered to the subject in combination with the DOX/ mitotic cyclin dependent kinase inhibitor therapy. Androgen deprivation therapy comprises the administration of an inhibitor of androgen synthesis to the subject, administration of an androgen receptor antagonist to the subject, administration of a gonadotropin-releasing hormone (GnRH) agonist, administration of a GnRH antagonist or a combination thereof.

In some embodiments, the methods described herein further comprise administering an androgen receptor antagonist to the subject. Exemplary androgen receptor antagonists include, but are not limited to, Enzalutamide, Bicalutamide, Ostarine, Flutamide, Cyproterone acetate, Gugguisterone, Nilutamide, PF998245, (R)-Bicalutamide, and 1,1-Dichloro-2,2-bis(4-chlorophenyl)ethene, and apalutamide (ARN-509).

In some embodiments, the methods described herein further comprise administering an inhibitor of androgen synthesis to the subject. An exemplary inhibitor of androgen synthesis is Abiraterone acetate.

In some embodiments, the methods described herein further comprise administering a GnRH agonist to the subject. Exemplary GnRH agonists include, but are not limited to, leuprolide, buserelin, histrelin, goserelin and deslorelin.

In some embodiments, the methods described herein further comprise administering a GnRH antagonist to the subject. Exemplary GnRH antagonists include, but are not limited to, cetrorelix, ganirelix, abarelix and degarelix.

B. Chemotherapeutic Agents

In some embodiments, chemotherapy may be administered, optionally in regular cycles. Standard of care chemotherapeutic regimens for patients with prostate cancer include, but are not limited to Docetazel, Cabazitaxel, Mitoxantrone, Estramustine, Doxorubicin, Etoposide, Vinblastine, Paclitaxel, Carboplatin and Vinorelbine. In some embodiments, docetaxel in combination with predisone is administered in combination with the DOX/mitotic cyclin dependent kinase inhibitor therapy described herein.

Chemotherapeutic agents contemplated for use with the methods described herein, include, but are not limited, to erlotinib (TARCEVAO, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine, dichloroplatinum(II), CAS No. 15663-27-1), carboplatin (CAS No. 41575-94-4), paclitaxel (TAXOL®, Bristol-Myers Squibb Oncology, Princeton, N.J.), bevacizumab (AVASTIN®, Genentech), trastuzumab (HERCEPTIN®, Genentech), pertuzumab (OMNITARGO, rhuMab 2C4, Genentech), temozolomide (4-methyl-5-oxo-2,3,4,6,8-pentazabicyclo[4.3.0]nona-2,7,9-triene-9-carboxamide, CAS No. 85622-93-1, TEMODARO, TEMODALO, Schering Plough), tamoxifen ((Z)-2-[4-(1,2-diphenylbut-1-enyl)phenoxy]-N,N-dimethyl-ethanam-ine, NOLVADEXO, ISTUBALO, VALODEX®), doxorubicin (ADRIAMYCINO), Akti-1/2, HPPD, rapamycin, and lapatinib (TYKERBO, Glaxo SmithKline), oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC 0, Novartis), XL-518 (MEK inhibitor, Exelixis, WO 2007/044515), ARRY-886 (MEK inhibitor, AZD6244, Array Bio-Pharma, Astra Zeneca), SF-1126 (PI3K inhibitor, Semafore Pharmaceuticals), BEZ-235 (PI3K inhibitor, Novartis), XL-147 (PI3K inhibitor, Exelixis), ABT-869 (multi-targeted inhibitor of VEGF and PDGF family receptor tyrosine kinases, Abbott Laboratories and Genentech), ABT-263 (Bcl-2/Bcl-xL inhibitor, Abbott Laboratories and Genentech), PTK787/ZK 222584 (Novartis), fulvestrant (FASLODEXO, AstraZeneca), leucovorin (folinic acid), lonafarnib (SARASAR.TM., SCH 66336, Schering Plough), sorafenib (NEXAVARO, BAY43-9006, Bayer Labs), gefitinib (IRES SAO, AstraZeneca), irinotecan (CAMPTOSARO, CPT-11, Pfizer), tipifarnib (ZARNESTRA™., Johnson & Johnson), capecitabine (XELODAO, Roche), ABRAXANE™ (Cremophor-free), albumin-engineered nanoparticle formulations of paclitaxel (American Pharmaceutical Partners, Schaumberg, Ill.), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN®, NEOSAR®), alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone), a camptothecin (including the synthetic analog topotecan), bryostatin, callystatin, CC-1065 (including its adozelesin, carzelesin and bizelesin synthetic analogs); cryptophycins (particularly cryptophycin 1 and cryptophycin 8), dolastatin, duocarmycin (including the synthetic analogs, KW-2189 and CBI-TMI); eleutherobin, pancratistatin, a sarcodictyin; spongistatin, nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, calicheamicin gammaIl, calicheamicin omegaIl, dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitracrinc; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; ibandronate; CPT-11; topoisomerase inhibitor RFS 2000; difluoromethylornithine (DMFO); retinoids such as retinoic acid; and pharmaceutically acceptable salts, acids and derivatives of any of the above.

C. Radiation Therapy

Radiation and radiotherapeutic agents may also be used in accordance with the methods described herein. Radiation includes, e.g., X-rays, microwaves and UV-irradiation. Radiation may be applied directly to an area of interest by directed delivery of radioisotopes to tumor cells. It is most likely that all of these factors effect a broad range of damage on DNA, on the precursors of DNA, on the replication and repair of DNA, and/or on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

D. Immunotherapeutic Agents

Immunotherapeutics may also be employed for the treatment of cancer. Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Generally, the tumor cell must bear some marker that is amenable to targeting, i.e., is not present on the majority of other cells or is present in insufficient amounts on non-target cells to render it unsuitable for selective delivery or binding to target cells. Many tumor markers exist and any of these may be suitable for targeting in the context of the present invention. Exemplary markers expressed in prostate tissues include, but are not limited to, prostate-specific antigen (PSA), prostate-specific membrane antigen (PSMA), prostatic acid phosphatase (PAP), prostate stem cell antigen (PSCA), T cell receptor gamma alternate reading frame protein (TARP), transient receptor potential (trp)-p8 and six-transmembrane epithelial antigen of the prostate 1 (STEAP1).

E. Regulators of Programmed Cell Death

Apoptosis, or programmed cell death, is an essential process in cancer therapy (Kerr et al., 1972). The Bcl-2 family of proteins and ICE-like proteases have been demonstrated to be important regulators and effectors of apoptosis in other systems. The Bcl-2 protein, discovered in association with follicular lymphoma, plays a prominent role in controlling apoptosis and enhancing cell survival in response to diverse apoptotic stimuli (Bakhshi et al., 1985; Cleary and Sklar, 1985; Cleary et al., 1986; Tsujimoto et al., 1985; Tsujimoto and Croce, 1986). The evolutionarily conserved Bcl-2 protein now is recognized to be a member of a family of related proteins, which can be categorized as death agonists or death antagonists.

Members of the Bcl-2 that function to promote cell death such as, Bax, Bak, Bik, Bim, Bid, Bad and Harakiri, arc contemplated for use in combination the DOX/mitotic cyclin dependent kinase inhibitor therapy described herein.

F. Surgery

It is further contemplated that a surgical procedure may be employed. Approximately 60% of persons with cancer will undergo surgery of some type, which includes preventative, diagnostic or staging, curative and palliative surgery. Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the invention may be used in conjunction with removal of superficial cancers, precancers, or incidental amounts of normal tissue.

G. Other Agents

It is contemplated that other agents may be used in combination with the methods described herein to improve the therapeutic efficacy of treatment. These additional agents include immunomodulatory agents, agents that affect the upregulation of cell surface receptors and GAP junctions, cytostatic and differentiation agents, inhibitors of cell adhesion, or agents that increase the sensitivity of the hyperproliferative cells to apoptotic inducers. Immunomodulatory agents include tumor necrosis factor; interferon alpha, beta, and gamma; IL-2 and other cytokines; F42K and other cytokine analogs; or MIP-1, MIP-lbeta, MCP-1, RANTES, and other chemokines. It is further contemplated that the upregulation of cell surface receptors or their ligands such as Fas/Fas ligand, DR4 or DR5/TRAIL would potentiate the apoptotic inducing abilities of the present invention by establishment of an autocrine or paracrine effect on hyperproliferative cells. Increased intercellular signaling by elevating the number of GAP junctions would increase the anti-hyperproliferative effects on the neighboring hyperproliferative cell population. In other embodiments, cytostatic or differentiation agents can be used in combination with the invention to improve the anti-hyperproliferative efficacy of the treatments. Inhibitors of cell adhesion are also contemplated to improve the efficacy of treatment. Examples of cell adhesion inhibitors are focal adhesion kinase (FAKs) inhibitors and Lovastatin.

Pharmaceutical Composition, Dosage and Routes of Administration

Compositions comprising DOX and/or mitotic cyclin dependent kinase inhibitor (e.g., N-9) described herein are also provided. The compositions contain, for example, DOX and/or mitotic cyclin dependent kinase inhibitor (e.g., N-9) and, optionally, pharmaceutically acceptable carrier. The pharmaceutical compositions used in the foregoing methods preferably are sterile and contain the therapeutic for producing the desired response in a unit of weight or volume suitable for administration to a patient. The pharmaceutical compositions may contain suitable buffering agents, including: acetic acid in a salt; citric acid in a salt; boric acid in a salt; and phosphoric acid in a salt.

When administered, the therapeutic compositions are administered in pharmaceutically acceptable preparations. Such preparations may routinely contain pharmaceutically acceptable concentrations of salt, buffering agents, preservatives, compatible carriers, supplementary immune potentiating agents such as adjuvants and cytokines, and optionally other therapeutic agents.

As used herein, the term "pharmaceutically acceptable" means a non-toxic material that does not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art. The term denotes an organic or inorganic ingredient, natural or synthetic, with which the active ingredient is combined to facilitate the application.

The composition(s) comprising DOX and/or mitotic cyclin dependent kinase inhibitor (e.g., N-9) can be administered by any conventional route, including injection or by gradual infusion over time. The administration may, for example, be oral, intravenous, intratumoral, intraperitoneal, intramuscular, intracavity, subcutaneous, or transdermal.

The composition(s) comprising DOX and/or mitotic cyclin dependent kinase inhibitor (e.g., N-9) are administered in effective amounts. An "effective amount" with respect to the combination of DOX and mitotic cyclin dependent kinase inhibitor (e.g., N-9) according to the teachings herein is that amount of the combination of DOX and mitotic cyclin dependent kinase inhibitor (e.g., N-9) composition(s) that alone, or together with further doses, produces the desired response, e.g., treats prostate cancer or decreases the proliferation of prostate cancer cells. In some embodiments, the desired response is inhibiting the progression of the disease. This may involve slowing the progression of the disease temporarily, although more preferably, it involves halting the progression of the disease permanently. Disease progression and cancer cell death can be monitored by routine methods.

In various aspects, administration of the composition(s) of DOX and mitotic cyclin dependent kinase inhibitor (e.g., N-9) delays onset or prevents the onset of prostate cancer (e.g., recurrence of the prostate cancer following androgen deprivation). In various embodiments, administration of the DOX/mitotic cyclin dependent kinase inhibitor (e.g., N9) therapy mediates a reduction in tumor size, such as a reduction in primary tumor volume. Optionally, the method described herein reduces tumor size by at least 1%, 3%, 5%, 10% or more. Alternatively or in addition, the method described herein reduces tumor burden (by, for example, 1%, 3%, 5%, 10% or more); slows, delays, or prevents metastasis; results in a reduction in prostate specific antigen levels in the blood (by, for example, 1%, 3%, 5%, 10% or more); or improves prostate cancer grading used by clinicians (e.g., Gleason score). In various embodiments, the methods described herein decreases prostate cancer cell proliferation by at least 1%, 3%, 5%, 10% or more.

Amounts of DOX and mitotic cyclin dependent kinase inhibitor (e.g., N-9) will depend on the severity of the condition, the individual patient parameters including age, physical condition, size and weight, the duration of the treatment, the nature of concurrent therapy (if any), the specific route of administration and like factors within the knowledge and expertise of the health practitioner. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

A cycle may involve one dose, after which several days or weeks without treatment ensues for normal tissues to recover from the drug's side effects. Doses may be given several days in a row, or every other day for several days, followed by a period of rest. If more than one drug is used, the treatment plan will specify how often and exactly when each drug should be given. The number of cycles a person receives may be determined before treatment starts (based on the type and stage of cancer) or may be flexible, in order to take into account how quickly the tumor is shrinking. Certain serious side effects may also require doctors to adjust chemotherapy plans to allow the patient time to recover.

The doses of DOX and mitotic cyclin dependent kinase inhibitor (e.g., N-9) compositions administered to a subject can be chosen in accordance with different parameters, such as the mode of administration used. In the event that a response in a subject is insufficient at the initial doses applied, higher doses (or effectively higher doses by a different, more localized delivery route) may be employed to the extent that patient tolerance permits.

In general, doses of DOX and mitotic cyclin dependent kinase inhibitor (e.g., N-9) are each formulated and administered in doses between 1 ng/ml to about 1 mg/ml, according to any standard procedure in the art. In some or any embodiments, the amount of DOX administered to the subject (i.e., a dose) is less than 2 mg/mL. In some or any embodiments, the amount of DOX administered to the subject ranges from about 50 ng/mL to about 500 ng/mL or about 500 ng/mL to about 1 mg/mL. In some or any embodiments, the amount of DOX administered to the subject is about 1 ng/mL, or about 2 ng/mL, or about 3 ng/mL, or about 4 ng/mL, or about 5 ng/mL, or about 6 ng/mL, or about 7 ng/mL, or about 8 ng/mL, or about 9 ng/mL, or about 10 ng/mL, or about 15 ng/mL, or about 20 ng/mL, or about 25 ng/mL, or about 30 ng/mL, or about 35 ng/mL, or about 40 ng/mL, or about 45 ng/mL, or about 50 ng/mL, or about 55 ng/mL, or about 60 ng/mL, or about 65 ng/mL, or about 70 ng/mL, or about 75 ng/mL, or about 80 ng/mL, or about 85 ng/mL, or about 90 ng/mL, or about 95 ng/mL, or about 100 ng/mL, or about 150 ng/mL, or about 200 ng/mL, or about 250 ng/mL, or about 300 ng/mL, or about 350 ng/mL, or about 400 ng/mL, or about 450 ng/mL, or about 500 ng/mL, or about 550 ng/mL, or about 600 ng/mL, or about 650 ng/mL, or about 700 ng/mL, or about 750 ng/mL, or about 800 ng/mL, or about 850 ng/mL, or about 900 ng/mL, or about 950 ng/mL, or about 1 mg/mL or about 1.5 mg/mL (or a range comprising any of the aforementioned values as endpoints).

In some or any embodiments, the amount of mitotic cyclin dependent kinase inhibitor (e.g., N-9) administered to the subject is less than 2 mg/mL, In some or any embodiments, the amount of mitotic cyclin dependent kinase inhibitor (e.g., N-9) administered to the subject ranges from about 50 ng/mL to about 500 ng/mL or about 500 ng/mL to about 1 mg/mL. In some or any embodiments, the amount of mitotic cyclin dependent kinase inhibitor (e.g., N-9) administered to the subject is about 1 ng/mL, or about 2 ng/mL, or about 3 ng/mL, or about 4 ng/mL, or about 5 ng/mL, or about 6 ng/mL, or about 7 ng/mL, or about 8 ng/mL, or about 9 ng/mL, or about 10 ng/mL, or about 15 ng/mL, or about 20 ng/mL, or about 25 ng/mL, or about 30 ng/mL, or about 35 ng/mL, or about 40 ng/mL, or about 45 ng/mL, or about 50 ng/mL, or about 55 ng/mL, or about 60 ng/mL, or about 65 ng/mL, or about 70 ng/mL, or about 75 ng/mL, or about 80 ng/mL, or about 85 ng/mL, or about 90 ng/mL, or about 95 ng/mL, or about 100 ng/mL, or about 150 ng/mL, or about 200 ng/mL, or about 250 ng/mL, or about 300 ng/mL, or about 350 ng/mL, or about 400 ng/mL, or about 450 ng/mL, or about 500 ng/mL, or about 550 ng/mL, or about 600 ng/mL, or about 650 ng/mL, or about 700 ng/mL, or about 750 ng/mL, or about 800 ng/mL, or about 850 ng/mL, or about 900 ng/mL, or about 950 ng/mL, or about 1 mg/mL or about 1.5 mg/mL (or a range comprising any of the aforementioned values as endpoints).

Administration of DOX and mitotic cyclin dependent kinase inhibitor (e.g., N-9) compositions to mammals other than humans, e.g., for testing purposes or veterinary therapeutic purposes, is carried out under substantially the same conditions as described above.

The pharmaceutical compositions also may contain, optionally, suitable preservatives, such as benzalkonium chloride; chlorobutanol; parabens and thimerosal.

The pharmaceutical compositions may conveniently be presented in unit dosage form and may be prepared by any of the methods well-known in the art of pharmacy. All methods include the step of bringing the active agent into association with a carrier which constitutes one or more accessory ingredients. In general, the compositions are prepared by uniformly and intimately bringing the active compound into association with a liquid carrier, a finely divided solid carrier, or both, and then, if necessary, shaping the product.

All publications and patents mentioned herein are hereby incorporated by reference in their entirety as if each individual publication or patent was specifically and individually indicated to be incorporated by reference. In case of conflict, the present application, including any definitions herein, will control.

The invention may be more readily understood by reference to the following example, which are given to illustrate the invention and not in any way to limit its scope.

EXAMPLES

Materials and Methods

Microarray dataset preprocessing: Microarray data sets were selected for those that used the Affymetrix Human Genome U133 plus 2.0 array and had clinical metadata for each sample (Table 1). In total, 375 microarrays met our inclusion criteria. These represent 8 studies performed at different institutes. The arrays were assigned to one of the following groups: normal, benign hyperplasia, high-grade prostatic intraepithelial neoplasia (basement membrane intact) (HGPIN) or cancerous. The cancerous group contained nested subsets for CRPC and metastatic samples.

Microarray data were downloaded from the Gene Expression Omnibus (GEO, National Center for Biotechnology Information) or ArrayExpress (European Bioinformatics Institute), read into R, and preprocessed using the "Affy" package. Pre-processing was performed as previously described (Chandran et al., 2016). Briefly, the "expresso" function was used to preform MASS preprocessing on each array. The correlation of gene expression between samples was calculated, and samples with mean correlations more than two to three standard deviations below average were excluded. Filtered samples were combined, annotated and quantile normalized. Clinically relevant metadata was constructed from sample annotations.

Construction of Prostate Cancer Gene Co-expression Networks

The Weighted Gene Co-expression Network (WGCNA) package was used to construct consensus modules containing highly connected nodes present across different PC datasets (Langfelder & Horvath, 2008). Modules were constructed with a minimum module size of 30 genes, and highly similar modules were combined using a dissimilarity threshold of 0.25. The Pearson correlation was first calculated between gene pairs. A weighting parameter, 13, was applied to the correlation matrix; with 13 satisfying scale-free topology criteria (Bin & Steve, 2005; Chandran et al., 2016). The weighted correlation matrix was used to calculate a topological overlap matrix and node dissimilarity. Genes were hierarchically clustered using the distance measure, and dynamic tree-cutting algorithm was used to define modules (Bin & Steve, 2005; Zhang & Horvath, 2005).

The resulting modules represent sets of highly connect nodes across the PCa datasets. The first principle component of each module was correlated with the clinical data to identify module-disease state relationships. Gene ontology analysis was performed using the "GOenrichmentAnalysis" function of the "WGCNA" R package.

RNA-sequencing Data Acquisition and Differential Expression Analysis

Aligned read counts were downloaded from GEO into R. Differential gene expression analysis was carried out using the "edgeR" package. Differentially expressed genes were defined as those undergoing greater than 2-fold change with a corrected p-value≤0.05. Differentially expressed genes (DEGs) were compared for concordance between datasets. Additionally, genes undergoing differential expression were assessed as the percentage of genes within each module.

Microarray

Three independent 22Rv1 cell isolates were derived from tet-pLKO shGFP and tet-pLKO shAR-V7 stable transductants. Cells were grown in androgen depleted conditions (10% A CSS), plus or minus doxycycline for one to three days. Knockdown was evaluated via western blot from a parallel protein harvest. A short-term, doxycycline-inducible knockdown system was utilized. After 48 hours, RNA from the 12 samples was evaluated for RNA Integrity Number (RIN), gcRMA package was used for the analysis. Results were computed with a False Discovery Rate (FDR) of 5%. Analysis was performed by looking at mRNA changes induced upon doxycycline treatment. Of the 25,293 transcripts examined, 4,273 genes exhibited significant alteration in expression following AR-V7 depletion (p value<0.05). Genes whose expression levels were significantly regulated in the shGFP control upon doxycycline treatment (628) (compared to the non-induced control gene set) were removed from the list of potential AR-V7 regulated genes. This analysis identified 3,645 genes solely regulated following AR-V7 depletion (p value<0.05).

Yeast synthetic genetic array (SGA) and Yeast Augmented Network Anaysis (YANA)

To create the query strain AR-V7 was cloned into a pENTR/D-TOPO vector (Life Technologies, Cat. K2400-20) from pcDNA3.1 AR-V7 following the manufacturer's protocols. The following primers were used: forward primer: 5'-atggaagtgcagttagggct-3'(SEQ ID NO: 1); reverse primer: 5'-tcagggtctggtcattttgag-3'(SEQ ID NO: 2), and the genetic insertion was confirmed by sequencing (GENEWIZ). The AR-V7 gene was flipped into a destination vector using LR Gateway reactions, according to manufacturer's protocol, to create an N-terminal HA-tagged AR-V7 under the control of the nmtl promoter (LR Clonase II from Life Technologies, Cat. 11791020). This expression vector was then integrated into an h' leu1-32 ura4-D18Ade6-M210 S. pombe strain (PN572) to create a AR-V7 query strain (h' integrated pjk148-nmtl$^{3x}$-HA-ARV7-amtr$^{term}$. leu1-32 ura4-D18 Ade6-M210). Strains containing AR-V7 (query strain) were grown in PMG media (Sunrise Scientific, Cat. 2060) and expression of HA-tagged AR-V7 was induced by removing thiamine from the media after washing cells with sterile water. AR-V7-induced expression was confirmed by immunoblotting using an AR-V7 specific antibody (mouse monoclonal Precision antibody, Cat AG10008). Growth conditions and genetic manipulations were previously described (Moreno et al., 1991). The query strain was crossed to the S. pombe haploid deletion library (Bioneer, Version 3.0 equivalent), utilizing a modified S GA procedure (Dixon et al., 2008). This procedure is described in detailed in Wiley et al., 2014. Briefly, each cross was grown in 4 replicates under AR-V7-inducing (without thiamine) or AR-V7 non-inducing (with thiamine) conditions. Colony growth was monitored for three days utilizing a flatbed scanner; and plates were analyzed for "hits" (i.e. a strain with a deleted gene that when crossed to induced-AR-V7-expressing yeast causes growth defect or growth enhancement in comparison to the same deletion strain crossed to non-induced yeast). Essential genes are added back based on the criteria that they interact with at least two primary hits in a S. pombe protein network (STRING, high confidence of 0.7). Following, networks maps are generated to map protein-protein interaction of the identified "Hits" and the essential genes added back (using STRING, p value<0.05). Networks maps are generated in STRING at high confidence (0.7) using either experimental data (BIND, DIP, GRID, HPRD, IntAct, MINT, and PID) or experimental data and database data (Biocarta, BioCyc, GO, KEGG, and Reactome). Then, the genes in the network maps are converted into human orthologs using Homologene (http://www.ncbi.nih.gov/homologene; build 67), INPARANOID (http://inparanoid.sbc.su.se/cgi-bin/index.cgi), OrthoMCL(http://orthomcl.org/orthomcV; version 5) and Pombase (www.pombase.org; build 2013-11-11-v1).

Disease free survival (DFS) curves and gene co-occurrence in clinical samples DFS Kaplain-Meier curves were constructed using CBioportal for Cancer Genomics (www.cbioportal.org) with TCGA adenocarcinoma provisional dataset (n=499). The mRNA expression Z-score threshold was set to ±1.5, and the logrank Test P-Value was calculated comparing the curves of patient cases with or without alterations in the query genes. Co-occurrence of genes was analyzed in the human samples with a Fischer Exact Test, where a p value<0.05 denotes a significant association between the genes.

Cell culture and chemical reagents: The human PC cell line 22Rv1 (CRL-2505, batch 4484055) was obtained from American Type Culture Collection (Manassas, Va.) and cultured in RPMI-1640 (Cellgro by Mediatech, Inc.), supplemented with 100 IU/ml penicillin, 100 µg/ml streptomycin, 2mML-glutamine (Life Technologies, Inc.) and 10% fetal bovine serum (FBS) (Atlanta Biologicals) or charcoal-stripped serum (CSS). The human PC cell line C4-2B was a generous gift from Dr. Conor Lynch (Moffitt Cancer Center, Tampa, Fla.), and cells were cultured in DMEM (Cellgro by Mediatech, Inc.), under the same conditions as 22Rv1. R1881 (methyltrienolone) was purchased from PerkinElmer Life and Analytical Sciences (Boston, Mass.) and used at 1 nM. Cells transduced with the different pLK0.1 plasmids were selected using 2.5 µg/ml of puromycin for 3 days, and then kept at 400 ng/ml of puromycin.

Doxycycline was used at 100 ng/mL. Doxorubicin (DOX) (from Sigma-Aldrich, D1515) was dissolved in distilled water and used at 100 ng/mL. N9-Isopropylolomoucine (N-9) was purchased from Santa Cruz (CAS 158982-15-1), dissolved in DMSO, and used at 200 ng/mL. 22Rv1 and C4-2B cells were kept in their corresponding media with 10% CSS (androgen-depleted). For the experiments in which the effects of DOX and N-9 on cell proliferation were examined, those wells that at time zero had a cell confluence of the mean±1.5 times the standard deviation were excluded from analysis. The combination index (CI) was calculated using the software Compusyn, by Ting Chao-Chou and Nick Martin (http://www.combosyn.com/feature.html), based on Chou-Talalay's Combination Index Theorem (Chou & Talalay, 1984).

All cell lines were authenticated using STR (Genetica), and tested for *mycoplasma* contamination every 6 months using the *Mycoplasma* PCR Detection kit (Sigma, St. Louis, Mo.; MP0035-1KT). All cell lines used were negative for *mycoplasma*, bacteria and fungi contamination.

Plasmids and gene depletion: The MMTV and GRE luciferase plasmids were kindly provided by Dr. Mona Nemer (University of Ottawa, Canada). The pLKO.1 shGFP and tet-pLKO.1 shGFP were a generous gift from Dr. Priya Rai (University of Miami); and shAR-V7 from Dr. Yun Qiu (University of Maryland School of Medicine, Maryland). The following constructs were purchased from Sigma-Aldrich (first construct against 3'UTR, second construct against coding region):: pLKO.1 shKIF20A (TRCN0000290278, TRCN0000290348), pLKO.1 shKIF23 (TRCN0000296388, TRCN0000296327), pLKO.1 shTOP2A (TRCN000049278, TRCN000049279), pLKO.1 shCCNB1 (TRCN0000293917, TRCN000045291), pLKO.1 shCCNB2 (TRCN000045193, TRCN000045197), pLKO.1 shBUB1 (TRCN0000288618, TRCN0000288618), and pLKO.1 shBUB1B (TRCN0000197142, TRCN0000194741).

Reporter gene assays and transfections: A dual plasmid Mouse Mammary Tumor Virus (MMTV)-luciferase system was used, in which one plasmid encodes wild type MMTV promoter while the control plasmid lacks androgen/glucocorticoid response elements (AGRE). Non-AR driven transcriptional activity and transfection efficiency can be accounted for by utilizing the AGRE plasmid as a baseline control. Transfection was performed using Lipofectamine (Invitrogen Life Technologies) and PLUS reagent (Invitrogen Life Technologies), following manufacturer's instructions. 22Ry1 were plated at a density of $3.0 \times 10^5$ cells in 35-mm dishes 24 hours before transfection. Immediately before transfection, media were replaced with unsupplemented DMEM. After a 6-h incubation period, the media was removed and cells were kept in RPMI 1640 2% CSS. After 48 hours they were harvested, lysed, and assessed for luciferase activity using the Promega luciferase assay kit (Promega Corp.) and a luminometer.

Cell proliferation: For growth assay, cells were plated in 96-well plates at 5,000 cells/well (for RWPE-1), or 7,500 cells/well (for 22Rvl, C4-2B, PC3), in 6-12 replicates. 22rv1 cell lines with stable gene depletions (as described above) were, transfected with 2% v/v of non-perturbing nuclear restricted green fluorescent label (IncuCyte™ NucLight™ Green BacMam 3.0, Essen Bioscience), acquiring phase (and green fluorescent images when appropriate) at 10×every 2 hours. Each well measurement was normalized to the number of cells at the initial time, and then normalized to the control (shGFP or vehicle treatment accordingly). The Incucyte Zoom software was used to analyzed and graph the results.

RNA isolation and reverse transcriptase quantitative RT-qPCR: Total RNA was collected using Trizol according to the manufacturer's protocol (Life Technologies), and isolated using Direct-zol RNA MiniPrep Plus (Zymo Research, Catalog number R2072). Total RNA was reverse transcribed using a cDNA ReverseTranscription kit (Applied Biosystems, Catalog number 4368814) as per the manufacturer's protocol. TaqMan probes from Applied Biosystems for FKBP5 (Hs01561006 ml), UBE2C (Hs00964100 gl), KIF20A (Hs00993573 ml), KIF23 (Hs00370852 ml), TOP2A (Hs01032137 ml), CCNB1 (Hs01030099 ml), CCNB2 (Hs01084593 gl), BUB1 (Hs01557695 ml), BUB1b (Hs01084828 ml) and GAPDH (Hs02786624 gl) were used.

Statistical analysis: Data was graphed and analyzed using Prism 7 (GraphPad) and Statistica 8.0 (Statsoft). Data was tested for normality (Shapiro-Wilk test) and homoscedasticity (Levene's test). If both assumptions were met then the data was tested for significance ($p<0.05$) using a two-tailed Student's T test or Analysis of Variances (ANOVA). Alternatively, Mann-Whitney's test and Kruskal-Walis test were used (non-parametric test).

Example 1—Gene Expression Analysis

Since genes comprise highly interconnected networks, an analysis was performed that would allow for the determination of the gene networks that exist at different stages of PC progression. By studying how gene networks behave across different stages of a disease, it is possible to identify effectors driving progression (Kadarmideen & Watson-Haigh, 2012). For this purpose, a powerful computational meta-analysis, termed Weighted Gene Co-Expression Network Analysis (WGCNA), was performed. In this type of analysis, genes represent nodes in a network, and are connected to other nodes by "edges". Some gene co-expression networks are binary (0=not connected, 1=connected). However, one of the advantages of a weighed co-expression analysis is that the edges weights are the Pearson correlation coefficients of the co-expression of the genes along different conditions, which makes the results of this analysis more biologically relevant (Kadarmideen & Watson-Haigh, 2012; Zhang & Horvath, 2005). This systems biology analysis allowed us to define modules, or clusters of genes that are highly connected. Thus, a module consists of genes whose expressions increase or decrease in a similar pattern across different disease conditions. The conditions or traits for this project were defined as: normal prostate tissue, benign hyperplasia, high-grade prostatic intraepithelial neoplasia (PIN), and cancerous (which was further divided into CRPC and/or metastasis when appropriate). The underlying concept is that the genes within a module are co-expressed across a series of traits, strongly suggesting that they share biological functions and are controlled by a common mechanism, like a transcription factor (Kadarmideen & Watson-Haigh, 2012).

We performed, to our knowledge, the largest gene expression analysis on clinical PC samples to date, including 375 samples from 8 different datasets (Table 1).

TABLE 1

| Dataset Identifier | Array | Tissue | Number of samples | Reference |
|---|---|---|---|---|
| EMEXP1243 | U133plus2 | Human | 81 | Traka et al., 2008 |
| GSE17951 | U133plus2 | Human | 154 | Jia et al., 2011 |
| GSE32982 | U133plus2 | Human | 9 | Vaarala et al., 2012 |
| GSE3325 | U1331us2 | Human | 19 | Varambally et al., 2005 |
| GSE45016 | U133plus2 | Human | 11 | Satake et al., 2010 |
| GSE46602 | U133plus2 | Human | 50 | Unpublished |
| GSE55945 | U133plus2 | Human | 21 | Arredouani et al., 2009 |
| GSE7307 | U133plus2 | Human | 30 | Rands et al 2013., |
| | | TOTAL | 375 | |

FIG. 1 shows the WGCNA analysis results, where 20 distinctive gene modules were defined and arbitrarily given the name of a color. For example, the modules white and yellowgreen contain genes whose expression was either non-associated with or downregulated in normal, benign hyperplasia, and neoplasia tissue; but whose expression was highly increased in cancerous samples. The association between those modules to different cancer progression stages strongly suggests that the genes within those modules are relevant to study as possible PC drivers and new targets. We then analyzed RNA-seq data from circulating tumor cells (CTCs) from PC patients (datasets from Antonaraikis et al., 2014; Miyamoto et al., 2015). CTCs were classified as AR-V7+(CTCs that expressed AR-V7), or otherwise AR-V7-. We searched for genes whose expression (RNA-seq based) was different in between AR-V7+ versus AR-V7- CTCs, and grouped those genes according to the WGCNA gene modules we defined. We found that Antonaraikis et al. dataset had a broad distribution among our gene modules, where the number of samples is only 4 CTCs. However, Miyamoto et al. dataset, comprised of 87 CTC specimens (from 22 different patients), showed that the white module (green module in Example 2) contains the highest percentage of genes within that module that are differentially express between patients with AR-V7+ CTCs versus AR-V7—CTCs.

To proceed with our system-level analysis and identify a module possibly regulated by AR-V7, we performed microarray studies in the human CRPC cell line 22Rv1 to analyze gene expression changes after inducibly knocking-down AR-V7 or GFP as a control. 22Rv1 contain high levels of AR-V7 and depend on AR-V7 for growth and survival (Guo et al., 2009; Marcias et al., 2010). Genes that were significantly regulated by AR-V7 were distributed in according to the WGCNA module with which they corresponded. From the combination of these two analyses, one from PC patient samples, and one experimentally obtained from a human PC cell line, we found that almost 80% of the genes within the white module (green module in Example 2) were positively regulated by AR-V7(i.e. their expression decreased upon AR-V7 depletion), but were not regulated by GFP knockdown (control).

We performed a Gene ontology (GO) enrichment analysis on the genes contained in the white module (green module in Example 2), since this module contains genes whose expression increases during PC progression; contains a large number of genes present in AR-V7+ CTC specimens but not AR-V7-CTCs; and is composed mostly by genes positively regulated by AR-V7. GO enrichment analysis on the white gene set module (green module in Example 2) revealed that these genes are mainly involved in mitotic cell cycle process, cell division, mitotic nuclear division, and chromosome and sister-chromatid segregation.

With the objective of constructing a functional gene network for AR-V7, we used a high-throughput screening method in the yeast S. pombe. The Yeast Augmented Network Analysis (YANA) was performed in S. pombe, where the gene of interest (in this case, AR-V7) was expressed as a fusion protein under the control of an inducible promoter. A synthetic genetic array (SGA) screen was then performed to identify genetic modifiers that alter yeast fitness (growth). SGA was performed by crossing the yeast strain expressing AR-V7 (or its non-induced control) with a yeast deletion strain library, where over 90% of non-essential genes are individually deleted (Wiley el al., 2014). Each cross was performed in quadruplicate and the resulting strain was scored based on its fitness (growth). From the SGA screening, "hits" were identified, which are deletion strains that caused a change in yeast growth upon being crossed with yeast expressing AR-V7 (induced), but not with its non-induced control. These hits represent the genes that have a functional interaction with AR-V7. Essential genes cannot be deleted and thus were not used to create yeast deletion strains for the SGA. Therefore, essential genes were added back into the gene network. The criteria for inclusion of essential genes was that they interacted with at least two "hits" found in the SGA. The protein-protein interaction information between an essential gene and two or more "hits" is obtained from experimental data available online, at high confidence (0.7) in a pombe protein network (from STRING).

The human orthologs for gene "hits" (including essential and non-essential genes added) were assembled into a network using STRING that maps protein-protein interactions using data from experiments available online (for example: BIND, IntAct, MINT, Biocarta, GO, KEGG, and Reactome) (Wiley et al., 2014). This approach allowed us to build a human AR-V7 gene functional network, where we took an unbiased approach to identify proteins that interact with AR-V7 in a physical and/or functional manner that could be potential therapeutic targets for PC. We performed a STRING network analysis of AR-V7 interactome, where we found that a large number of genes that functionally interact with AR-V7 are related to biological processes (Gene Ontology analysis) such as protein localization to the endoplasmic reticulum (including those mediated by signal recognition particle (SRP)), mRNA catabolic processes (mRNA degradation and mRNA decay), and genes associated to viral transcription regulation and viral transcription regulation by the host. Moreover, AR-V7 interactome contains numerous genes involved in cell cycle pathways, viral carcinogenesis pathways and alcoholism-related pathway (which contains genes such as NMDA receptors, HDACs, HRAS, KRAS, and CAMKKs) from KEGG-pathway analysis.

Notably, the white (green module in Example 2) and yellowgreen WGCNA gene modules of patient samples were the ones that contained the highest percentage of genes present also AR-V7 functional association network. Most importantly, we combined the results obtained from this SGA screening with our previous analyses to identify genes that met the following criteria: 1) expression increases with disease progression in patient samples (determined by meta-analysis of patient datasets), 2) show regulation by AR-V7 (from our microarray) and 3) have a functional interaction with AR-V7 (from YANA). We found 7 genes that met these criteria and will be referred to hereafter as our "gene set". These genes are: kinesin family-member 20A (KIF20A), kinesin family-member 23 (KIF23), topoisomerase DNA II alpha (TOP2A), cyclin B1 (CCNB1), cyclin B2 (CCNB2), BUB1 mitotic checkpoint serine/threonine kinase (BUB1), and BUB1 mitotic checkpoint serine/threonine kinase B (BUB1B).

To validate the gene set, we examined the gene expression of these 7 genes in an additional dataset not included in our first analysis. We utilized a microarray dataset obtained by Hornberg et al. (2011) of CRPC bone metastases samples, where patient samples were classified as "AR-V7 high" (when the AR-V7 mRNA levels were in the upper quartile), or otherwise as "AR-V7 low". Excluding BUB1B, whose probe was not present in the array, the mRNA expression of 5 out of the remaining 6 genes from the gene set was significantly upregulated in patient samples containing high levels of AR-V7 (KIF20A, KIF23, TOP2A, CCNB2, BUB1), when compared to samples with lower levels of AR-V7. These data from PC patient metastases further validates the relevance of this gene set identified from the integration of multiple independent analyses in various systems (patient samples, cell lines, and yeast screening).

We then analyzed another independent dataset, of 499 PC patient samples, available at cBioPortal for Cancer Genomics (prostate adenocarcinoma provisional dataset from TCGA). We found that all the genes within the gene set had a highly significant tendency towards co-occurrence within patient samples.

To determine whether the expression levels of the gene set at the time of patient biopsy had a prognostic value, we built disease-free survival (DFS) Kaplan-Meier curves using the prostate adenocarcinoma provisional dataset from TCGA (499 patient samples). Patients with higher expression of any of the genes within the gene set (mRNA expression Z-score threshold±1.5) showed significant lower DFS when compared to those patients with normal expression levels for that gene ($p<0.05$ for KIF20A, CCNB1, CCNB2, BUB1, BUB1B; $p<0.1$ for KIF23, TOP2A, data not shown). More interestingly, patients overexpressing the 7 genes within the gene set (gene signature) had significantly decreased DFS. While PC patients with normal expression levels of these genes had a 14.9% chance of disease recurrence after treatment (56 patients out of 375); those patients expressing higher levels of the 7 genes within the gene signature doubled their chances of recurring after treatment to 30.2% (33 patients out of 109). This indicates that this gene signature could provide a valuable prognostic marker for disease aggressiveness and likelihood of relapse at the time of PC biopsy.

Next, an in vitro approach was utilized using the human CRPC cell line 22Rv1 to examine the activity of the genes within the gene set. Individual depletion of each of these genes, in the absence of androgen (where cells are highly dependent on AR-V7 activity), decreased cell proliferation. In fact, most of them inhibited cell proliferation to the same extent as AR-V7 depletion. Similar results on cell growth after gene depletion were observed in a second human PC cell line: C4-2b, which were grown in the presence of androgen. Since the genes within the gene set are not only regulated by AR-V7, but also interact with AR-V7, we looked into AR transcriptional activity utilizing a dual-plasmid AR-driven luciferase assay system. These experiments in 22Rv1 were performed in the absence of androgen (AR ligand), where most of AR transcriptional activity is driven by the ligand-independent AR-V7 variant. We found that depletion of 6 of the 7 genes caused decreased AR ligand independent transcriptional activity, comparable to AR-V7 knockdown. This data suggests that this genes work with AR-V7 in a positive feedback-loop, since their expression is regulated by AR-V7, and they in term enhance AR-V7 transcriptional activity.

Discussion

It is well established that the vast majority of PC and CRPC depend on AR signaling for viability (Robinson et al., 2015), and splice variants, mainly AR-V7, play a major role as a constitutively active transcription factor, even in ADT conditions. Our current ADT treatments for non-localized PC (such as abiraterone and enzalutamide) target the synthesis of AR ligand or the binding of the ligand to AR LBD. However, AR-V7 is not targeted by these therapies because it lacks its LBD and functions in a ligand-independent manner, driving AR signaling still under our most cutting-edge therapies and promoting an oncogenic program. Since targeting AR-V7 is a major challenge, it is essential that we understand the biological processes and genes that is regulating to drive PC progression.

Integrative approaches can transform one-dimensional cancer signatures into multidimensional networks, and infer causality (Rhodes & Chinnaiyan, 2005). In their report, Rhodes and Chinnaiyan (2005) highlighted different categories integrative analyses: genes activated in cancer and targeted by transcription factors, as well as pathways and interaction networks. A unique and critical aspect about our work is that we performed all those integrative analyses, to create a systems-biology approach where we converged the results of multiple unbiased integrative analyses, which included meta-analyses on patients gene expression profiling, microarray assays on cell lines to identify AR-V7 regulated genes, construction of AR-V7 functional network, as well as inter-validation with other independent human datasets and in vitro experimentation.

The meta-analysis performed here was on 8 independent microarray datasets, comprising 375 PC patient samples, making it, to our knowledge, the largest meta-analysis performed on gene-expression of clinical PC samples to date. The fact that this large-scale analysis was performed on a large number of samples from multiple datasets provides robustness to the module definition, as well as power in the ability to identify relevant modules. Most importantly, the gene signature that we identified by combining it with other integrative analyses was further validated by using other patient gene expression datasets that were not included in the initial meta-analysis, such as Hornberg et al., 2011 and TCGA prostate adenocarcinoma provisional dataset.

Moreover, this is the first time the AR-V7 interactome has been mapped for PC. The high-throughput genetic screening described herein allowed for the identification of genes that interact with AR-V7, either through direct protein interactions and/or through common cellular pathways and processes. When combining these data with the meta-analysis on patient samples and our cell-line based microarray, we could identify genes that are highly expressed in PC, but not before the disease, that are regulated by AR-V7, and that interact with AR-V7.

KIF20A and KIF23 are kinesins, anterograde-transport molecular motors powered by ATP, involved in multiple cellular roles such as mitosis, vesicle trafficking, and migration, through their interaction with microtubules (Bergner et al., 2005; Hirokawa et al., 1998). KIF20A is linked to paclitaxel resistance in breast cancer (Khongkow et al., 2016), gastric cancer (Yan et al, 2012), and KIF20 vaccination in a clinical trial phase I/II for advanced pancreatic cancer showed promising results with a disease control of 72% (Asahara et al., 2013). However, this gene has not been studied in prostate cancer. The other kinesin identified, KIF23, promotes glioblastoma growth (Takahashi et al., 2012) and is a valuable prognostic marker (Sun et al., 2015), is upregulated in non-small cell lung cancer (Valk et al., 2011), and predicts clinical outcome in patients with primary lung cancer (Kato et al., 2016). The only study that links KIF23 to PC found that the microRNA miR-331-3p (which targets KIF23) is upregulated in aggressive (Gleason score>8) PC patient samples in comparison to non-aggressive PC (Gleason score<5) (Wang et al., 2009).

TOP2A is a DNA topoisomerase involved in DNA replication, transcription, repair, and chromatin remodeling by inducing temporary DNA breaks (Champoux J., 2001). TOP2A is amplified in multiple cancers (Rody et al., 2009; Wong et al., 2009; Lan et al, 2014, Jain et al, 2013), and its expression is correlated with higher Gleason score in prostate cancer (De Resende et al., 2013). TOP2A is a yeast essential gene, and for this reason it was not used in the SGA. However, TOP2A was added into the AR-V7 interactome because it interacted with two "Hits" (PHB and RBBP4), as discussed above.

Cell cycle dysregulation is a hallmark of cancer (Hanahan & Weinberg, 2000). Therefore, it is not surprising that two members of the cyclin B family appeared in our gene set. Cyclin B plays a major role in mitosis, is necessary for cells to enter and exit mitosis, and is associated with CDK1 (Pines & Hunter, 1991). While both CCNB1 and CCNB2 drive tumorigenesis when overexpressed (Nam & Deursen, 2014), they differ in their cellular localizations. CCNB1 is an essential gene that localizes with microtubules, while CCNB2 is associated with the Golgi region (Jackman et al., 1995). The role of CCNB1 in promoting cell proliferation and malignant transformation has been shown in multiple cell lines and human cancers, such as non-small cell lung cancer (Soria et al., 2000), colorectal cancer (Wang et al., 1997) and breast cancer (Agarwal et al, 2009). CCNB1 depletion in HeLa cells inhibits growth by cell-cycle arrest in G2 and induction of apoptosis (Yuan et al., 2006). In prostate cancer cell lines, AR has been shown to increase CCNB1 expression via the AKT pathway (Yu et al., 2014). On the other hand, CCNB2 plays a role in centrosome separation (Nam & Deursen, 2014); its expression is increased in colorectal adenocarcinoma (Park et al, 2007) and is associated with a worse outcome in breast cancer patients (Shubbar et al., 2013).

BUB1 and BUB1B are kinases involved in spindle checkpoint function that act mainly by inhibiting the anaphase-promoting complex (APC/C). Interestingly, APC/C is involved in cyclin B degradation (Chang et al., 2003). This anaphase delay ensures proper chromosomal segregation and serves as a surveillance mechanism (Tang et al, 2004). BUB1 regulates chromosome segregation in a kinetochore-dependent and independent manner (Klebig et al., 2009), and it is overexpressed in many types of cancer including gastric cancer (Grabsch et al., 2003) and colorectal cancer (Shichiri et al., 2002). On the other hand, BUB1B is overexpressed in breast cancer (Scintu et al., 2007; Yuan et al, 2006). However, the role and importance of these BUB proteins has not yet been characterized in prostate cancer.

There is a major need to identify novel prognostic markers for PC aggressiveness and likelihood of biochemical recurrence after primary treatment. It is imperative to know which patients will be appropriate candidates for active surveillance and which patients have high-risk tumors which should not be undertreated, since their risk for relapse is high (Cooperberg & Carroll, 2015). We found that patients that have higher expression levels of the genes within the gene set we identified have a risk over two times higher of relapsing after primary therapy than patients that do not. Most importantly, the gene expression signature we identified is biopsy-based, which could serve at early time of PC diagnosis to guide treatment according to risk.

All patent documents and journal articles referenced herein or provided below are expressly incorporated by reference in their entireties.

REFERENCES FOR EXAMPLE 1

Arredouani, M. S., Lu, B., Bhasin, M., Eljanne, M., Yue, W., Mosquera, J. M., . . . & Sanda, M. G. (2009). Identification of the transcription factor single-minded homologue 2 as a potential biomarker and immunotherapy target in prostate cancer. Clinical Cancer Research, 15(18), 5794-5802.

Bin, Z., & Steve, H. (2005). A general framework for weighted gene co-expression network analysis. Statistical applications in genetics and molecular biology, 4(1), 1-45.

Chandran, V., Coppola, G., Nawabi, H., Omura, T., Versano, R., Huebner, E. A., & Blesch, A. (2016). A systems-level analysis of the peripheral nerve intrinsic axonal growth program. Neuron, 89(5), 956-970.

Cooperberg, M. R., & Carroll, P. R. (2015). Trends in management for patients with localized prostate cancer, 1990-2013. JAMA, 314(1), 80-82.

Cottard, F., Asmane, I., Erdmann, E., Bergerat, J. P., Kurtz, J. E., & Ceraline, J. (2013). Constitutively active androgen receptor variants upregulate expression of mesenchymal markers in prostate cancer cells. PloS one, 8(5), e63466.

Guo, Z., Yang, X., Sun, F., Jiang, R., Linn, D. E., Chen, H., . . . & Kung, H. J. (2009). A novel androgen receptor splice variant is up-regulated during prostate cancer progression and promotes androgen depletion—resistant growth. Cancer research, 69(6), 2305-2313.

Jia, Z., Wang, Y., Sawyers, A., Yao, H., Rahmatpanah, F., Xia, X. Q., . . . & Goodison, S. (2011). Diagnosis of prostate cancer using differentially expressed genes in stroma. Cancer research, 71(7), 2476-2487.

Karantanos, T., Corn, P. G., & Thompson, T. C. (2013). Prostate cancer progression after androgen deprivation therapy: mechanisms of castrate resistance and novel therapeutic approaches. Oncogene, 32(49), 5501-5511.

Kong, D., Sethi, S., Li, Y., Chen, W., Sakr, W. A., Heath, E., & Sarkar, F. H. (2015). Androgen receptor splice variants contribute to prostate cancer aggressiveness through induction of EMT and expression of stem cell marker genes. The Prostate, 75(2), 161-174.

Langfelder, P., & Horvath, S. (2008). WGCNA: an R package for weighted correlation network analysis. BMC bioinformatics, 9(1), 1.

Lokhandwala, P. M., Riel, S. L., Haley, L., Lu, C., Chen, Y., Silberstein, J., & Partin, A. W. (2016). Analytical Validation of Androgen Receptor Splice Variant 7 Detection in a Clinical Laboratory Improvement Amendments (CLIA) Laboratory Setting. The Journal of Molecular Diagnostics.)

Marcias, G., Erdmann, E., Lapouge, G., Siebert, C., Barthelemy, P., Duclos, B., . . . & Kurtz, J. E. (2010). Identification of novel truncated androgen receptor (AR) mutants including unreported pre-mRNA splicing variants in the 22Rv1 hormone-refractory prostate cancer (PCa) cell line. Human mutation, 31(1), 74-80.

Mortensen, M. M., HOyer, S., Lynnerup, A. S., Orntoft, T. F., SOrensen, K. D., Bone, M., & Dyrskj0t, L. (2015). Expression profiling of prostate cancer tissue delineates genes associated with recurrence after prostatectomy. Scientific reports, 5.

Mostaghel, E. A., Marck, B. T., Plymate, S. R., Vessella, R. L., Balk, S., Matsumoto, A. M., . . . & Montgomery, R. B. (2011). Resistance to CYP17A1 inhibition with abiraterone in castration-resistant prostate cancer: induction of steroidogenesis and androgen receptor splice variants. Clinical cancer research, 17(18), 5913-5925.

Qu, Y., Dai, B., Ye, D., Kong, Y., Chang, K., Jia, Z., . . . & Shi, G. (2015). Constitutively active AR-V7 plays an essential role in the development and progression of castration-resistant prostate cancer. Scientific reports, 5.

Rhodes, D. R., & Chinnaiyan, A. M. (2005). Integrative analysis of the cancer transcriptome. Nature genetics, 37, S31-S37.

Robinson, D., Van Allen, E. M., Wu, Y. M., Schultz, N., Lonigro, R. J., Mosquera, J. M., . . . & Beltran, H. (2015). Integrative clinical genomics of advanced prostate cancer. Cell, 161(5), 1215-1228.

Satake, H., Tamura, K., Furihata, M., Anchi, T., Sakoda, H., Kawada, C., . . . & Shuin, T. (2010). The ubiquitin-like molecule interferon-stimulated gene 15 is overexpressed in human prostate cancer. Oncology reports, 23(1), 11.

Siegel, R. L., Miller, K. D., & Jemal, A. (2016). Cancer statistics, 2016. CA: a cancer journal for clinicians, 66(1), 7-30.

Sun, S., Sprenger, C. C., Vessella, R. L., Haugk, K., Soriano, K., Mostaghel, E. A., . . . & Nelson, P. S. (2010). Castration resistance in human prostate cancer is conferred by a frequently occurring androgen receptor splice variant. The Journal of clinical investigation, 120(8), 2715-2730.

Vaarala, M. H., Hirvikoski, P., Kauppila, S., & Paavonen, T. K. (2012). Identification of androgen-regulated genes in human prostate. Molecular medicine reports, 6(3), 466-472.

Varambally, S., Yu, J., Laxman, B., Rhodes, D. R., Mehra, R., Tomlins, S. A., . . . & Wei, J. T. (2005). Integrative genomic and proteomic analysis of prostate cancer reveals signatures of metastatic progression. Cancer cell, 8(5), 393-406.

Wang, Y., Xia, X. Q., Jia, Z., Sawyers, A., Yao, H., Wang-Rodriquez, J., & McClelland, M. (2010). In silico estimates of tissue components in surgical samples based on expression profiling data. Cancer research, 70(16), 6448-6455.

Moreno, S., Klar, A., & Nurse, P. (1991). [56] Molecular genetic analysis of fission yeast *Schizosaccharomyces pombe*. Methods in enzymology, 194, 795-823.

Dixon, S. J., Fedyshyn, Y., Koh, J. L., Prasad, T. K., Chahwan, C., Chua, G., . . . & Kim, D. U. (2008). Significant conservation of synthetic lethal genetic interaction networks between distantly related eukaryotes. Proceedings of the National Academy of Sciences, 105(43), 16653-16658.

Example 2— Further Gene Expression Analysis

Figure 5C:
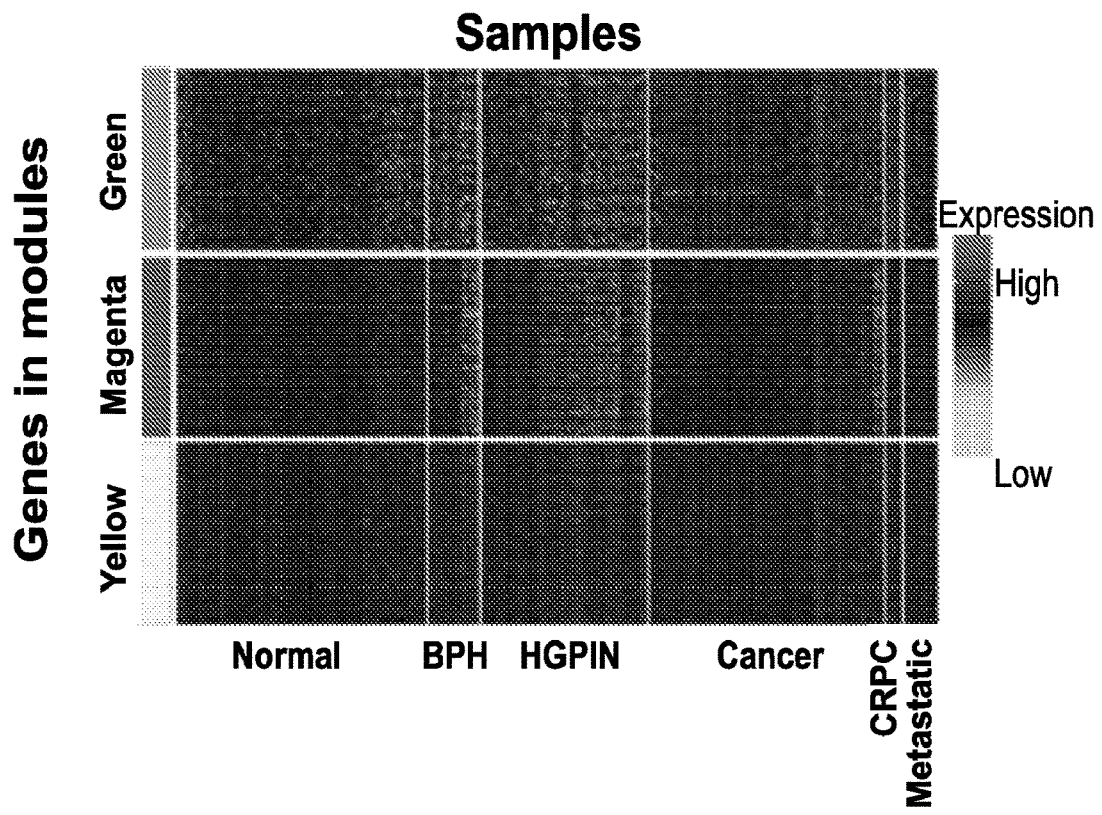
Figure 5D:
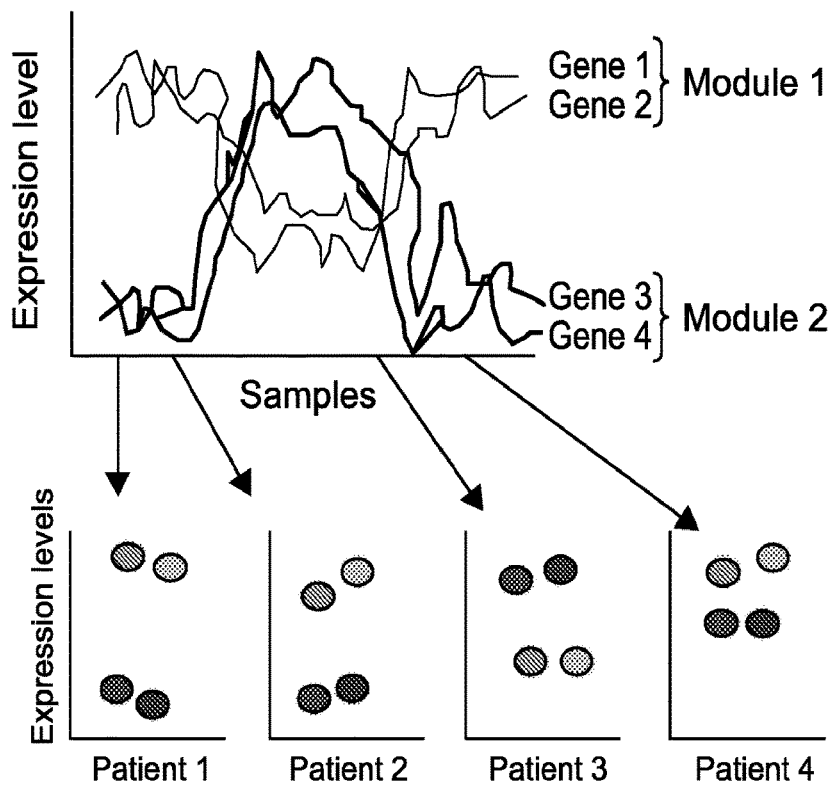

WGCNA was performed to identify, in an unbiased manner, gene modules associated with different types/stages of PC pathologies and phenotypes. WGCNA is based on the concept that co-expressed genes across a series of traits (in this instance, pathological features of human prostate) share biological functions and/or are controlled by a common mechanism, such as by a specific transcription factor(s) (Kadarmideen & Watson-Haigh, 2012). For this meta-analysis we used eight publically available microarray datasets that utilized the same array platform (FIG. 5A) and encompassed six different prostate phenotypes/disease stages (FIG. 5B). The microarray datasets were combined and used for network construction (FIG. 5C). Gene modules were first assembled with a minimum module size of 30 genes, and highly similar modules were combined using a dissimilarity threshold of 0.25. The resulting 20 gene modules were correlated to different prostate phenotypes (FIG. 1A). Three of the 20 modules (arbitrarily termed: green, magenta, and yellow) had significant positive associations with PC and CRPC (FIGS. 1A & 5D).

Figure 1B:
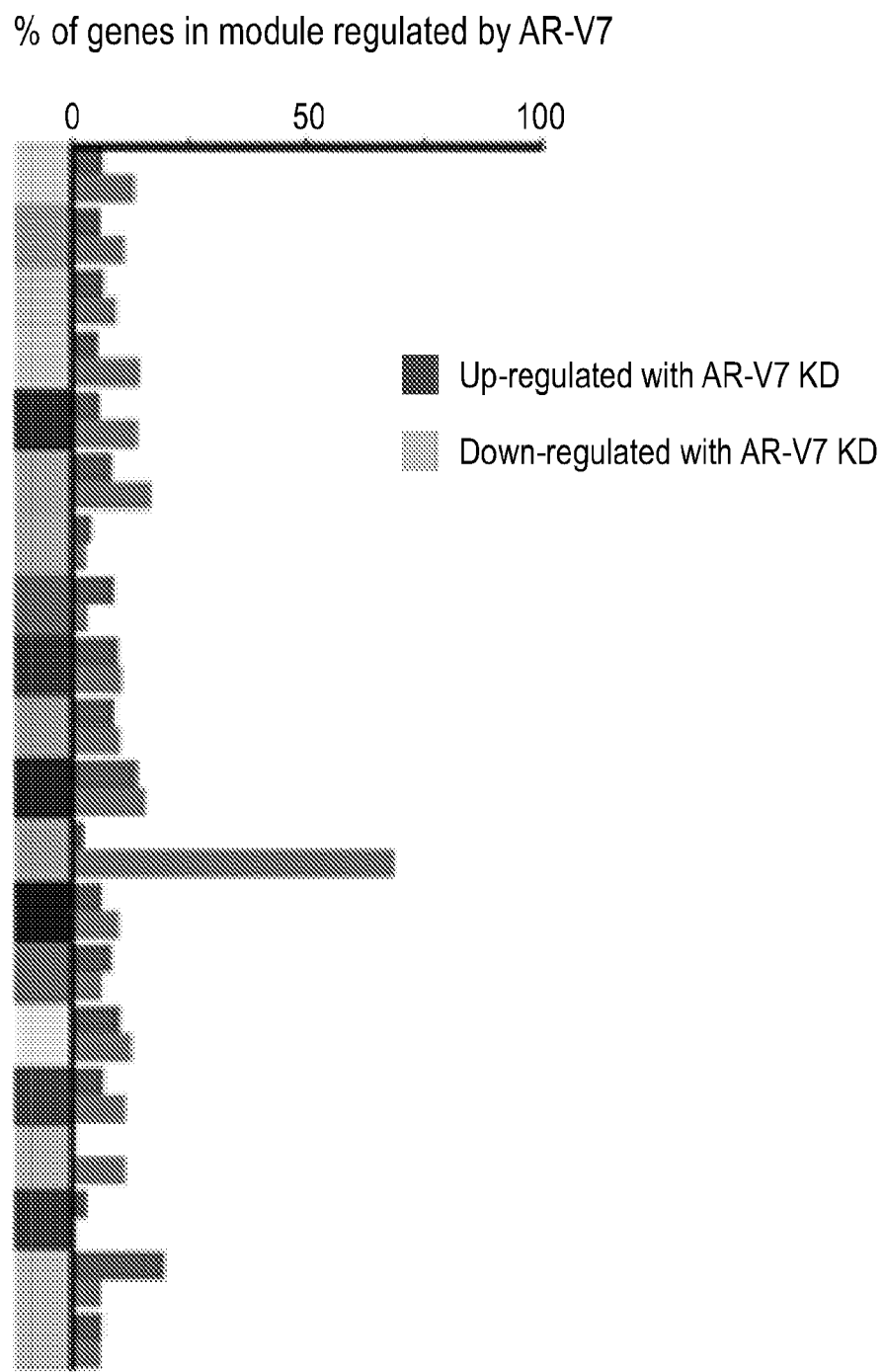
Figure 6A:
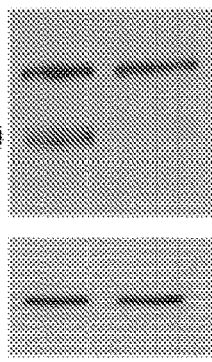
FIGS. 6A and 6B: shGFP control samples for the gene expression array are not significantly enriched among WGCNA modules.
Figure 6B:
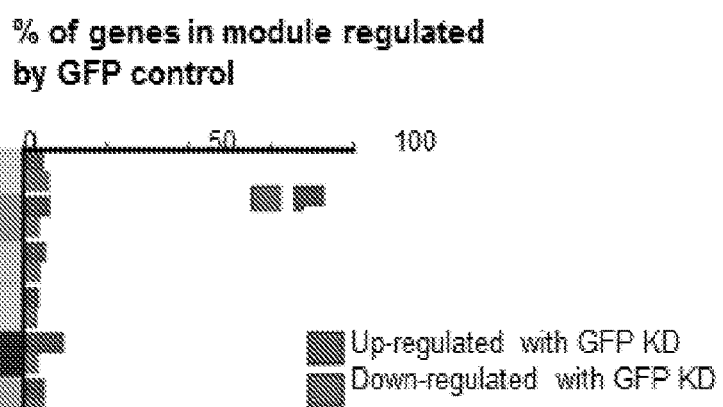

To determine whether any of the WGCNA modules were enriched for genes regulated by AR-V7, we performed gene expression profiling in the human CRPC cell line 22Ry1.22Ry1 contain high levels of AR-V7 and depend on AR-V7 for growth and survival (Guo et al., 2009; Marcias et al., 2010). We performed doxycycline-inducible knockdown of AR-V7 using a specific tet-p1K0 shAR-V7 system (FIG. 6A and Peacock et al., 2012). We then mapped the resulting 3,439 AR-V7-regulated genes to the WGCNA modules. Strikingly, nearly 75% of the green module genes exhibited decreased expression following AR-V7 knockdown (i.e: were up-regulated by AR-V7) (FIG. 1B). The green module was highly enriched in genes associated with cell proliferation, particularly mitotic cell cycle and chromosome segregation (FIG. 5E. This module contained a number of genes previously linked to prostate or other types of cancers including RADS], AURKA, CENPE, EZH2, TOP2A, BUB], TPX2, CDKJ, and CCNB]. In contrast, there was no significant enrichment of genes regulated under the control condition (shGFP) with any of the WGCNA modules (FIG. 6B).

Figure 1C:
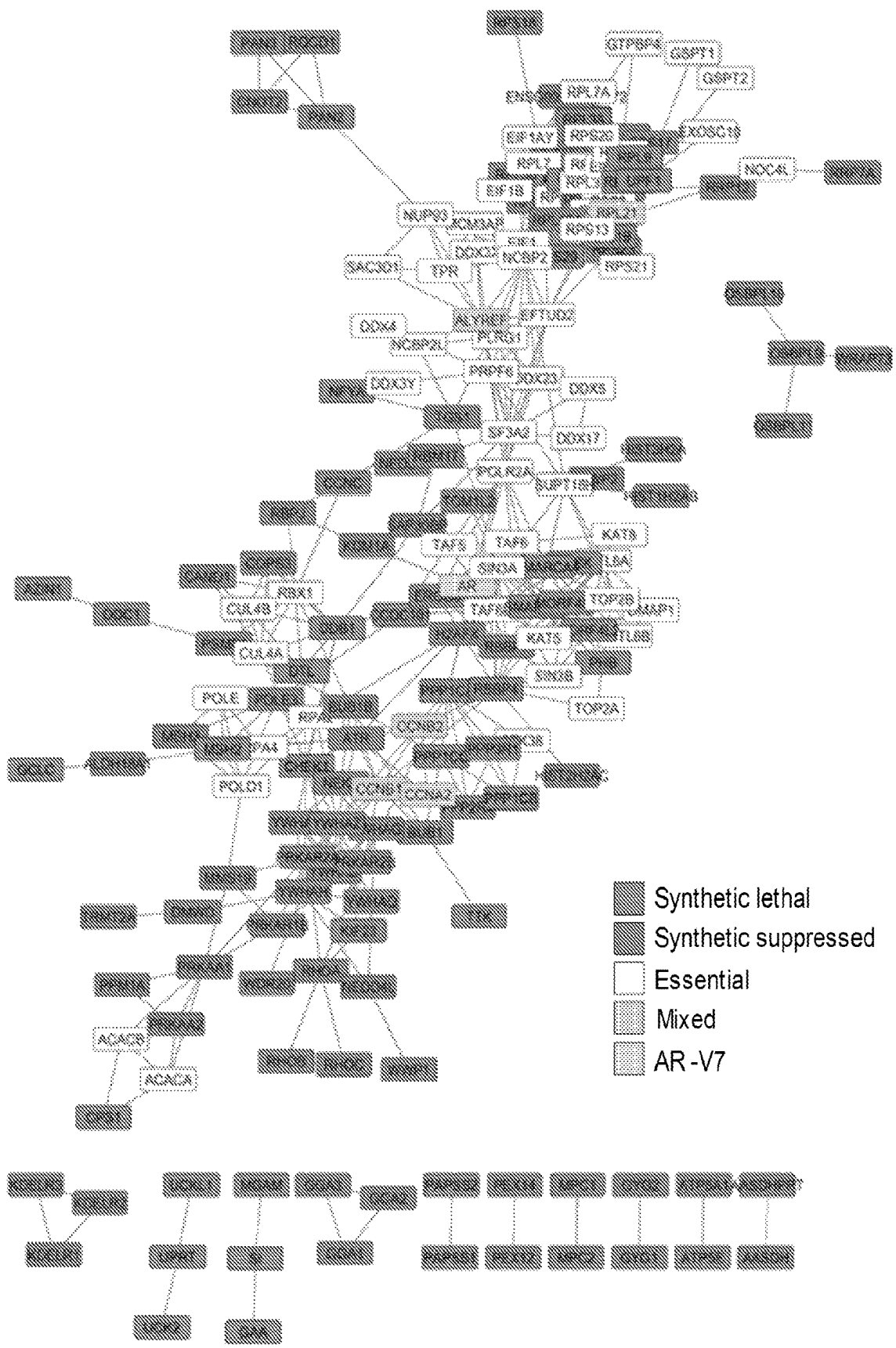
Figures 1D, 1E:
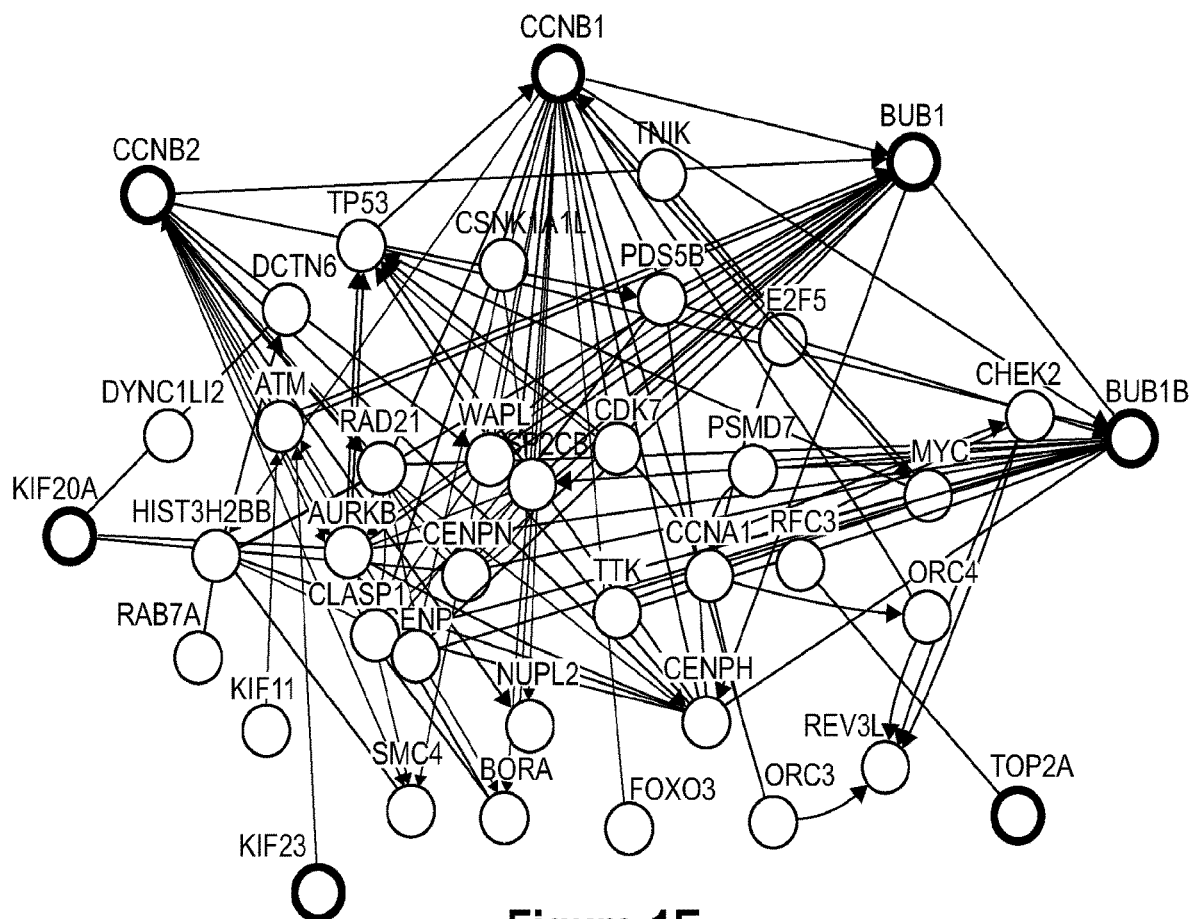
Figure 7:
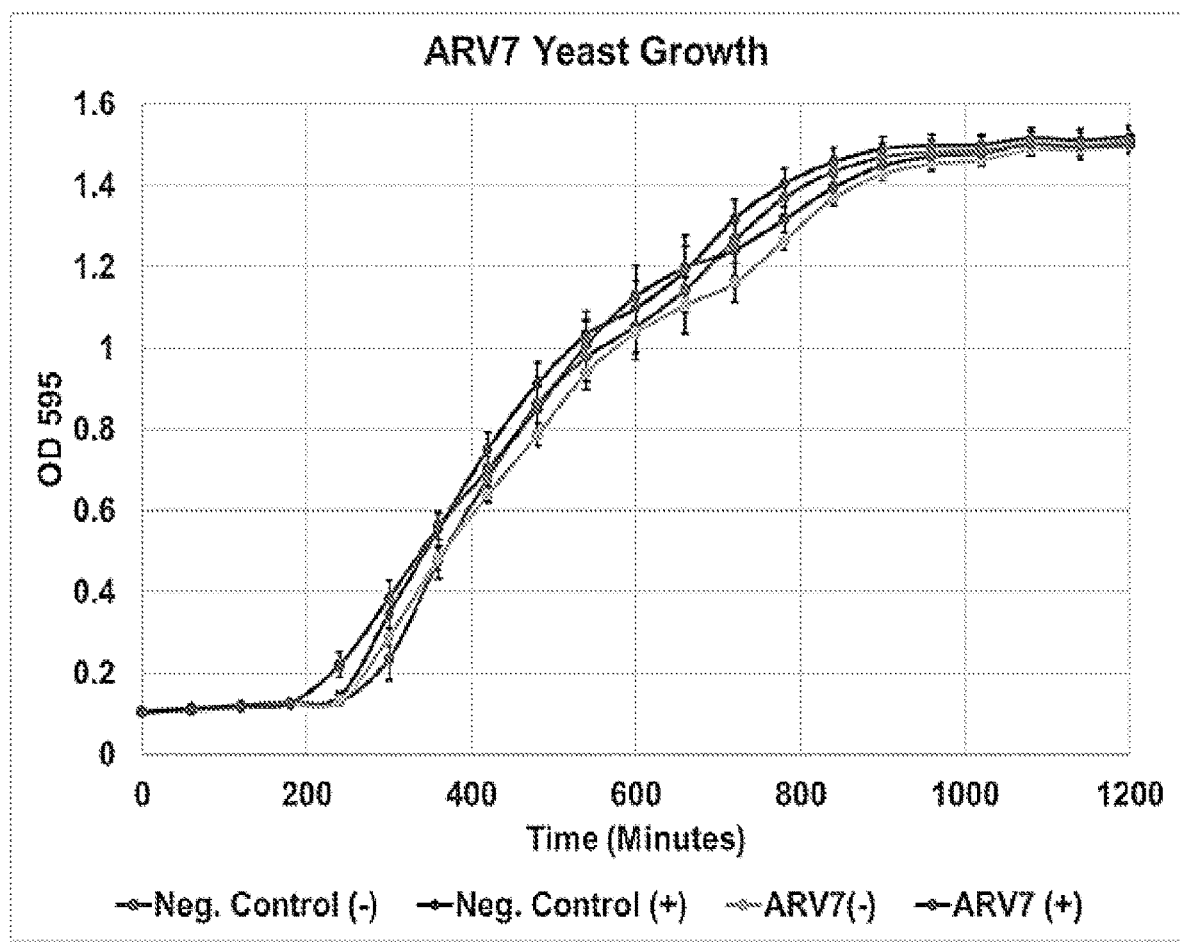
FIG. 7: Expression of AR-V7 does not affect yeast growth rate. Growth curve analysis was completed in the presence and absence of thiamine. Colony growth was documented on a flatbed scanner.

Thus, 60 genes (nearly 75% of the green module) were identified that are regulated by AR-V7, whose expression was associated with and upregulated in PC, CRPC, and metastasis in the WGCNA meta-analysis of human samples. This set of 60 clinically relevant genes, which are regulated by AR-V7, can be further analyzed in a number of ways to understand the mechanisms of AR variant action in PC. In this particular study, we were interested in identifying those genes that also interact in a biologically relevant way and might participate in a positive feedback loop with AR-V7. Such genes are likely to encode key prognostic markers as well. as potential therapeutic targets acting within the AR-V7 network To identify such genes, an AR-V7 functional genetic interactome was generated using a high-throughput synthetic genetic array (SGA) screening method in the yeast *Schizosaccharomyces pombe*. This unbiased and powerful approach has successfully identified other human disease-related protein interactomes (e.g., for X-linked spinal muscular atrophy (SMA) [Wiley et al., 2014]). Using the methods described in detail in Wiley et al., 2014, we generated an inducible *S. pombe* strain expressing an HA-tagged AR-V7 fusion protein integrated under the control of the runt1 thiamine-repressible promoter. Expression of AR-V7 did not significantly affect yeast growth (FIG. 7). The AR-V7 strain was then crossed with a deletion library to create 3,664 unique gene deletion strains that inducibly express AR-V7. Functional genetic interactions ("hits") were inferred when expression of AR-V7 altered the strain's growth rate ("fitness"). Gene hits therefore encode proteins that are functionally linked with AR-V7 as their deletion affected yeast growth only when AR-V7 was expressed (induced conditions). The human orthologs for gene hits were then analyzed with a protein—protein interaction network using STRING (FIG. 1C). Gene ontology analysis of the AR-V7 interactome identified several distinct biological processes, including cell cycle regulation (FIG. 8).

Figure 9:
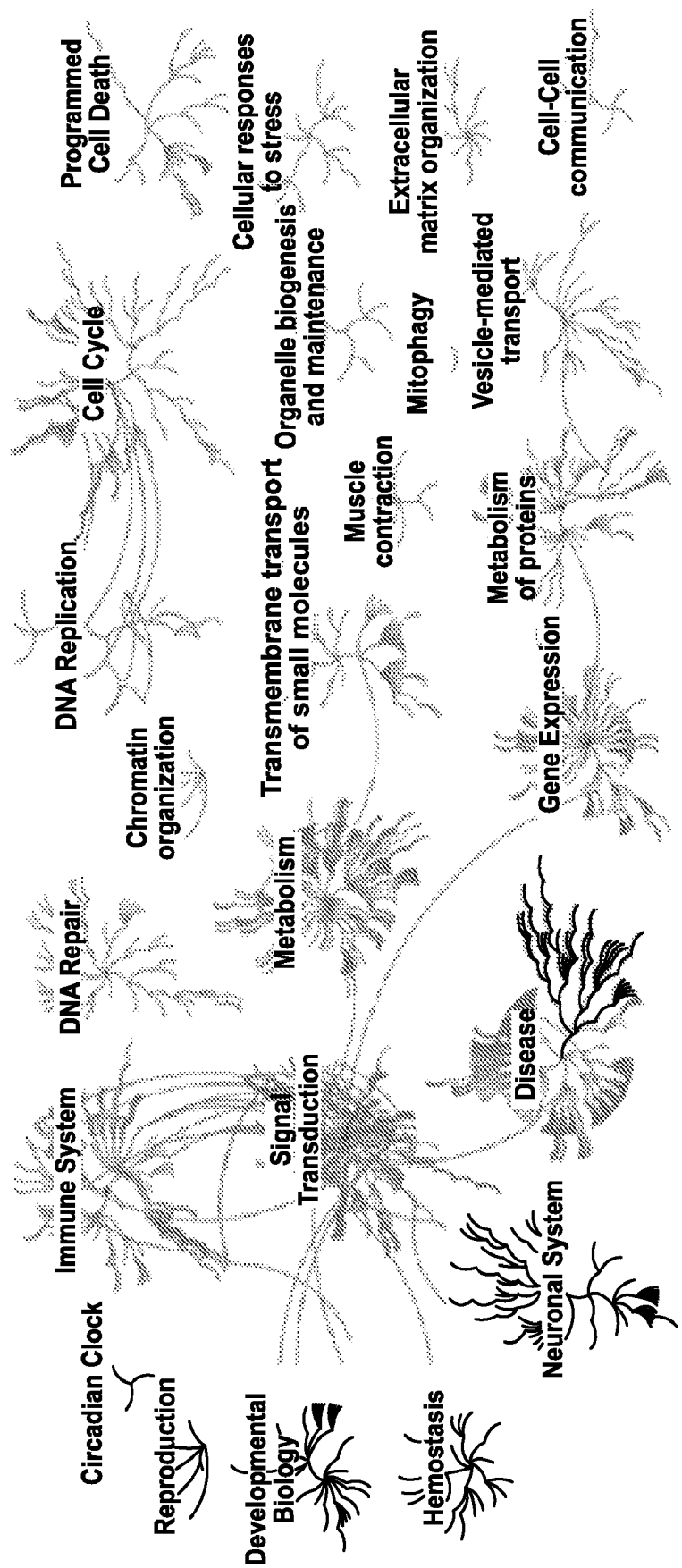
FIG. 9: Pathway analysis of the seven gene set reveals a strong association to cell cycle. The analysis was performed using https://reactome.org.

Integrating the data from the AR-V7 interactome with the AR-V7 regulated green module could reveal strongly disease-relevant candidates for AR-V7 feedback regulation. In this way, we identified 7 genes, present in the WGCNA green module (FIG. 1A) (thus, associated with and upregulated in disease progression), regulated by AR-V7 (FIG. 1B), and that functionally interact with AR-V7 (FIG. 1C). This seven gene set (FIG. 1D) was composed of: kinesin family-member 20A (KIF20A), kinesin family-member 23 (KIF23), topoisomerase DNA II alpha (TOP2A), cyclin B1 (CCNB1), cyclin B2 (CCNB2), BUB1 mitotic checkpoint serine/threonine kinase (BUB1), and BUB1 mitotic checkpoint serine/threonine kinase B (BUB1b). This seven gene set comprises a highly interconnected network (FIG. 1E) and pathway analysis revealed a strong role in cell cycle (FIG. 9).

To validate these findings, the expression of the seven genes was assessed in an independent collection of human CRPC specimens. Because these seven genes were regulated by AR-V7 in PC cells, we examined whether they were coexpressed with AR-V7 in an independent gene expression profiling array dataset of human CRPC bone specimens, which were grouped by relative levels of AR-V7 (Hornberg et al., 2011). Expression of each of the seven genes was significantly elevated in the human PC bone metastases with highest AR-V7 expression compared to the specimens with the lowest relative levels of AR-V7 (FIG. 2A).

Figure 10:
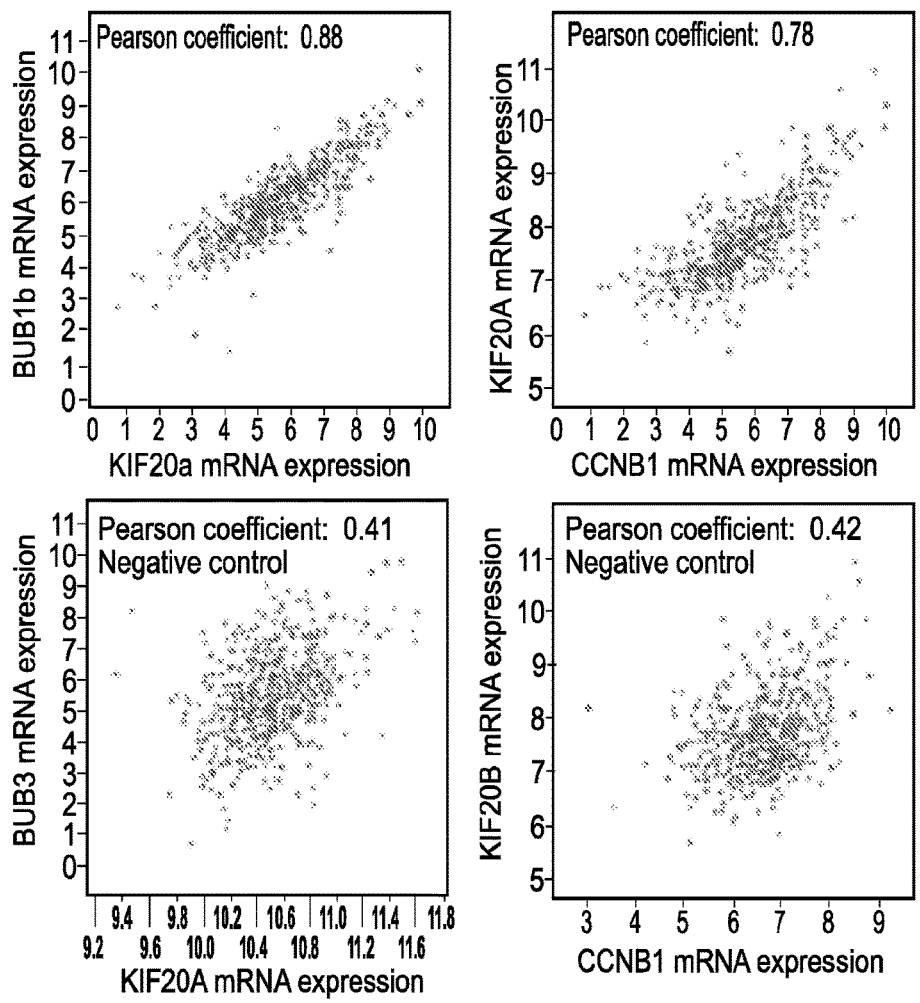
FIG. 10: The seven genes are co-expressed in human PC samples. The left panels (top graphs) show sample pairwise comparisons (KIF20a & BUB 1b; CCNB1 & KIF20a mRNAs) in human PC samples obtained from the TCGA Provisional Adenocarcinoma dataset, where log 2 transformation was applied (n=499). Analysis of BUB3 and KIF20b, which are not members of the seven gene set, were compared with KIF20A and CCNB1, respectively, as negative controls. The table summarizes the Pearson correlation values between the expression levels of each pair of the seven genes.

In another independent PC patient dataset, we found through pairwise comparisons that the expression of the seven genes were highly correlated with each other (FIG. 10). This was in agreement with the seven genes clustering together in the same WGCNA gene module (green), since modules were constructed based on correlation of gene expression. As further indication of the specificity of these associations in human PC, the expression levels of closely related genes, e.g. BUB3 and KIF20B, were not correlated with any of the seven genes in PC (FIG. 10).

Figure 11A:
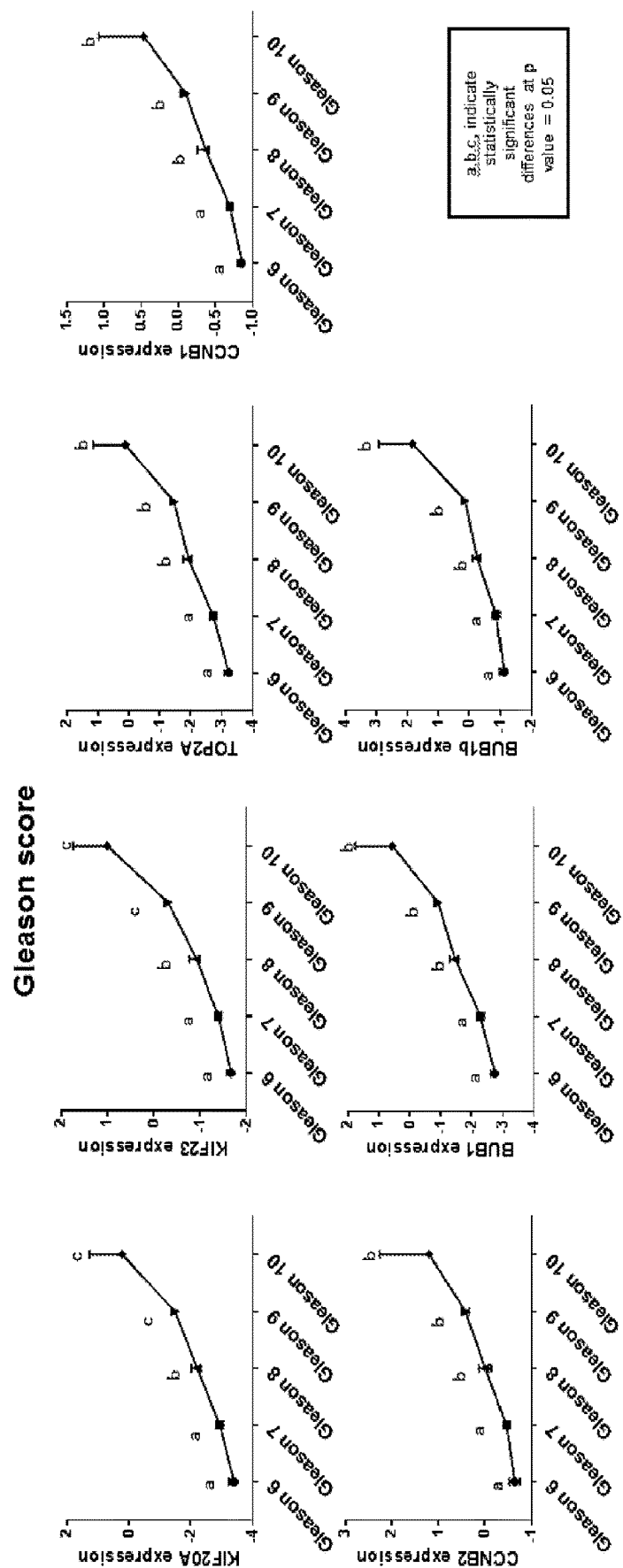
FIG. 11: Elevated expression of the seven gene set is associated with higher Gleason scores and other adverse indicators in human PC samples. PC patient RNA-SEQ data from the Prostate Adenocarcinoma TCGA provisional dataset (N=465) were used to plot the log 2 based transformed mean+s.e.m. of the gene expression levels for each PC sample according to each patient's Gleason score (A) and clinical stage (B). Kruskal-Wallis (P value<0.0001 for all panels, two-tailed) and Dunn's multiple comparisons test were performed. Different letters (a, b, c) denote statistically significant differences at a p value<0.05. C) PC patient RNA-seq data from the Prostate Adenocarcinoma TCGA provisional were analyzed to compare gene expression levels with the presence or absence of evidence for extraprostatic extension by MRI analysis (an adverse prognostic indicator). Data shows the mean±s.e.m., Unpaired t-test with Welch's correction were performed (two-tailed). ** Significant at a p value<0.05.
Figure 11B:
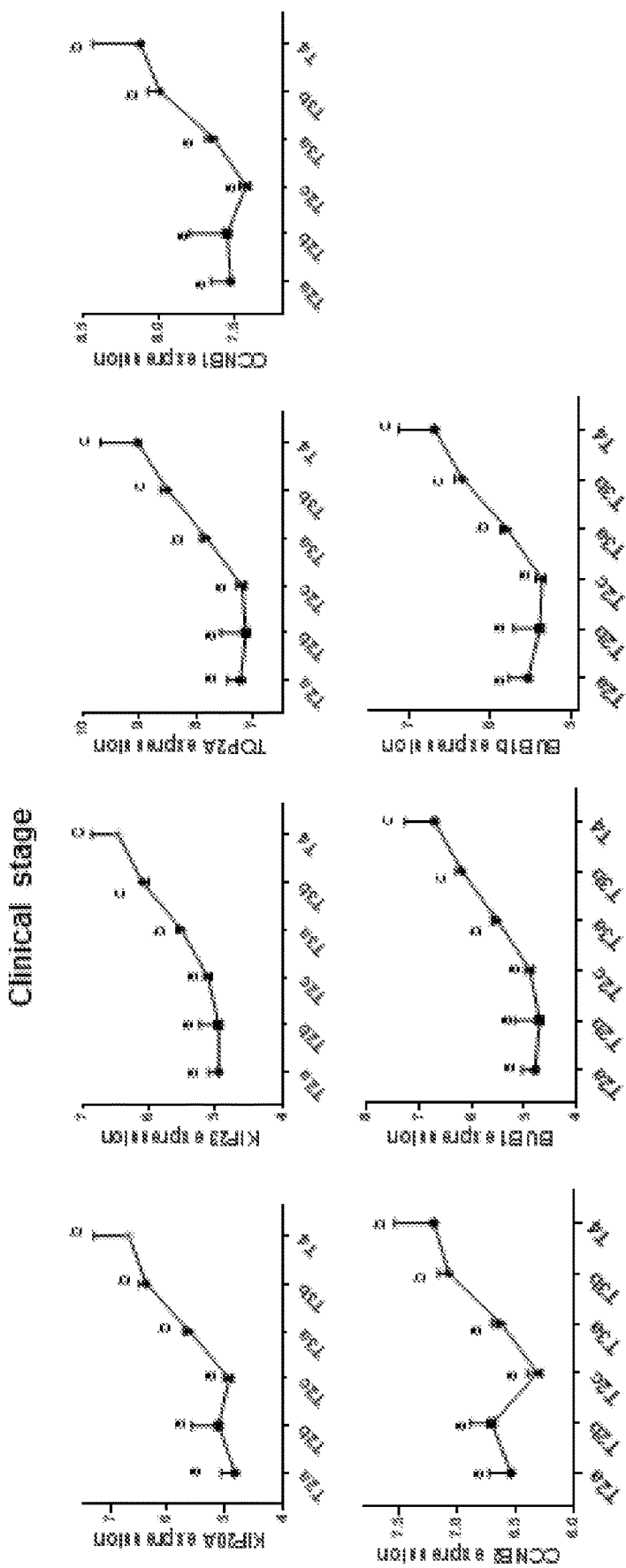
Figure 11C:
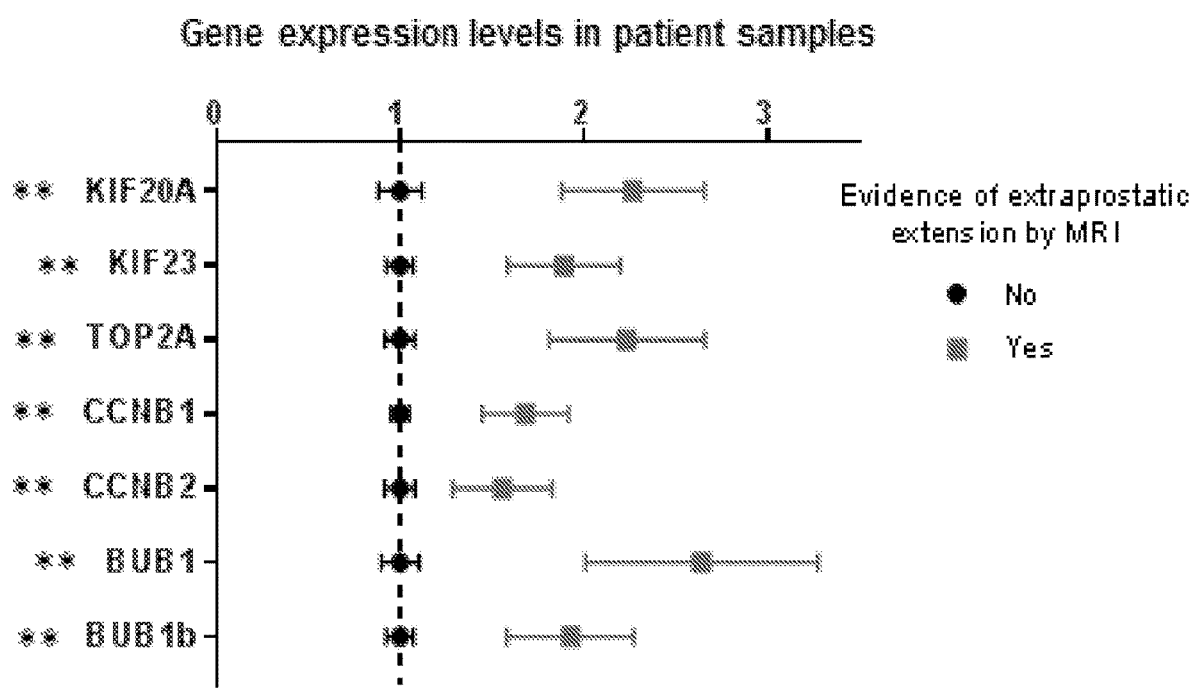

The expression of the seven genes correlated with well-established adverse prognostic indicators, including Gleason score (FIG. 11A), T clinical staging category (FIG. 11B), and MRI evidence of extraprostatic extension (FIG. 11C). The strong association between the expression levels of the seven genes with the tumor Gleason score in RNA-seq patient data was in agreement with the WGCNA analysis, showing a significant correlation of the expression levels of the genes in the green module with the Gleason score (FIG. 1A).

Figure 12:
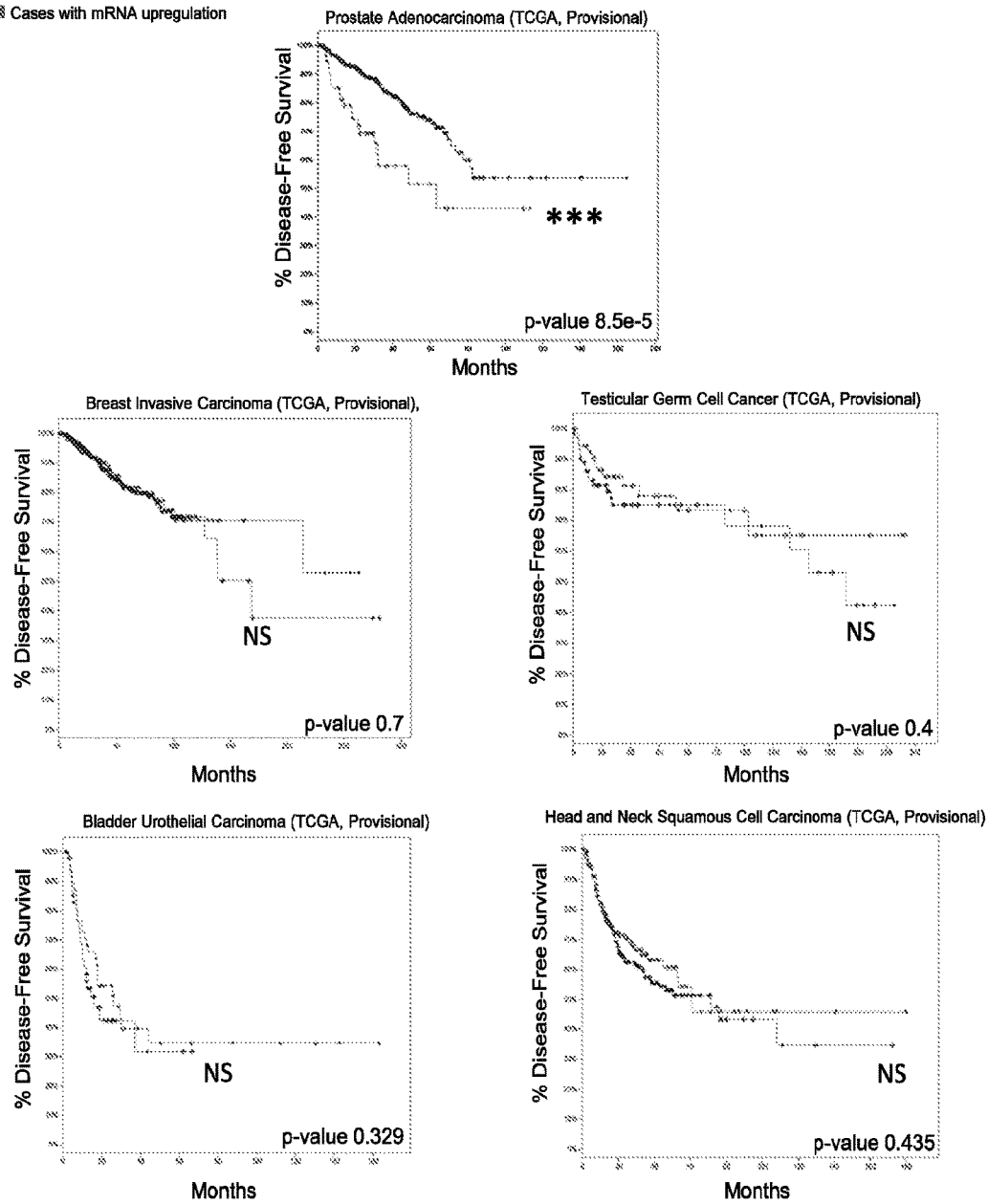
FIG. 12: The seven gene set does not have prognostic value in several other types of cancer. The Kaplan-Meier curves for Disease-Free Survival were built with cbioportal.org, using the following datasets: Breast Invasive Carcinoma (TCGA, Provisional), Testicular Germ Cell Cancer (TCGA, Provisional), Bladder Urothelial Carcinoma (TCGA, Provisional), Head and Neck Squamous Cell Carcinoma (TCGA, Provisional). The top curve denotes cases with normal expression of the gene set, and the bottom curve represents cases where the mRNA levels of one or more of the seven genes were upregulated (z-score threshold±1.5).

In addition, patients whose tumors had high expression (z-score threshold<1.96) of the seven gene set, exhibited significantly decreased disease-free survival (DFS) and lower overall survival in two distinct datasets compared to those patients with lower expression levels of the gene set (FIG. 2B). Interestingly, despite a well-established role for these genes in cell cycle/mitotic regulation, the gene set had no association with survival metrics for a number of other cancers (FIG. 12), supporting a PC-specific role of this gene set.

Figure 14:
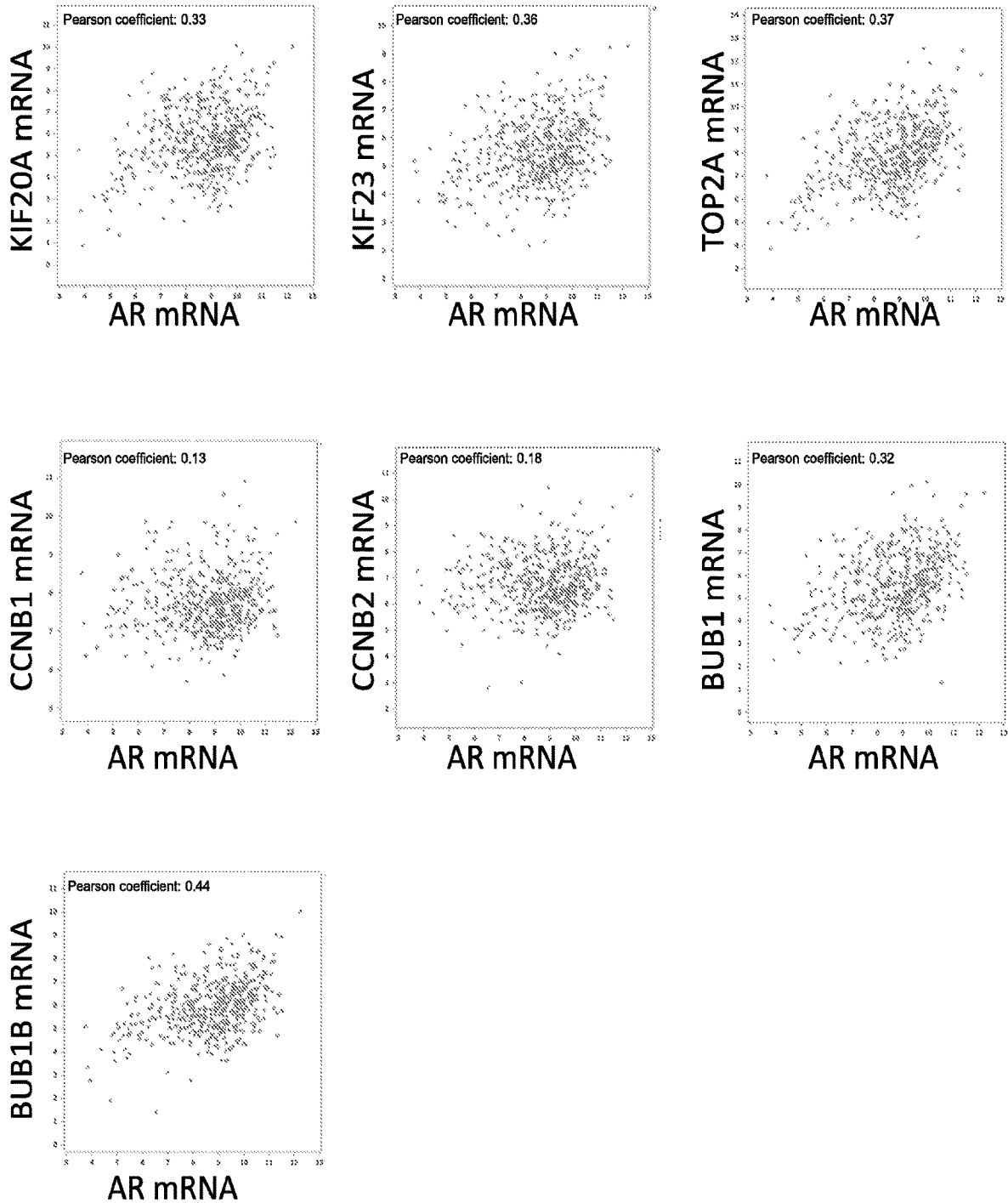
FIG. 14: The seven gene set is not associated to full length AR levels in human samples. The graphs show pairwise comparisons of the mRNA levels of each of the seven genes with the mRNA levels of AR in human PC samples obtained from the TCGA Provisional Adenocarcinoma dataset, where log 2 transformation was applied.

Because of the overlapping transcriptomes of full length AR and AR-V7, we examined whether full length AR also regulated the seven gene set. Androgen stimulation of the androgen-dependent cell line LNCaP and the CRPC cell line 22Rv1 did not significantly increase the expression levels of any of the seven genes (FIG. 13). In contrast, the expression levels of the positive control gene FKBP5 were substantially increased (FIG. 13). Moreover, pairwise comparisons showed that the expression levels of the seven genes were not associated with the expression levels of AR in the TCGA Prostate Adenocarcinoma patient dataset (FIG. 14).

Figure 3A:
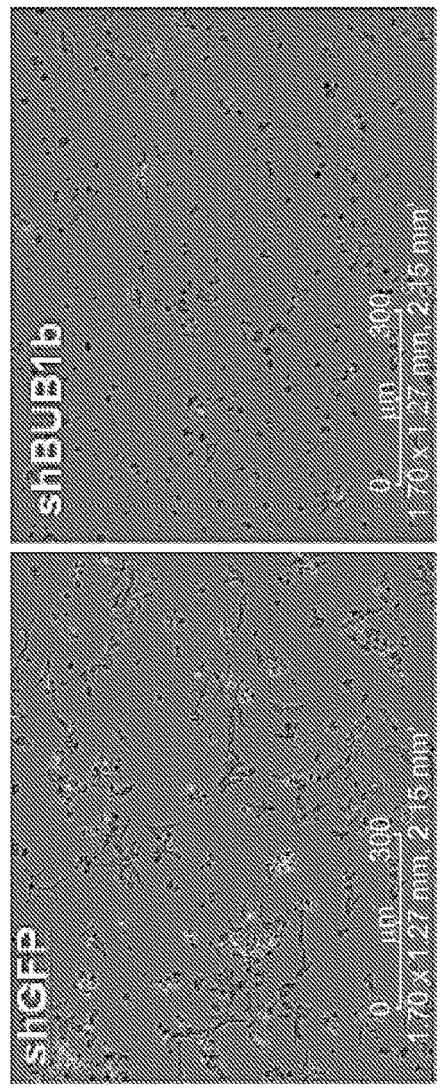
FIGS. 3A-3E: Depletion of the expression of each of the seven genes reduces CRPC cell proliferation and AR ligand-independent transcriptional activity.
Figure 3B:
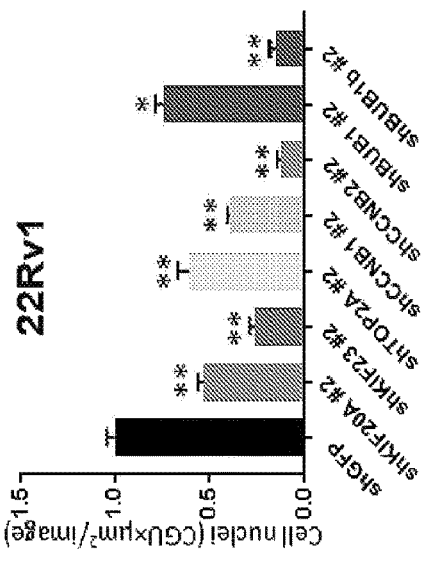
Figure 3C:
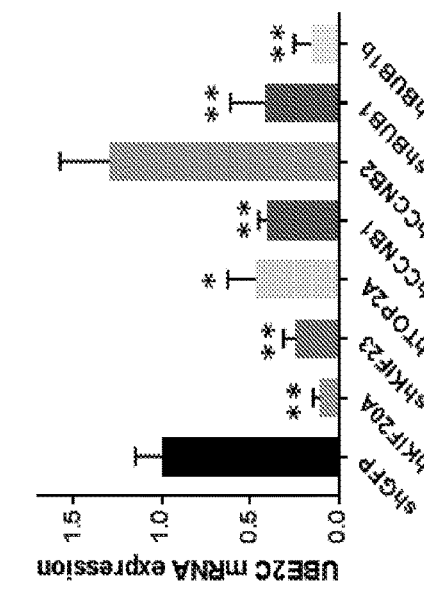
Figure 3D:
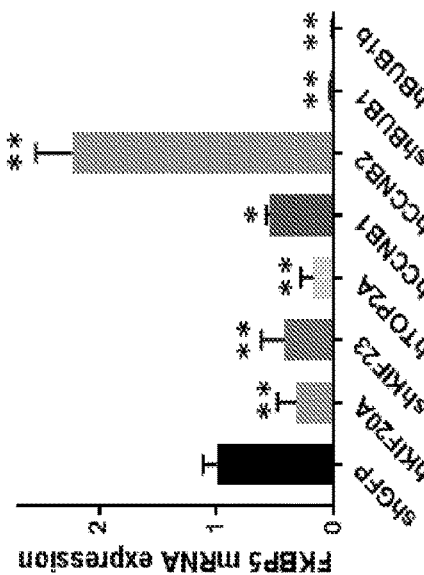
Figure 3E:
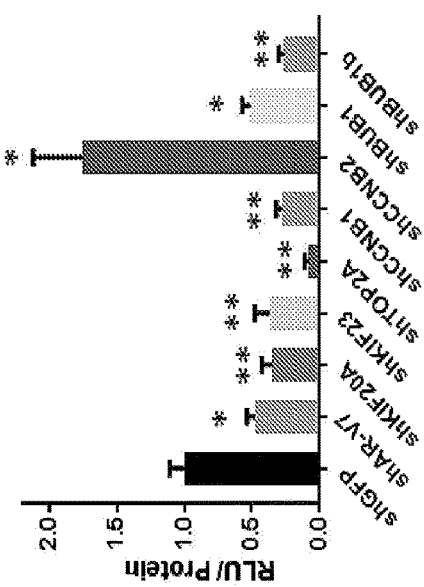
Figure 15B:
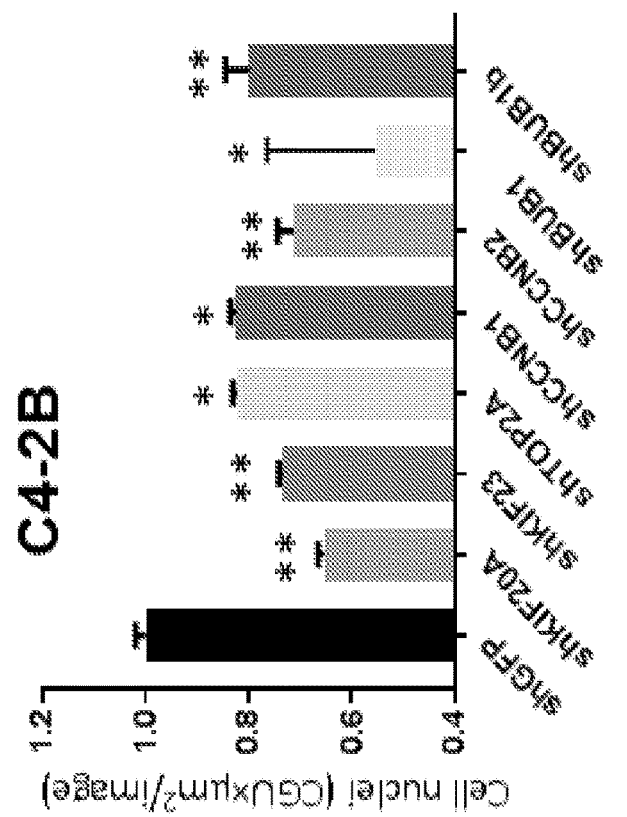
FIGS. 15A and 15B: Stable depletion of the expression of each of the seven genes reduces CRPC cell proliferation in two different cell lines. Cell proliferation was examined in the CRPC cell lines 22Rv1 (FIG. 15A) and C4-2B (FIG. 15B) following individual depletion of mRNAs for the seven genes or shGFP controls. shRNA constructs against the 3'UTR of each gene were used. Cell number was measured using a non-perturbing nuclear-restricted dye and quantified after 72 hours using Incucyte Zoom System. Data shown are mean±s.e.m. of 8 to 12 replicates normalized to their shGFP control. Kruskal-Wallis test (p value<0.0001, two-tailed) and Dunn's multiple comparisons test were performed.
Figure 15A:
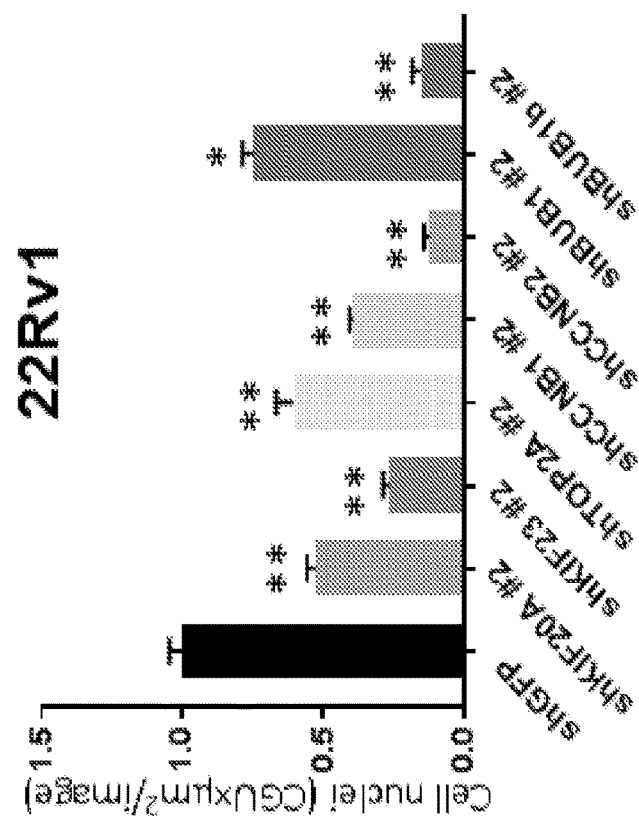
Figure 16:
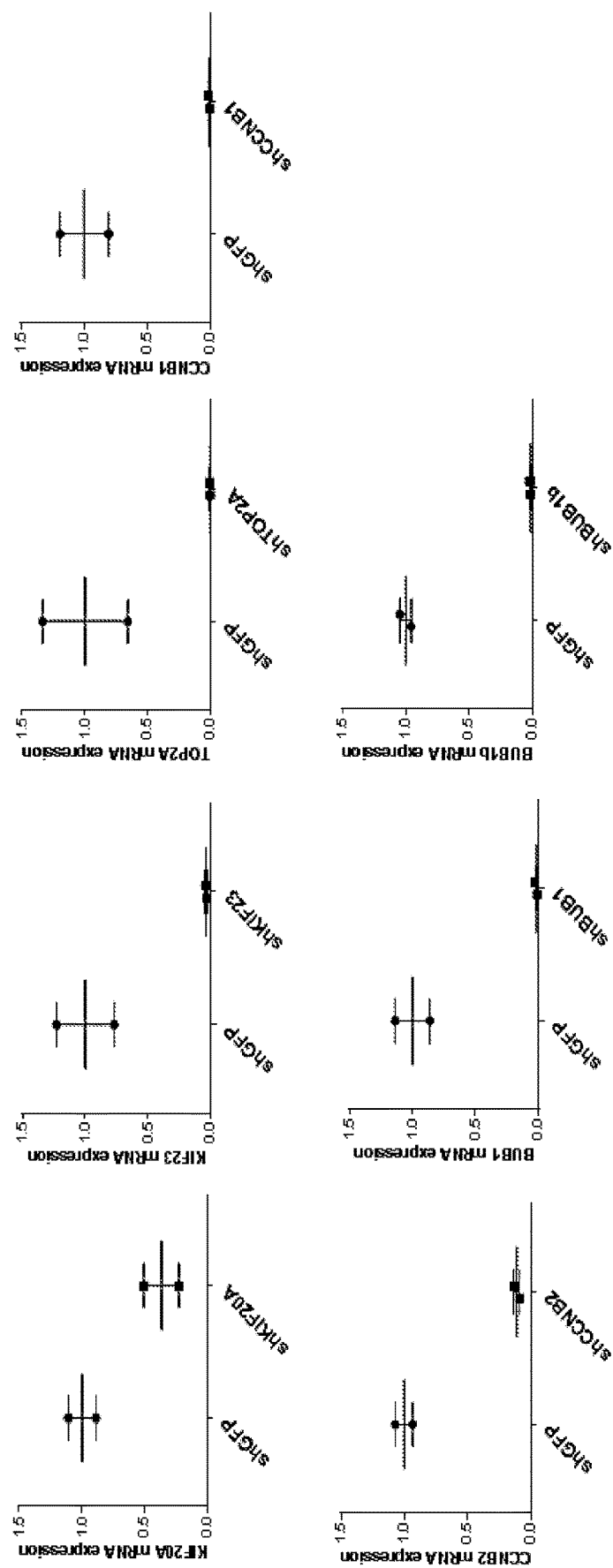
FIG. 16: Analysis of efficacy of shRNA-mediated depletion of the expression of each of the seven genes. 22Rv1 cells were stably transduced with shGFP (as a control) or shRNAs targeted to each of the seven genes. RT-qPCR analysis was performed in duplicate, and the results were normalized to GAPDH mRNA levels, and then to the respective shGFP controls. The median with 95% CI is shown.

Individual depletion of the expression of the seven genes, using two distinct shRNA constructs for each gene, in the human CRPC cell lines 22Ry1 (FIGS. 3A & 3B, FIG. 15) and C4-2B (FIG. 15A) decreased cell proliferation. Knockdown efficiency for each gene is shown in FIG. 16. Since the members of the gene set were not only regulated by AR-V7 (FIG. 1B), but also exhibited functional interactions with AR-V7 (FIG. 1C), we investigated whether these genes modified AR-V7 transcriptional activity by reporter gene assays. Experiments were performed in 22Rv1 in which AR activity in the absence of androgen is driven by ligand-independent AR-Vs (Dehm et al., 2008; Guo et al., 2009). Depleting the expression of six of the seven genes decreased ligand-independent AR transcriptional activity (FIG. 3C). Similarly, expression of well-known AR-V7 target genes, FKBP5 (FIG. 3D) and UBE2C (FIG. 3E), were significantly reduced upon knockdown of six of the seven genes in the absence of androgens. Depleting CCNB2 decreased CRPC proliferation but did not significantly reduce ligand-independent AR activity as measured in either assay (FIG. 3C-FIG. 3E). This latter finding indicates that the reduction of AR ligand-independent transcriptional activity upon depletion of the expression of the other six genes was not simply due to reduced cell proliferation. Thus, six members of the seven gene set, which is regulated by AR-V7 and present in the AR-V7 interactome (FIG. 1C), reciprocally enhanced ligand-independent AR activity in PC cells expressing AR-V7.

Example 3— Analysis of Therapeutic Drugs

Figure 4A:
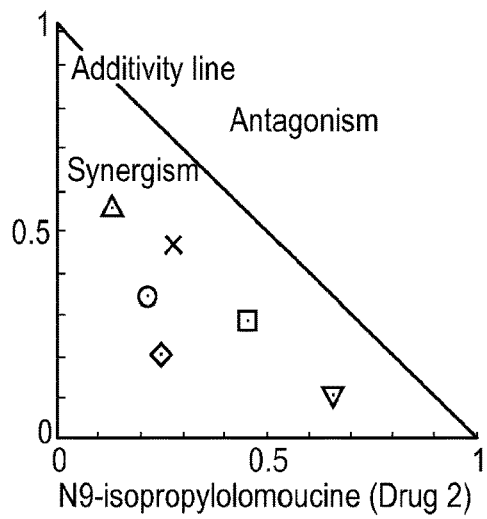
FIGS. 4A-4C: Combined pharmacologic inhibition of TOP2A and CCNB1 synergistically inhibits CRPC cell proliferation.
Figure 4B:
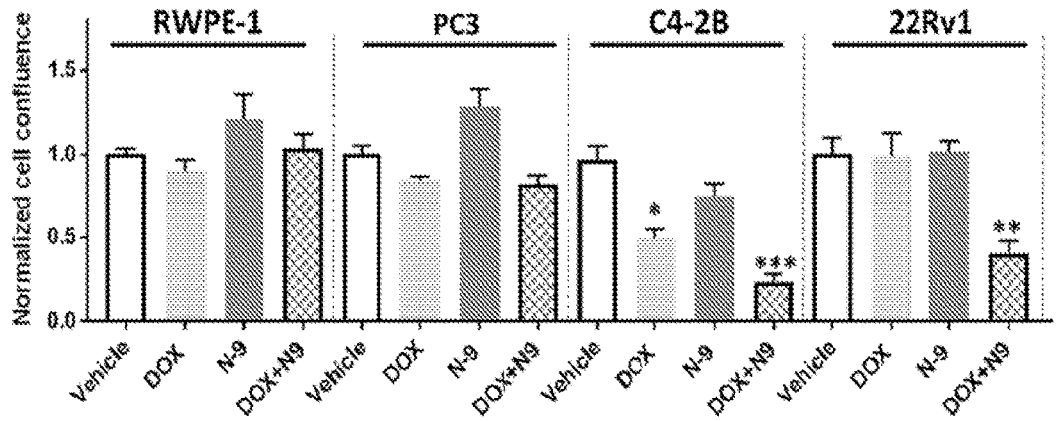
Figure 4C:
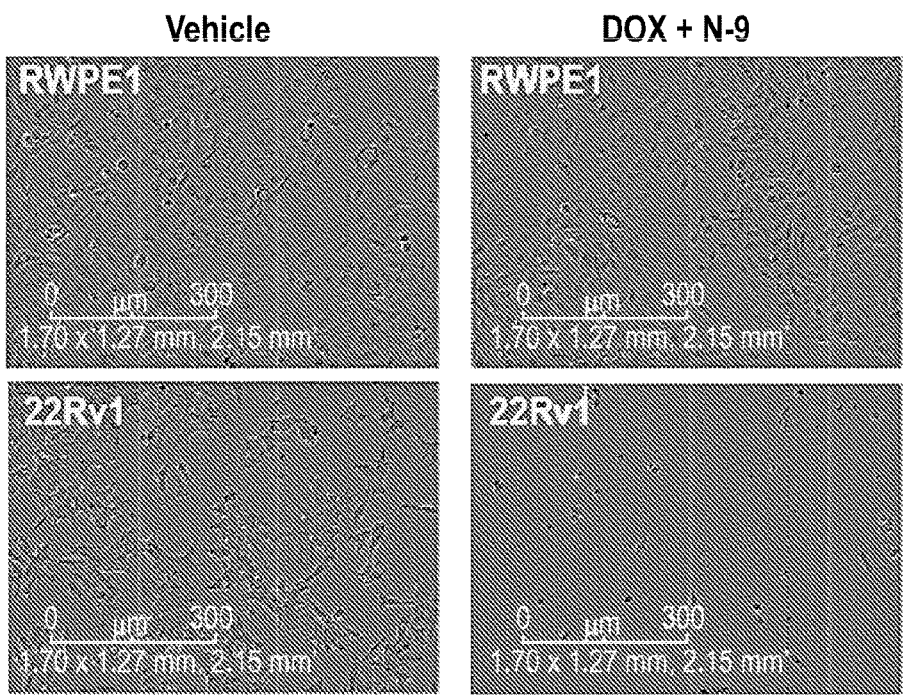
Figure 17:
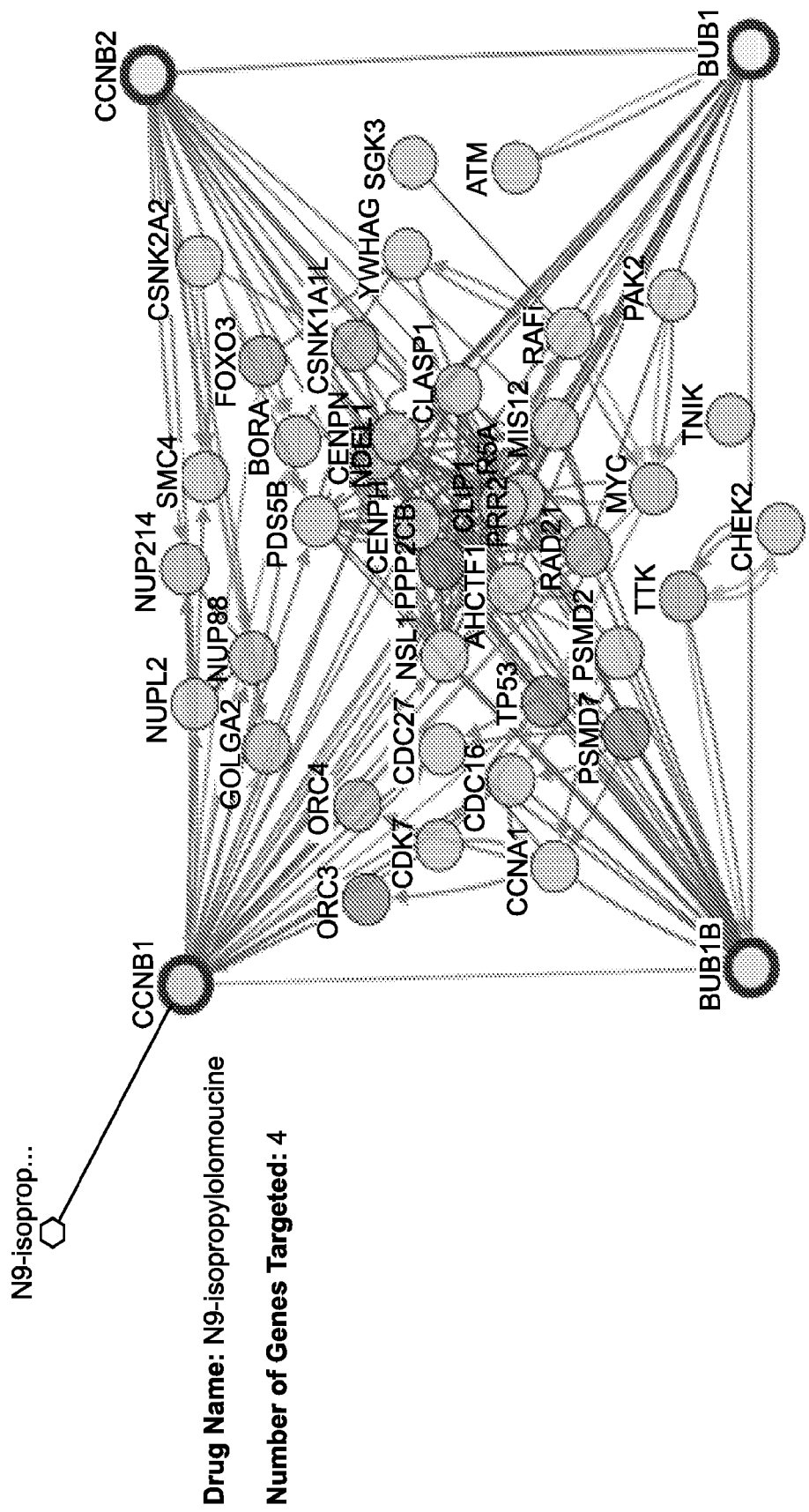
FIG. 17: The compound N-9 affects directly and indirectly four (CCNB1, CCNB2, BUB 1b and BUB1) of the seven genes due to pathway interactions. Network interactions were mapped using cbioportal.org as described in FIG. 1E legend.
Figure 19:
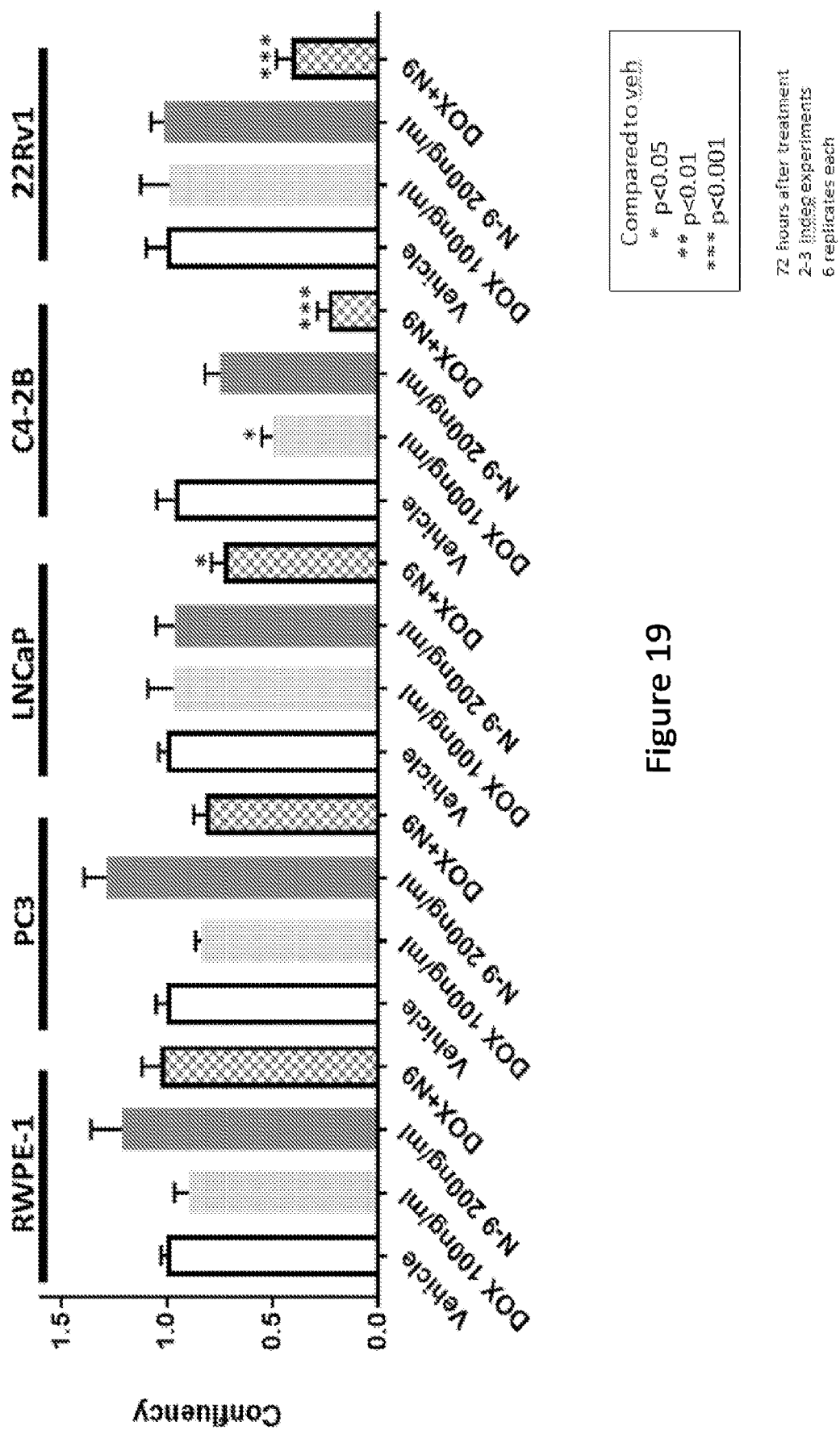
FIG. 19: The non-tumorigenic prostate epithelial cell line RWPE1, the AR-null PC cell line PC3, the CRPC cell lines C4-2B and 22Rvl and androgen dependent cell line LNCaP were treated for 72 hours with vehicle (DMSO), DOX (100 ng/mL [184 nM]), N-9 (200 ng/mL [613 nM]), or the combination of DOX (100 ng/mL [184 nM]) and N-9 (200 ng/mL [613 nM]). C4-2B and 22Rvl cells were kept in 10% CSS media. Cell confluence was monitored using the Incucyte Zoom System. Data represent two independent experiments, with four to six replicates each, showing the mean±s.e.m., and normalized to vehicle controls (Kruskal-Wallis test, P value<0.0001, two-tailed). *Significant at a p value<0.05, * p value<0.01, * p value<0.001.

The seven gene set may contain attractive therapeutic targets because these genes participate in interconnected cellular pathways (FIGS. 1A & 1E) and act upstream (FIG. 1C & FIGS. 3C-3E) and downstream of AR-V7 signaling (FIG. 1B). To test whether inhibition of this network decreased CRPC cell proliferation, we used doxoruhicin (DOX), which inhibits TOP2A (Tacar et al., 201.3), and N9-isopropylolomoucine (N-9), which targets CCNB 1/CDK1 (Havlicek et al, 1997). Because of pathway interactions (FIG. 17), these drugs may also inhibit the activity and/or levels of CCNB2, BUB1, and B UB1.1" The CRPC cell line 22Rv1 was treated with the compounds at various concentrations individually or in combination. The normalized isohologram and combination index (CI) were built and determined using Compusyn software. Nanomolar concentrations of the two drugs, DOX and N-9, exhibited synergistic (CI<0.9) antiproliferative effects over a range of combinations (FIG. 4A). We utilized the combination that had the lowest CI on a panel of different prostate cell lines (CI=0.45). While the single agents, DOX or N-9, or the combination of the two compounds had no significant effect on the proliferation of the non-tumorigenic prostate epithelial cell line RWPE-1, or the AR-null human PC cell line PC3: the combination of both compounds synergistically inhibited the proliferation of the two CRPC cell lines 22Rv1 and C4-2B (FIG. 4B. FIG. 4C and FIG. 19). Together the data indicate that CRPC cells are highly dependent on these seven genes for growth and survival.

Discussion

We identified a novel AR-V7 related gene set with prognostic and therapeutic value for PC using an integrated and unbiased data mining and experimental strategy (FIG. 5), which could be readily applied to other cancer types. As just one example, this approach could be adopted for cancers that are also driven by transcription factors, such as c-Myc, KIT, and estrogen receptor. Integrative approaches, such as those used here, transform one-dimensional cancer signatures into multidimensional networks of connecting modules (Rhodes & Chinnaiyan, 2005), which can facilitate more optimal therapeutic strategies. Our approach included meta-analyses of gene expression profiles from human prostate tumors to derive gene modules, whose expression coincides across disease states. These modules were integrated with data obtained from human PC cells that identified AR-V7 regulated genes and with data from an AR-V7 functional network, constructed through a powerful model genetic system. This multifaceted approach, which does not use any filtering or a priori assumptions, resulted in the identification of disease-relevant genes that were regulated by AR-V7 and that reciprocally enhanced AR-V7 oncogenic activity. We performed extensive inter-validation with independent patient datasets and extended findings using cell-based experimentation.

We performed a meta analysis of microarray data on clinical PC samples, including 375 samples from 8 different datasets (obtained from the same type of array so gene expression measurements could be directly compared) and encompassing 6 different phenotypes/disease stages. The large number of samples provided robustness to the module definition, as well as power in the ability to identify relevant modules. The gene members of the green module had expression levels significantly associated with and upregulated upon cancer onset and progression to CRPC, as well as Gleason score. The unbiased WGCNA clustering revealed a module (green) that contained 60 genes regulated by AR-V7.

Ligand activated AR is well recognized as a regulator of the cyclin D-RB axis in prostate cancer (reviewed in Balk & Knudsen, 2008). However, our findings suggest that AR variants, in particular AR-V7, are intricately related to G2-M phase cellular dynamics. An important implication is that the seven genes represent a vulnerability for AR-V7-driven CRPC and provide possible approaches for overcoming androgen deprivation therapy and taxane resistance in CRPC patients.

There is a critical need to identify gene signatures that robustly predict PC aggressiveness and that can inform active surveillance disease management decisions (Cooperberg & Carroll, 2015). We found that patients with tumors exhibiting higher expression levels of the seven genes had an elevated risk of relapse after primary therapy, and a greater risk of death. Thus, this seven gene set has the potential for use in stratifying patients and guiding treatment according to clinical risk.

Despite having established roles in cell-cycle and cell division, which are hallmarks of all cancers, the seven gene set did not predict patient survival metrics in other types of cancer from TCGA dataset cohorts. This finding supports a PC-specific role of this gene set, especially for cells that depend on AR-V7 signaling. In fact, six out of the seven genes encoded proteins that enhanced AR ligand-independent activity in cell based-assays. This finding may help to explain why the seven genes are selectively associated with PC progression. Moreover, another cell cycle progression (CCP) signature has shown prognostic value in PC patients (Cuzick et al., 2011), supporting the importance of cell cycle genes in predicting PC patient outcome. This other signature contains only three out the seven genes identified here, but requires the measurement of 31 genes in total.

The seven genes could interact with and promote AR-V7 transcriptional activity in various ways. Li et al., 2015 showed that TOP2A inhibition reduces full length AR and AR-V7 transcriptional activity, through decreased AR recruitment to target gene promoters and reduced nuclear localization. In addition Chen et al., 2006 showed that CCNB1/CDK1 stabilizes full length AR protein levels through phosphorylation of Ser-81. This residue is located in the activation function 1 (AF-1) region in the N-terminal domain, which is also present in AR-V7. Thus, CCNB1 may regulate AR-V7 through this or a similar mechanism. The two kinesins in the seven gene set (KIF20a and KIF23) as well as BUB1 and BUB 1b may enhance AR-V7 transcriptional activity through modifications of AR-V7 mRNA or protein levels, and/or through increasing AR-V7 nuclear levels. CCNB2 was the one gene of the seven that upon knock down did not decrease ligand-independent AR activity. This finding may relate to the observation that CCNB2 is largely cytoplasmic and more specifically associated to Golgi bodies and not to microtubules or the nucleus (where the other 6 proteins and AR-V7 mostly reside).

This study was undertaken, at least in part, to develop, apply and validate a novel gene discovery method, which in this case was centered on AR-V7 networks and their role in PC. Since most PC patient tissue and cell lines that express AR-V7 also express full length AR (Guo et al., 2009; Holmberg et al., 2011), and as AR-V7 can heterodimerize with full length AR, any actions of AR-V7 likely occur in the context of full length AR. The extent to which the full length AR transcriptome overlaps with AR-V7 (or heterodimers of full length AR and AR variants) is not fully understood (Cao et al., 2014; Hu et al., 2011; Hu et al., 2012; Watson et al., 2010, Xu et al., 2015). However, we found that ligand-activated full length AR did not regulate the expression levels of the seven gene set. Further, full length AR did not correlate with the expression levels of the gene set in patients.

Several members of the seven gene set also regulate or enhance full length AR activity. Thus, the seven identified genes, while not being regulated by full length AR, are likely to participate at least in some settings in enhancing full length AR. Indeed, as discussed below C4-2B cells, which are not thought to be driven by AR variants, were growth inhibited by the combination of nanomolar doses of doxorubicin and N9-Isopropylolomoucine (N-9).

Because the seven genes belong to highly interconnected pathways and networks that control each other's expression and/or activities, there is a strong likelihood that inhibition of any two of these genes would provide significantly enhanced antitumor effects. Doxorubicin (targeting the activity of TOP2A) and N9-Isopropylolomoucine (N-9) (targeting CCCNB1/CDK1 activity, and indirectly affecting 3 other genes), used within the nanomolar range, provided synergistic suppression of CRPC growth in 22Rv1 cells, which express AR-V7, as well as other AR-variants (Guo et al., 2009; Peacock et al., 2012; Yang et al., 2011) and C4-2B, which are also highly reliant on AR signaling (ref). In contrast, the two compounds had no effect on non-tumorigenic or AR-null cells. Additionally CRPC cells, especially those that exhibit active AR signaling, may possess a unique dependency on these seven genes for growth and survival. Such a dependency is predicted since these genes are not only targets of AR-V7 but also enhance ligand-independent AR activity.

In summary, we developed and used here an integrative and unbiased data mining and experimental strategy, to define a new AR-V7 related gene set with prognostic and therapeutic value for PC. These findings support future in vivo and possibly clinical studies in which combinations of these seven gene products are inhibited in PC. Additionally, this seven gene set should be explored in prospective studies of PC to determine the prognostic capacity in different clinical risk settings.

Example 4— Drug Resistance

Since AR-V7 is associated with enzalutamide resistance (see, e.g., Antonaraikis et al., 2014; Antonaraikis et al., 2017), and the seven gene set constitutes a network that is regulated by and interacts with AR-V7, we looked into whether the expression levels of the seven genes was associated with enzalutamide resistance. Analysis of the GSE78201 dataset (Kregel et al., 2016), showed that both androgen-dependent cell lines, VCaP and LNCaP, had a tendency towards increased levels of the 7 genes after becoming enzalutamide resistant (following at least 6 months of treatment) (FIG. 18). Even though statistical significance was achieved for a limited amount of paired samples (such as CCNB1 and BUB 1b), this could be attributed to the limited amount of samples (n=2-4 for each group).

Reference cited: Kregel, S., Chen, J. L., Tom, W., Krishnan, V., Kach, J., Brechka, H., . . . & Vander Griend, D. J. (2016). Acquired resistance to the second-generation androgen receptor antagonist enzalutamide in castration-resistant prostate cancer. Oncotarget, 7(18), 26259.

References for Examples 2 and 3

Antonarakis, E. S., Lu, C., Wang, H., Luber, B., Nakazawa, M., Roeser, J. C., . . . & Lotan, T. L. (2014). AR-V7 and resistance to enzalutamide and abiraterone in prostate cancer. New England Journal of Medicine, 371(11), 1028-1038.

Antonarakis, E. S., Lu, C., Luber, B., Wang, H., Chen, Y., Zhu, Y., . . . & Pienta, K. J. (2017). Clinical significance of androgen receptor splice variant-7 mRNA detection in circulating tumor cells of men with metastatic castration-resistant prostate cancer treated with first- and second-line abiraterone and enzalutamide. Journal of Clinical Oncology, JCO-2016.

Balk, S. P., & Knudsen, K. E. (2008). AR, the cell cycle, and prostate cancer. Nuclear receptor signaling, 6.

Bjartell, A., Montironi, R., Berney, D. M., & Egevad, L. (2011). Tumour markers in prostate cancer II: diagnostic and prognostic cellular biomarkers. Acta Oncologica, 50(supl), 76-84.

Cao, B., Qi, Y., Zhang, G., Xu, D., Zhan, Y., Alvarez, X., . . . & Zhang, H. (2014). Androgen receptor splice variants activating the full-length receptor in mediating resistance to androgen-directed therapy. Oncotarget, 5(6), 1635.

Chan, S. C., Li, Y., & Dehm, S. M. (2012). Androgen receptor splice variants activate androgen receptor target genes and support aberrant prostate cancer cell growth independent of canonical androgen receptor nuclear localization signal. Journal of Biological Chemistry, 287(23), 19736-19749.

Chan, S. C., Selth, L. A., Li, Y., Nyquist, M. D., Miao, L., Bradner, J. E., . . . & Dehm, S. M. (2015). Targeting chromatin binding regulation of constitutively active AR variants to overcome prostate cancer resistance to endocrine-based therapies. Nucleic acids research, 43(12), 5880-5897.

Chandran, V., Coppola, G., Nawabi, H., Omura, T., Versano, R., Huebner, E. A., & Blesch, A. (2016). A systems-level analysis of the peripheral nerve intrinsic axonal growth program. Neuron, 89(5), 956-970.

Chen, S., Xu, Y., Yuan, X., Bubley, G. J., & Balk, S. P. (2006). Androgen receptor phosphorylation and stabilization in prostate cancer by cyclin-dependent kinase 1. Proceedings of the National Academy of Sciences, 103(43), 15969-15974.

Chia, K. M., Liu, J., Francis, G. D., & Naderi, A. (2011). A feedback loop between androgen receptor and ERK signaling in estrogen receptor-negative breast cancer. Neoplasia, 13(2), 154-166.

Chou, T. C., & Talalay, P. (1984). Quantitative analysis of dose-effect relationships: the combined effects of multiple drugs or enzyme inhibitors. Advances in enzyme regulation, 22, 27-55.

Cooperberg, M. R., & Carroll, P. R. (2015). Trends in management for patients with localized prostate cancer, 1990-2013. Jama, 314(1), 80-82.

Cuzick, J., Swanson, G. P., Fisher, G., Brothman, A. R., Berney, D. M., Reid, J. E., . . . & Moller, H. (2011). Prognostic value of an RNA expression signature derived from cell cycle proliferation genes in patients with prostate cancer: a retrospective study. The lancet oncology, 12(3), 245-255.

Dehm, S. M., Schmidt, L. J., Heemers, H. V., Vessella, R. L., & Tindall, D. J. (2008). Splicing of a novel androgen receptor exon generates a constitutively active androgen receptor that mediates prostate cancer therapy resistance. Cancer research, Dixon, S. J., Fedyshyn, Y., Koh, J. L., Prasad, T. K., Chahwan, C., Chua, G., . . . & Kim, D. U. (2008). Significant conservation of synthetic lethal genetic interaction networks between distantly related eukaryotes. Proceedings of the National Academy of Sciences, 105(43), 16653-16658.

Goodwin, J. F., Kothari, V., Drake, J. M., Zhao, S., Dylgjeri, E., Dean, J. L., . . . & Magee, M. S. (2015). DNA-PKcs-mediated transcriptional regulation drives prostate cancer progression and metastasis. Cancer cell, 28(1), 97-113.

Guo, Z., Yang, X., Sun, F., Jiang, R., Linn, D. E., Chen, H., . . . & Kung, H. J. (2009). A novel androgen receptor splice variant is up-regulated during prostate cancer progression and promotes androgen depletion—resistant growth. Cancer research, 69(6), 2305-2313.

Havlicek, L., Hanuš, J., Vesel, J., Leclerc, S., Meijer, L., Shaw, G., & Strnad, M. (1997). Cytokinin-derived cyclin-dependent kinase inhibitors: synthesis and cdc2 inhibitory activity of olomoucine and related compounds. Journal of medicinal chemistry, 40(4), 408-412.

He, Y., Lu, J., Ye, Z., Hao, S., Wang, L., Kohli, M., . . . & Huang, H. (2018). Androgen receptor splice variants bind to constitutively open chromatin and promote abiraterone-resistant growth of prostate cancer. Nucleic acids research.

Ho, Y., & Dehm, S. M. (2017). Androgen Receptor Rearrangement and Splicing Variants in Resistance to Endocrine Therapies in Prostate Cancer. Endocrinology, 158(6), 1533-1542.

Hornberg, E., Ylitalo, E. B., Crnalic, S., Antti, H., Stattin, P., Widmark, A., . . . & Wikström, P. (2011). Expression of androgen receptor splice variants in prostate cancer bone metastases is associated with castration-resistance and short survival. PloS one, 6(4), e19059.

Hu, R., Lu, C., Mostaghel, E. A., Yegnasubramanian, S., Gurel, M., Tannahill, C., & Plymate, S. R. (2012). Distinct transcriptional programs mediated by the ligand-dependent full-length androgen receptor and its splice variants in castration-resistant prostate cancer. Cancer research, 72(14), 3457-3462.

Kadarmideen, H. N., & Watson-Haigh, N. S. (2012). Building gene co-expression networks using transcriptomics data for systems biology investigations: Comparison of methods using microarray data. Bioinformation, 8(18), 855.

Karacosta, L. G., Foster, B. A., Azabdaftari, G., Feliciano, D. M., & Edelman, A. M. (2012). A regulatory feedback loop between Ca2±/calmodulin-dependent protein kinase kinase 2 (CaMKK2) and the androgen receptor in prostate cancer progression. Journal of Biological Chemistry, 287(29), 24832-24843.

Karantanos, T., Corn, P. G., & Thompson, T. C. (2013). Prostate cancer progression after androgen deprivation therapy: mechanisms of castrate resistance and novel therapeutic approaches. Oncogene, 32(49), 5501-5511.

Knudsen, K. E., & Penning, T. M. (2010). Partners in crime: deregulation of AR activity and androgen synthesis in prostate cancer. Trends in Endocrinology & Metabolism, 21(5), 315-324.

Kong, D., Sethi, S., Li, Y., Chen, W., Sakr, W. A., Heath, E., & Sarkar, F. H. (2015). Androgen receptor splice variants contribute to prostate cancer aggressiveness through induction of EMT and expression of stem cell marker genes. The Prostate, 75(2), 161-174.

Kreeger, P. K., & Lauffenburger, D. A. (2009). Cancer systems biology: a network modeling perspective. Carcinogenesis, 31(1), 2-8.

Lamb, J., Crawford, E. D., Peck, D., Modell, J. W., Blat, I. C., Wrobel, M. J., & Reich, M. (2006). The Connectivity Map: using gene-expression signatures to connect small molecules, genes, and disease. science, 313(5795), 1929-1935.

Langfelder, P., & Horvath, S. (2008). WGCNA: an R package for weighted correlation network analysis. BMC bioinformatics, 9(1), 559.

Li, H., Xie, N., Gleave, M. E., & Dong, X. (2015). Catalytic inhibitors of DNA topoisomerase II suppress the androgen receptor signaling and prostate cancer progression. Oncotarget, 6(24), 20474.

Li, Y., Chan, S. C., Brand, L. J., Hwang, T. H., Silverstein, K. A., & Dchm, S. M. (2013). Androgen receptor splice variants mediate enzalutamide resistance in castration-resistant prostate cancer cell lines. Cancer research, 73(2), 483-489.

Luo J, et al. Role of Androgen Receptor Variants in Prostate Cancer: Report from the 2017 Mission Androgen Receptor Variants Meeting. Eur Urol (2017), https://doi.org/10.1016/j.eururo.2017.11.038

Marcias, G., Erdmann, E., Lapouge, G., Siebert, C., Barthelemy, P., Duclos, B., . . . & Kurtz, J. E. (2010). Identification of novel truncated androgen receptor (AR) mutants including unreported pre-mRNA splicing variants in the 22Rv1 hormone-refractory prostate cancer (PCa) cell line. Human mutation, 31(1), 74-80.

Moreno, S., Klar, A., & Nurse, P. (1991). [56] Molecular genetic analysis of fission yeast Schizosaccharomyces pombe. Methods in enzymology, 194, 795-823.

Prensner, J. R., Rubin, M. A., Wei, J. T., & Chinnaiyan, A. M. (2012). Beyond PSA: the next generation of prostate cancer biomarkers. Science translational medicine, 4(127), 127rv3-127rv3.

Qu, Y., Dai, B., Ye, D., Kong, Y., Chang, K., Jia, Z., . . . & Shi, G. (2015). Constitutively active AR-V7 plays an essential role in the development and progression of castration-resistant prostate cancer. Scientific reports, 5, 7654.

Rhodes, D. R., & Chinnaiyan, A. M. (2005). Integrative analysis of the cancer transcriptome. Nature genetics, 37, S31-S37.

Shafi, A. A., Putluri, V., Arnold, J. M., Tsouko, E., Maity, S., Roberts, J. M., . . . & Weigel, N. L. (2015). Differential regulation of metabolic pathways by androgen receptor (AR) and its constitutively active splice variant, AR-V7, in prostate cancer cells. Oncotarget, 6(31), 31997.

Siegel, R. L., Miller, K. D., 85 Jemal, A. (2016). Cancer statistics, 2016. CA: a cancer journal for clinicians, 66(1), 7-30.

Tacar, 0., Sriamornsak, P., & Dass, C. R. (2013). Doxorubicin: an update on anticancer molecular action, toxicity and novel drug delivery systems. Journal of Pharmacy and Pharmacology, 65(2), 157-170.

Watson, P. A., Chen, Y. F., Balbas, M. D., Wongvipat, J., Socci, N. D., Viale, A., & Sawyers, C. L. (2010). Constitutively active androgen receptor splice variants expressed in castration-resistant prostate cancer require full-length androgen receptor. Proceedings of the national academy of sciences, 107(39), 16759-16765.

Wiley, D. J., Juan, I., Le, H., Cai, X., Baumbach, L., Beattie, C., & D'Urso, G. (2014). Yeast Augmented Network Analysis (YANA): a new systems approach to identify therapeutic targets for human genetic diseases. F1000Research, 3.

Xu, D., Zhan, Y., Qi, Y., Cao, B., Bai, S., Xu, W., . . . & Dong, Y. (2015). Androgen receptor splice variants dimerize to transactivate target genes. Cancer research, 75(17), 3663-3671.

Yang, X., Guo, Z., Sun, F., Li, W., Alfano, A., Shimelis, H., . . . & Veenstra, T. D. (2011). Novel membrane-associated androgen receptor splice variant potentiates proliferative and survival responses in prostate cancer cells. Journal of Biological Chemistry, 286(41), 36152-36160.

Yu, Y., Zhang, Y., Guan, W., Huang, T., Kang, J., Sheng, X., & Qi, J. (2014). Androgen receptor promotes the oncogenic function of overexpressed Jagged1 in prostate cancer by enhancing cyclin B1 expression via Akt phosphorylation. Molecular Cancer Research, 12(6), 830-842.

Zhang, B., & Horvath, S. (2005). A general framework for weighted gene co-expression network analysis. Statistical applications in genetics and molecular biology, 4(1).

Zhang, X., Morrissey, C., Sun, S., Ketchandji, M., Nelson, P. S., True, L. D., . . . & Plymate, S. R. (2011). Androgen receptor variants occur frequently in castration resistant prostate cancer metastases. PloS one, 6(11), e27970.

Zhu, L., Ding, Y., Chen, C. Y., Wang, L., Huo, Z., Kim, S., . . . & Tseng, G. C. (2016). MetaDCN: meta-analysis framework for differential co-expression network detection with an application in breast cancer. Bioinformatics, 33(8), 1121-1129.

What is claimed is:

1. A method of decreasing proliferation of prostate cancer cells comprising contacting the cells with doxorubicin (DOX) and N9-isopropylolomoucine (N-9) in an amount effective to decrease proliferation of the cancer cells, wherein the prostate cancer is castrate-resistant prostate cancer (CRPC).

2. The method of claim 1, wherein the CRPC cells are selected from the group consisting of 22Rv1 cells and C4-2B cells.

3. The method of claim 1, wherein the amount of DOX in the combination is less than 2 mg/mL.

4. The method of claim 1, wherein the amount of N-9 in the combination is less than 2 mg/mL.

5. A method of treating prostate cancer in a subject in need thereof comprising administering to the subject doxorubicin (DOX) and N9-isopropylolomoucine (N-9) a mitotic cyclin dependent kinase inhibitor in amounts effective to treat prostate cancer in the subject, wherein the prostate cancer is castrate-resistant prostate cancer (CRPC).

6. The method of claim 5, wherein the subject is resistant to treatment with enzalutamide.

7. The method of claim 5, wherein the DOX and N-9 are administered to the subject in separate compositions.

8. The method of claim 5, wherein the DOX and N-9 are administered in the same composition.

9. The method of claim 7, wherein DOX is administered within 24 hours of N-9.

10. The method of claim 5, wherein the amount of the DOX in the combination is less than 2 mg/mL.

11. The method of claim 5, wherein the amount of N-9 in the combination is less than 2 mg/mL.

12. The method of claim 5, further comprising administering a further therapeutic agent selected from the group consisting of an androgen receptor antagonist, an inhibitor of androgen synthesis, a gonadotropin-releasing hormone (GnRH) agonist and a GnRH antagonist to the subject.

13. A method of treating prostate cancer in a subject in need thereof comprising
   (a) identifying elevated levels of kinesin family-member 20A (KIF20A), kinesin family-member 23 (KIF23), topoisomerase DNA II alpha (TOP2A), cyclin B1 (CCNB1) cyclin B2 (CCNB2), mitotic checkpoint serine/threonine kinase (BUB1) and mitotic checkpoint serine/threonine kinase B (BUB1b) in a tumor sample from the subject relative to a reference standard; and
   (b) administering doxorubicin (DOX) and a mitotic cyclin dependent kinase inhibitor in amounts effective to treat prostate cancer in the subject.

14. The method of claim 13, wherein the prostate cancer is castrate-resistant prostate cancer (CRPC).

* * * * *